US009062275B2

(12) United States Patent
Cela Lopez

(10) Patent No.: US 9,062,275 B2
(45) Date of Patent: Jun. 23, 2015

(54) COMPOSITIONS RICH IN OMEGA-3 FATTY ACIDS WITH A LOW CONTENT IN PHYTANIC ACID

(75) Inventor: Jose Manuel Cela Lopez, Kinvara (IE)

(73) Assignee: NATAC PHARMA, S.L., Madrid (ES)

( * ) Notice: Subject to any disclaimer, the term of this patent is extended or adjusted under 35 U.S.C. 154(b) by 612 days.

(21) Appl. No.: 13/264,659

(22) PCT Filed: Apr. 17, 2009

(86) PCT No.: PCT/EP2009/002842
§ 371 (c)(1),
(2), (4) Date: Nov. 18, 2011

(87) PCT Pub. No.: WO2010/118761
PCT Pub. Date: Oct. 21, 2010

(65) Prior Publication Data
US 2012/0053242 A1    Mar. 1, 2012

(51) Int. Cl.
| C11C 1/02 | (2006.01) |
| A23L 1/30 | (2006.01) |
| C11C 1/08 | (2006.01) |
| C11C 3/02 | (2006.01) |

(52) U.S. Cl.
CPC ............ *C11C 1/025* (2013.01); *A23L 1/3008* (2013.01); *A23V 2002/00* (2013.01); *C11C 1/08* (2013.01); *C11C 3/02* (2013.01)

(58) Field of Classification Search
CPC .................................... C07C 3/00; C07C 3/02
See application file for complete search history.

(56) References Cited

U.S. PATENT DOCUMENTS 5,698,594 A * 12/1997 Breivik et al. ................ 514/560

OTHER PUBLICATIONS

Francis, P. J., et al., Genetics of inherited retinal diseases, 2006, Journal of hte Royal Socieyt of Medicine, vol. 99, pp. 189-191.*
Hamel, C., Retinitis pigmentosa, 2006, Orphanet Journal of Rare Diseases, I:40, 12 pages.*
van den Brink, D. M., et al., Phytanic acid: productin from phytol, its breakdown and role in human disease, 2006, Cell. Mol. Live Sci., vol. 63, pp. 1752-1765.*
Schonfeld, P., et al., In brain mitochondria the branched-chain fatty acid phytanic acid impairs enerty transductoin and sensitizes for permeability transition, 2004, Biochem J., vol. 383, pp. 121-128.*
National Eye Institute, Facts about the Cornea and Corneal diseases, 2013, National Institute of Health, 16 pages.*
St. Mary's Hospital, Retinal Dystrophy, 2010, Central Manchester University Hospitals NHS Foundation, 8 pages.*
Chopdar, A, et al., Age related macular degeneration, 2003, BMJ Clinical review, vol. 326 pp. 485-488.*

(Continued)

Primary Examiner — Yate K Cutliff
(74) Attorney, Agent, or Firm — Sughrue Mion, PLLC

(57) ABSTRACT

The current invention refers to the procedure to obtain compositions rich in omega 3 fatty acids with content in phytanic acid below 90 μg per gram of oil. The current invention also refers to the obtaining of compositions rich in DHA with a content in phytanic acid below 90 μg per gram of oil, more specifically between 650-950 mg/g, that is, between 65% and 95% of DHA in weight and values of PhA below 90 μg, preferably below 5 μg per gram of the oil forming the composition. The compositions obtained are used in the field of food supplements, nutritional products and pharmaceutical products due to their prophylactic action and therapeutic effect.

25 Claims, 6 Drawing Sheets

(56) References Cited

OTHER PUBLICATIONS

Macsai, M., The role of omega-3 dietary supplementation in blepharitis and meibomian gland dysfunction, 2008, Trans. AM Ophthalmol Sco. vol. 106, pp. 336-356.*

Rashid, S. et al., Topical omega-3 and omega-6 fatty acids for treatment of dry eye, 2008, Arch Ophthalmol, vol. 126, No. 2, pp. 219-225.*

Steenhuysen, J., Omega-3 no match for Alzheimer's, study finds, 2009, Reuters, 1 page.*

Scar[omo. E. et al., Treatment of alzheimer's disease: current status and new perspectives, 2003, The Lancet Neurology, vol. 2, pp. 539-547.*

NHS, Dry eye syndrome—Information prescription, 2014, NHS, United Kingdom, 10 pagea.*

Verhoeven, N.M., et al., The metabolism of phytanic acid and pristanic acid in man: a review, 1998, J. Inher. Metab. Dis., vol. 21, pp. 697-728.*

* cited by examiner

| Cell cultures | µg/ml PhA | % apoptosis/ dish | % Bcl-2 (+) | % Bax (+) | Ratio Bcl-2/ Bax |
|---|---|---|---|---|---|
| Control DHA (−) Paraquat (−) | 0 | 31.4±4.2 | 42.1±3.6 | 2.1±0.3 | 20.0 |
| Control DHA (−) Paraquat (+) | 0 | 74.4±8.1 | 36.8±6.1 | 12.4±1.1 | 3.0 |
| DHA(+)$_0$ | 0 | 34.2±2.3 | 62.4±3.5 | 2.5±0.6 | 25.0 |
| DHA(+)$_1$ | 4 | 35.3±1.9 | 60.9±2.2 | 2.3±0.2 | 26.5 |
| DHA(+)$_2$ | 20 | 42.2±4.6 | 63.6±1.4 | 2.6±0.7 | 24.5 |
| DHA(+)$_3$ | 100 | 51.1±6.4 | 54.5±4.1 | 3.3±1.0 | 16.4 |
| DHA(+)$_4$ | 500 | 61.7±7.5* | 48.3±3.7 | 4.5±0.9 | 10.7 |
| DHA(+)$_5$ | 2500 | 73.3±5.8 | 42.4±4.2 | 6.7±1.4 | 6.3 |
| DHA(+)$_6$ | 12500 | 82.6±7.7 | 38.4±7.1 | 14.7±2.7 | 2.6 |

| Retins of Albino Mice | μg/ml PhA | % apoptosis/ dish | % Bcl-2 (+) | % Bax (+) | Ratio Bcl-2/ Bax |
|---|---|---|---|---|---|
| Control DHA (−) MNU (+) | 0 | 84.4±5.3 | 31.3±4.3 | 17.1±2.7 | 3.0 |
| DHA(+)$_0$ | 0 | 31.2±2.3 | 71.1±6.2 | 1.9±0.3 | 37.4 |
| DHA(+)$_1$ | 4 | 29.8±3.9 | 70.4±6.3 | 2.0±0.5 | 35.2 |
| DHA(+)$_2$ | 20 | 35.6±2.9 | 64.2±4.1 | 2.3±0.2 | 27.9 |
| DHA(+)$_3$ | 100 | 43.7±3.4 | 57.6±5.8 | 3.1±0.7 | 18.5 |
| DHA(+)$_4$ | 500 | 53.1±5.2 | 46.1±4.9 | 4.3±1.3 | 10.7 |
| DHA(+)$_5$ | 2500 | 62.1±4.6 | 39.8±3.3 | 8.3±1.9 | 4.8 |
| DHA(+)$_6$ | 12500 | 71.6±5.5 | 33.2±5.7 | 13.2±2.5 | 2.5 |

| Date | Reference Values | Average PhA levels in 11 Patients Results μg/ml | | | | | | |
|---|---|---|---|---|---|---|---|---|
| | | T0 | T1 | T2 | T3 | T4 | T5 | T6 |
| Phytanic acid | < 0.20 μg/ml | 35,350 | 4,060 | 6,610 | 4,580 | 2,410 | 2,820 | 1,120 |
| Pristanic Acid | < 0,02 μg/ml | 31,710 | 5,650 | 6,330 | 4,200 | 4,130 | 5,260 | 1,650 |
| C22:0 | 20,97 ± 6,270 | 11,030 | 11,340 | 12,670 | 7,370 | 15,860 | 14,230 | 8,840 |
| C24:0 | 17,59 ± 5,360 | 14,180 | 15,210 | 19,500 | 11,560 | 21,960 | 19,940 | 14,170 |

COMPOSITIONS RICH IN OMEGA-3 FATTY ACIDS WITH A LOW CONTENT IN PHYTANIC ACID

CROSS REFERENCE TO RELATED APPLICATIONS

This application is a National Stage of International Application No. PCT/EP2009/002842 filed on Apr. 17, 2009, the contents of all of which are incorporated herein by reference in their entirety.

TECHNICAL SECTOR OF THE INVENTION

The current invention refers to the procedure to obtain compositions rich in omega 3 fatty acids with content in phytanic acid below 90 µg per gram of oil. The current invention also refers to the obtaining of compositions rich in DHA with a content in phytanic acid below 90 µg per gram of oil, more specifically between 650-950 mg/g, that is, between 65% and 95% of DHA in weight and values of PhA below 94 µg, preferably below 5 µg per gram of the oil forming the composition. The compositions obtained are used in the field of food supplements, nutritional products and pharmaceutical products due to their prophylactic action and therapeutic effect.

BACKGROUND OF THE INVENTION

Omega 3 fatty acids are a family of polyunsaturated fatty acids whose common feature is that the last double bond is located in the third C—C bond starting from the final methyl group of the fatty acid. Omega 3 fatty acids are essential, that is, the human body cannot produce them internally and therefore it is necessary to take them through the diet or through compositions. Due to their polyunsaturated nature, omega 3 fatty acids have very particular physicochemical functions in the human body (ie. very low melting point) and therefore they have been widely studied. Today, it is known that there are up to 10 omega 3 fatty acids (ie. stearic acid), although their presence in the human body is in very small amounts and their physiological activity is very low or absent, except for DHA and/or EPA.

The acid 5,8,11,14,17-eicosapentaenoic or EPA, as well as 4,7,11,13,16,19-docosahexaenoic or DHA are the omega 3 fatty acids with most physiological functions, specially DHA, which has specific functions in retina, sperm, neural tissue etc. Both DHA and EPA have common physiological functions, although DHA has specific physiological functions that no other fatty acid has, particularly in photoreceptors, neural tissue and sperm amongst others. The intake of high doses of DHA increases the levels of EPA, although the reverse does not happen; in addition, DHA does not alter the synthesis of other fatty acids (Voss et al., 1992).

From the physiological perspective, DHA is the most interesting omega 3 fatty acid from the biological viewpoint for human consumption. Since DHA and EPA are present in the same food sources and since EPA is more abundant, initially EPA has been the one that has called more attention, being easier to obtain. However, knowledge on these two fatty acids over the last 15 years has significantly increased the interest for DHA and for its necessary purification since, aside from exceptions, at the most it is present in no more than 10-15% of the fats in the most abundant food sources.

The majority of sources for obtaining omega 3 fatty acids rich in DHA are of marine origin: microalgae (ie. *Schizochytrium* sp., *Crypthecodinium* sp., *Ulkenia* sp., *Euglena* sp.), crustaceans (ie. krill *Euphausia superba*), fatty fish (ie. *Thunnus ibynnus thynnus* or red tunna), and marine mammals; in addition to mushrooms and yeast (ie. *Yarrowia lipolytica*) and bacterias (ie. *Lactobacillus* spp.).

The most abundant source with the highest purity and most adequate for obtaining omega 3 fatty acids rich in DHA for human consumption is fish, since the production is of 140 million Tons of fish and shellfish per year (FAO, 2007) and it is estimated that the production of fish oil accounts for 1 million metric tonnes yearly (IFFO, International Fishmeal & Fish oil Organisation). The most suitable fish is tunna and other species with the highest content of Omega 3, being the percentage of DHA beyond 20% in weight; besides, since they are food products they exhibit the highest guarantee and safety in public health. On the other hand, together with fish, krill represents the largest reserve and biomass of DHA of the planet. However, the exploitation of krill to obtain omega 3 fatty acids represents a serious and known risk for trophic chains and the development of species and fish necessary for the human diet. A possibility in the future would be obtaining such krill in krill farms, where there would be no risk for the trophic chains and in addition, they could reproduce in an environment free from contaminants that would normally exist in marine waters.

Numerous authors consider that DHA is a deficient nutrient in most diets worldwide. But, in addition to its relevance as a treatment in DHA deficient diseases, its physiological action makes it into the most relevant cofactor for the treatment and prevention of neurodegenerative disease such as Alzheimer or schizophrenia; retina degenerative diseases, cancer, autoimmune diseases, chronic articular and dermatologic inflammatory diseases, renal and urologic diseases (prostate), androgenic alopecia, alterations in male and female fertility, primary attention disorder or hyperactivity, intellectual and cognitive development, as well as necessary for the visual development and particularly of the macular region, cardiovascular diseases, diabetes and hypertriglyceridemia.

For the treatment of numerous pathologies, it is necessary to use doses tens of times higher to those obtained just with the diet (generally >2-4 grams), which makes it necessary to obtain DHA compositions with high purities in order to achieve the consumption of adequate doses (ie. to obtain a dose of 4 grams of DHA from 20% oil compositions, it would be necessary to take 20 grams of oil or 40 conventional soft gels of 500 mg).

Polyunsaturated fatty acids are highly unstable in their free form, so their oral uptake requires stabilisation, which can be achieved through esterification or link to other molecules such as glycerol and ethanol, that makes them more stable and increases their bioavailability. The first vehicle (glycerol) enables a higher purity (triglyceride), stability and exhibits a maximum bioavailability, avoiding the presence of alcohol, which is particularly important in cases where high doses are required and when, in numerous applications, its use is chronic, in addition to pregnant women and children. Triglycerides are ingested in concentrations hundreds of times higher as part of the normal food and are the natural nutritional source and pharmacokinetics of fatty acids in target tissues. The pharmacokinetics of triglycerides is maximum and it enables the maximum purity of the active substance, DHA, and therefore DHA triglycerides exhibit the best absorption and have more physiological and metabolic implications.

Parallel to an increased sensitivity towards the connection between food and health, there is an increased acceptance of fish as a healthy nutritional source. Fish is an important source of high quality proteins, minerals and vitamins, in addition to polyunsaturated omega 3 fatty acids, whose benefits for the health are well recognised. However, a recent study highlights the risk associated to environmental contaminants such as mercury and dioxins, which are known to accumulate in fish.

The synthesis of fatty acids and the trophic chain in living organisms are responsible for the physicochemical properties of the membranes and their physiological adaptation to the environmental conditions (ie. temperature). The fatty acids with the lowest fusion point (FP) found in phospholipids and fats of living organisms are pristanic acid (PA), phytanic acid (PhA), EPA, DHA, arachidonic acid (AA) and estearic acid (SDA), which grant optimal physiological conditions under low temperatures. Organisms use two chemical strategies to obtain fatty acids with a very low FP: methylation and the unsaturation of carboxylic acids. Taking into consideration the extreme conditions encountered in organisms of marine origin, it is not surprising that the most rich sources of such fatty acids are mainly in cold marine waters. In this sense, the fatty acids with the lowest FP encountered in nature, foods and in the fatty derived products such as oils of marine origin, are the long branch chain fatty acids (C>18) with several methyl groups, from which PhA is the one present in the highest concentrations and the long chain lineal omega 3 fatty acids (C≥18), where the two most relevant ones due to their concentration and abundance are DHA and EPA.

PhA is present in the human diet or in animal tissues where it can get through the chlorophyll of plants. PhA is formed from the corresponding alcohol, phytol and is oxidised to form PA, which explains why it is usual to find PA and PhA together. PhA is involved in one human pathology, Refsums Syndrome, which is characterised by an accumulation of PhA in the blood and tissues, having discovered subsequently that it is connected with a deficiency in the alpha-oxidation route in the liver.

Whilst the majority of foods contain less than 5 µg of PhA/g, those with the highest content exceed 1 mg of PhA/g, and in the case of fish they exceed 750 µg/g, being its quantity proportional to the percentage of fat. It is considered as the food with the highest concentration of PhA and of higher risk (Group III) for consumption in diseases such as Retinitis Pigmentosa (RP) and defects in the oxidation of PhA such as Refsum's disease. On the other hand, processes for the separation of fats in the production of fish oil, significantly increase the concentration of PhA.

It is known that the fatty fraction from fish is the main source of the omega 3 fatty acids DHA and EPA in the diet, but it is also the main source of PhA. Sources with the highest content in EPA and DHA represent the majority of the intake of DHA and EPA, being associated at the same time with the highest concentrations and intake source of PhA. Both DHA and PhA share the same sources, far beyond products for food and pharmaceutical use, thus finding the highest concentrations of DHA and PhA in products of marine and microbial origin. Normally, PhA is found together with EPA and DHA. Bacteria, fungus and micro-algae are the organisms in nature with the highest concentration of PhA. Oils derived from micro-organisms with a rich content in DHA and the least proportion of PhA, frequently exceed 100 µg/g.

All the western diets studied, including the Mediterranean one, have a daily intake of 100-150 mg of DHA, whilst numerous authors establish a daily need of 200-300 mg. DHA is the only nutrient for which practically all the population worldwide is deficient in their diet.

A very important point which is not usually shown in the literature is that DHA from the diet is 100% of animal origin, since there is no DHA in vegetal food sources (except for some algae which are not used as foods). Therefore, the need in vegetarians is much higher, particularly in strict vegans, where the lowest levels can be found. Its deficiency is even greater and considered by some authors as a marker, in the disease Retinitis Pigmentosa (RP) as well as in metabolic neurodegenerative diseases associated with peroxisomal defects.

Given the widespread interest in the purification of omega 3 fatty acids, mainly DHA, EPA or both, for decades have been numerous patents and regular procedures to obtain refined oils rich in DHA and EPA to obtain higher purities.

However, as shown in FIG. 3, refined and purified oils which exist in the market and that are obtained with patented processes and Good Manufacturing Practice (GMP), contain high levels of PhA, even in those oils with a high DHA purity.

Negative Effects of PhA in Health.

PhA is a risk factor for public health since it induces cancer in prostate, breast, colon . . . as well as neurological and visual disorders (Lloyd-M D et al., 2008; Allen-N E et al., 2008; Thornburg-G et al., 2006; Xu-J et al., 2005). In addition, it is cytotoxic (Komen-J C et al., 2007; Schönfeld et Reiser, 2006; Schönfeld et al., 2006, Heinz, 2005; Elmazar & Nau, 2004). The intake of PhA is a risk factor for the development and/or evolution of diseases: ophthalmologic (retina, cataracts, dry eye . . . ), olphative and auditive alterations, neurologic (Alzheimer, encephalopathy . . . ) and psychiatric alterations, nephrologic alterations, cardiovascular (electrical abnormalities S. Purkinje, alterations of the smooth muscle, ischaemic cardiopathy, atherosclerosis), myopathies and severe amiotrophy, bone alterations, hepatic alterations, alterations of the male and female fertility, chronic autoimmune and inflammatory diseases (Crohn disease, Colitis ulcerosa, LES) and cancer (prostate, colon, breast, kidney, ovary, some types of leukaemia, etc.).

The exact mechanisms by which PhA is toxic for neurosensorial and neural tissues, heart, kidney, liver, intestine, smooth and striated muscle, prostate, breast, sperm, lung and bone system is being gradually elucidated. The most well known mechanisms are connected with the over-expression of tumoral markers (the alpha-methylacil-CoA racemase (AMACAR) or the SPC-2) and the uncoupling protonophoric action of the respiratory electron transport chain in the mitochondria and in the cytoplasmic membranes (ie. phototransducción in retina). At a very low dose, PhA is one of the molecules with the highest induction of oxidative stress in vivo, it potentiates the theratogenesis and is a great inductor of atherosclerosis and death by cardiac failure.

PhA is directly toxic to the mitochondria and exhibits a powerful atherogenic activity. PhA has a rotenon type activity in the uncoupling of complex I in the oxidative phosphorylation in the inner mitochondrial membrane, resulting in the subsequent production of oxygen reactive species and the in vivo lipoperoxidation of DHA and other polyunsaturated fatty acids or PUFA (Kahler-S et al., 2005). It reduces the levels of DHA in phospholipids, mainly in the photoreceptors and neural tissue, increasing the sensibility to ischaemia, to cardiovascular reperfusion lesions and to the oxidation of low density lipoproteins (LDLox), increasing the macrophages anti-inflammatory activity, reducing the energetic and metabolic activity (inhibiting the oxidative phosphorylation) and inducing the mutation of the mitochondrial DNA. This toxic metabolic activity explains by itself why photoreceptors, pigmentary epithelium, neural tissue, heart (Purkinje cells), kidney, liver, ovary, sperm, lungs . . . all of the tissues rich in mitochondria, are the first ones in being affected in patients with high PhA concentrations. PhA induces $Ca^{+2}$ mediated apoptosis in the Purkinje cells (Powers-J. M et Al. 1999) and sudden cardiac death in animal models. PhA produces ischaemia, apoptosis of the vascular smooth muscle, is atherogenic and particularly cardiotoxic. A deficiency in the sterol-2 transport protein (SPC-2) produces sudden cardiac death by accumulation of PhA in mice. PhA induces apoptosis in cell cultures of vascular smooth muscle cells (VSMC) in humans, mice and pigs.

The altered activity of $Ca^{+2}$ reabsorbtion and the apoptosis of osteoclasts due to PhA results in bone abnormalities. Proteins linked to $Ca^{2+}$ in the membranes of the outer segments of photoreceptors, where calmoduline is particularly concentrated, are responsible for the $Ca^{2+}$ flow which controls multiples event in photoreceptors, including phototransduction and synaptic transduction. The calmoduline function is mediated by numerous proteins linked to it including GTPases. When the calmoduline concentration is reduced in photoreceptors, defects occur in the vision, particularly in the adaptation to light and darkness.

PhA is directly toxic to the cilliary ganglionar cells affecting parasympatic ganglionar nerves in the posterior region of the ocular orbit, responsible for pupil contraction and for the vision accommodation (presbyopia, hypermetropy, photosensibiity, etc). PhA interferes with the function of cilliary cells, basal body and proteins linked to microtubules required for the biogenesis of the cillium, mediated by the interaction of the different types of myosin and prenilation of Rab GTPases in the primary cillium of photoreceptors, affecting the transport of essential proteins such as opsine, olphatory cells, cochlea, renal cells, respiratory system, sperm, intestinal microvilli, as well as to the movement of melanosomes in the pigmentary epithelium in retina. RP, which exhibits alterations in the metabolism of PhA, is a model of the alteration of cilliary cells, finding abnormalities of the sperm axonema and of the rods cilliary cells, affecting to the renewal of the outer segments of the rods which depend on the cilliary body, resulting in irreversible visual damage. Also, in RP with non associated syndromes, alterations of the auditive evocated potentials and alterations of the audiometry compatible with cochlear alterations characteristic of cilliary cells are found. Significative alterations of the cilliary body result in RP and deafness in a way which is comparable to Usher and other syndromes such as in patients non associated to syndromes with auditive alterations.

The Rho and Rab family small G-proteins require addition of these isoprenyl moieties at their C termini for normal GTPase function. Rho GTPase signalling pathway are critically needed to target for therapeutic intervention in nephrological diseases, neurological disorders (myelinisation), cancer progression, cardiovascular diseases, infectious diseases, etc. PhA and other isoprenoids impaired Rho-GTPase signalling, particularly Rac pathway, in an opposite way to DHA and statins. The PhA alters Rho-GTPases in a way comparable to some bacterial toxins in the epithelium and digestive and respiratory mucosa to develop the invasive and infectious processes; tumoral processes and metastasis (ie. prostate, breast), renal lesions (glomerular, tubular etc.) and demielinisation.

These GTPases are the main mechanism that explains why DHA without PhA is more efficient than the rest of DHA with PhA in the numerous applications of in the present innovation.

Following this same line, PhA and PA are controllers of the main and most powerful mediators of the angiogenesis and inflammation phenotypes. The induction of angiogenesis, TNFalpha, GBP-1, GBP-2 and inflammatory cytokines (CI) by PhA and PA is a determining factor for the development of cancer (metastasis), autoimmune diseases, inflammatory diseases, infectious diseases, renal, pulmonary and neurological.

PhA becomes PA by oxidation and both PhA and PA, induce apoptosis mediated by the formation of UNAM of the nitric oxide synthase and high concentrations of the protein within 2 hours from the treatment (Idel et al., 2002). Besides, PhA and PA control the main and most powerful mediators of the angiogenesis phenotype and the inflammation. Also, PhA and PA are the most powerful inducers of the activation and secretion of the tumor necrosis factor α (TNFα) (Idel et al., 2002). The expression of the human guanylate-binding protein (GBP)-1 is highly induced by inflammatory cytokines (ICs) and therefore, may characterise IC-activated cells. GBP-1 is a novel cellular activation marker that characterises the IC-activated phenotype of endothelial cells. GBP-1 is a major regulator of the anti-angiogenic response of endothelial cells to ICs. GBP-1 is a cytoplasmic protein and its expression in endothelial cells is selectively induced by interferon-gamma, interleukin-1alpha, interleukin-1beta, or TNF-alpha, but not by other cytokines, chemokines, or growth factors. PhA and PA are inducers of alpha TNF and of interferon gamma. GBP-1 expression is highly associated with vascular endothelial cells but was undetectable in the skin, but it was highly induced in vessels of skin diseases with a high-inflammatory component including psoriasis, adverse drug reactions, and Kaposi's sarcoma. It has been shown that the expression of GBP-1 and of the matrix metalloproteinase-1 (MMP-1) is inversely related in vitro and in vivo, and that GBP-1 selectively inhibits the expression of MMP-1 in endothelial cells, but not the expression of other proteases. The latter finding indicated that the inhibition of capillary formation is specifically due to the repression of MMP-1 expression by GBP-1, and is not affected by the anti-proliferative activity of the helical domain of GBP-1 (Guenzi et al., 2003).

PhA potentiates the theratogenic effects of retinoic acid (Elmazar & Nau, 2004), being particularly relevant, since DHA, which is frequently associated with PhA, is recommended during pregnancy, nursing and in children food.

Retinosis pigmentaria (RP) is an ideal model to study the toxicity of PhA in presence of DHA, as will be seen further along this document. The physicochemical properties of PhA makes it into an important competitor of DHA when becoming incorporated into the position 2 of phospholipids (the usual position of DHA in photoreceptors). PhA has a high number of free rotating bonds (14) and has a very low crystallisation point, enabling a high fluidity in the membrane. However, PhA is lacking the structural conformation characteristic to DHA for the Van der Waals interactions, with the alpha-helix of rhodopsin, necessary for its mobility in the membrane and the tertiary structure. As a consequence, PhA reduces the activity of rhodopsin and of the phototransduction. PhA has the ability to uncouple the photoreceptors membranes resulting in a failure in the phototransduction (continuous hyperpolarisation) found in RP. PhA is not sensitive to the degradation by oxidation and is resistant to dystrophic conditions such as those found in RP. This happens especially in cases of DHA deficiency, such as in RP, consequence of the dystrophy, where it is the single disease where there is a deficiency in DHA, being considered as a marker of the disease.

PhA modifies the function of photoreceptors through its incorporation to the phospholipids and triglycerides, displacing DHA (McColl & Converse, 1995; Powers et al., 1999, Mönning et al., 2004) and reducing the levels of DHA due to the lipoperoxidation and mitochondrial damage induced by PhA. PhA also has the toxic ability to act as a protons transporter (uncoupling agent) not only in mitochondria but in the photoreceptors membranes (Gutknecht-J, 1988), thus altering the polarisation of the outer segments of the photoreceptors.

Displacement of DHA by PhA.

PhA modifies the function of the photoreceptors through its incorporation into the phospholipids and triglycerides, thus displacing DHA from the second carbon of the phospholipids in the ROS membranes and the mitochondria. Therefore, the displacement of DHA from the membranes by PhA alters the function of the photoreceptors, behaving as a DHA antagonist in the phototransduction, altering the calcium homeostasis and the regeneration of rhodopsin. The displacement of DHA by PhA is one of the various mechanisms of action in some diseases (ie. RD=Refsum's Disease) being a partially pathogenic mechanism.

Whilst DHA is an inhibitor of apoptosis as well as a neurotrophic or survival factor for photoreceptors, PhA is one of the most powerful inductors of oxidation and apoptosis in vivo, interfering on an antagonist manner with the action mechanisms of DHA. PhA levels in the oil interfere with the activity of DHA, since capacity of DHA to inhibit apoptosis in retina is reduced by the presence of PhA on a dose dependent manner.

PhA produces apoptosis in photoreceptors in animal models with RP producing an irreversible damage in mitochondria. Under these conditions, the peptides responsible for the survival of photoreceptors are incapable of inhibiting apoptosis. However, DHA is the single fatty acid that neutralises the reactive species in retina under dystrophic conditions. PhA is particularly toxic in dystrophic retinas and DHA reduces its effects. It has been proved that DHA is an inhibitor of oxidative stress and the irreversible mitochondrial damage which causes photoreceptors degeneration (Rotstein et al. 2003).

Therefore, it can be concluded that PhA besides being cytotoxic, is an antagonist of DHA with all the implications involved. Specifically, PhA on an antagonist manner to DHA, induces apoptosis via mitochondria.

In the current invention two preclinical experiments have been developed inducing apoptosis in photoreceptors with Paraquat (FIG. 1) and MNU (FIG. 2), in order to study the anti-apoptosis effect in vitro and in vivo of DHA in connection with the PhA concentration. In both experiments it is demonstrated that the anti-apoptosis capacity of DHA in photoreceptors is inversely correlated to the PhA concentration. The highest anti-apoptosis activity is obtained with concentrations between 0 and 20 µg/g here the ratio Bcl-2/Bax was significantly lower than in mice fed with <5 µg/g.

Toxicity of PhA.

It is not necessary a metabolic alteration or pharmacologic or alimentary interaction of the oxidation of PhA in order to exhibit toxicity, since a nutritional dose of PhA through a conventional diet, also results in significant variations of PhA and an increased risk for health and toxicity. On an schematic way, the toxicity of PhA through its consumption at low doses, is related with the following situations:

1. Within the oxidative process of PhA is included part of the physio-pathological process: the induction of AMACAR. The effect of PhA in health is also determined by the over-expression of certain molecular markers associated to numerous cancers of great epidemiological value: prostate cancer, colorectal cancer and of renal cells. There is evidence that this same marker is connected with ovary, breast and endocrine cancers related with a resistance to insulin. PhA is essential for the survival of several tumor cell lines (prostate, kidney, breast, colon, lung) resulting in the over-expression of AMACAR and SPC-2. Cases have been described with deficiencies in AMACAR with neuropathy, RP and an increase in PhA and PA (Ferdinanduse et al., 2000).

2. Failure in the oxidation of PhA with an increased accumulation of PhA in patients with RP such as in juvenile or adult Refsum's disease, Zellweger syndrome, neonatal adrenoleukodystrophy and rhizomelic punctata chondrodysplasia.

3. However, other genetic diseases exhibit increases in PhA compared to the normal population due to peroxisomal defects such as in: a) Diseases with mitochondriopathies (Complex IV), COX deficiency, Leigh syndrome, Renal Fanconi syndrome (Fingerhut R et al., 1994).

4. More than 50 mg/day of PhA are eliminated via oxidation and cytochrome P450. It is well known that the oxidation of PhA is mediated by cytochrome p450, but it is also known that that there are strong inhibitors of cytochrome P450 (ie. antimicotic azolics, valproic acid, cimetidine, erithromicine, Sulfametoxazol, opioids, cyclosporine, protease inhibitors, antidepressants, hyperphorine, barbiturics, antihistaminics, tamoxifen, cannabioids, S-warfarine, etc.). Thus, certain drugs can increase PhA concentrations on a significant manner. Numerous pharmacological treatments inhibit the metabolic degradation of PhA, accumulating and becoming mainly retinotoxic, neuro- and cardio-toxic. PhA can interact with calcium antagonists, antiangiogenic agents, immunosuppressors and antiinflammatories. The fast oxidation of PhA (alpha-oxidation=90% oxidation of PhA) in the human body is mediated by different isoenzymes of cytochrome P450 (ie. CYP2C8). One the most outstanding drugs, due to its commercial interest and use are the hypolipemiant drugs: fibrates and statins, inhibitors of P450 CYP2C8 which strongly inhibit the oxidative metabolism of PhA, resulting in an accumulation of PhA. Fibrates activate the β-oxidation in peroxisomes, but the degradation of PhA needs the alpha-oxidation which is inhibited by fibrates through the inhibition of cytochrome P450 CYP2C8. PhA is likely to be partly responsible for its main secondary effect: rhabdomyolysis.

5. Secondary failures in the oxidation of PhA: in Alzheimer's disease the activity of the thiamine-dependent enzymes in peroxisomes is reduced, resulting in a reduced amount of the hydroxyphytanoyl-CoA lyase necessary for the oxidation of PhA. Parallel to the increase in the acethylcholine levels found in Alzheimer's disease, an increase in PhA levels has been found.

6. Nutritional alterations (antimetabolites: thiaminases and thiamin antagonists, acetylcholine) that affect the decrease in thiamin, where thiamin pyrophosphate is a cofactor in the oxidation of PhA (via ligases), as well as thiamin deficiencies from which the most well known are those related to the Wernicke-Korsakoff syndrome, the fatal cardiovascular disease beriberi and the neurotoxic syndrome due to consumption of carp and salmonids. Thiamin antagonists are found in substances such as food preservatives (ie. sulphites) from plants and frequent foods (ie. tea, grapes, citrics . . . ), resistant to boiling (ortho- and hydroxiphenols) such as caffeic acid, chlorogenic acid and tannic acid, quercetine and rutine (very used in pharmacology and as food supplements); thiaminases from foods (frequent in fish, mainly from fish farms, 80% of consumption), rumen, diary products and ruminants meat: foods rich in PhA); alcohol consumption, grapefruit juice (and to a lesser extent orange juice, mandarine, apple, grape and their derivates) and caffeine can increase to a lesser extent the deposits of PhA. An interesting model is a genetic disease that produces deficiency of thiamine and neuro-sensorial deafness. Alcohol and pyrithiamin (thiamin antimetabolite) only require 100 µg/ml in order to produce a severe deficiency of thiamin in less than 7 days. These interactions bring to the attention that it is not only important to assess the amount of PhA and phytol contained in food, but that foods associated to the diet, pharmacological treatments, food supplements and habits, can affect the accumulation of PhA from the diet.

7. On the other hand, epidemiological data leave no doubts regarding the toxic effect at doses which are considered normal (50-100 mg/day), being toxic at doses as low as 0.1 µmol/mg fat. Even at much lower concentrations, PhA is one of the molecules with the strongest capacity to induce oxidation in vivo, interacting with some essential physiological mechanisms of DHA and reducing its levels in vivo, damaging its structure through lipoperoxidation. At very low blood concentrations 300 µg/ml or <1 mmol/l (<1% total fatty aids) and approx. 5-10% of the total fatty acids of the nervous tissue, it creates a severe neuropathy and death. In post-mortem toxicity studies associated to the accumulation of PhA (Refsum disease), the highest levels found in just some tissues had reached 8.5% of the total fatty acids[23]. Refsum's disease both in adults and children with a severe accumulation of PhA, is an ideal model to study the toxicity by PhA which includes retinosis pigmentosa, nistagmus, hypotony, ataxy, mental and growth retardation, facial and bone dysmorphies, hepatomegaly and hypocholesterolemia.

DHA and PhA

PhA toxicity is related with diseases and situations where the intake of DHA is recommended and used, such as in retinosis pigmentosa (RP), where DHA behaves as a marker of the disease and PhA is the etiological agent of RP. Diseases which commonly require DHA for their treatment, are induced at the same time by PhA. Besides the oncologic ones, the most evident one of all is RP. The branch chain fatty acids PhA and PA, are markers in different RP diseases (Refsum, Neonatal Adrenoleukodistrophy (NALD), Chondrodysplasia punctata rhizomelic, Zellweger, Usher IV) associated with a defect in the metabolism of the alpha- and beta-oxidation of PA. PhA is the single cause of RP in these cases.

For decades, it has been known that in RP there are deficiencies in DHA in all target tissues. All patients with RP exhibit alterations in the metabolism of DHA and a significant part of them have high concentrations of PhA which, to a certain extent, is the cause of the disease evolution. The degree of DHA deficiency is not associated with the evolution and prognosis of the disease. In this sense, the non systemic dominant autosomic RP is the most benign of all the hereditary forms (PhD Thesis Cela-López, J M), even at DHA levels which where below those taken on an sporadic basis (Schaefer et al. 1995). However, the oral intake of 2 g/day of DHA in patients with XLRP does not normalise the levels of DHA, due to a loss of DHA in dystrophic retinas, being necessary to take 4 g/day in order to normalise the levels of DHA in the erythrocytes phospholipids. The evolution and prognosis of the various types of RP, depends on the pharmacological dose of DHA and of the moment of starting its intake, as well as of the PhA levels. Therefore, it can be said that the concentration of PhA is related with the worse prognosis in the evolution of the disease and in the loss of the central function (macular region).

Increased Levels of Phytanic Acid have been Found in Treatments with "DHA"

Four samples from 4 patients arrived to our laboratory to evaluate the beneficial effect of a treatment with DHA in two syndromes with RP. Treatment with 4 g/day of DHA (4.86 mg phytanic) of four patients with juvenile Refsum disease and Zellweger syndrome during 3 months, increased the presence of branch chain fatty acids: phytanic and pristanic by 50% and 44%. On a parallel way, a complete worsening of the clinical condition was observed: neurological, deafness and RP (visual acuity and visual field). The Peroxisomal Disease Laboratory from the Kennedy Krieger Institute (Baltimore), routinely informs in all the analytical results to all the patients that they study during the year, that intake of DHA from fish increases the toxic levels of phytanic acid and therefore they always recommend DHA from algae. Data show that commercial concentrates of DHA are toxic in patients with RP associated to peroxisomal defects.

In 1994, the Association of RP Patients (AARPE Spain) carried out a study with 17 patients with RP with or without syndromes (Refsum, Zellweger, NADL, Kearns, Bordet-Bield, autosomic recessive RP, and sporadic RP) that had increased levels of phytanic acid in plasma. They all took DHA oil with different amounts of phytanic acid (from 5 mg to 11.5 mg per day) in variable periods of 1 month up to 3 years. They all showed increased levels of phytanic acid from 23% up to 82%, regardless of the fish oil source. After 1 year, the progression of RP was greater than expected in RP patients with non syndromes (11 patients) (VA 8.3% less), although in those with syndromes (6 patients) the loss in visual function was quite valuable. Subsequently, the treatment with DHA rich in phytanic acid was removed and patients were separated into two groups according to plasmatic levels of phytanic acid (moderated levels: 5-30 µg/ml; high levels 30-900 µg/ml). Treatment with 4 g of DHA low in phytanic acid (<90 µg/ml) was introduced and the levels of phytanic acid and the visual function were assessed. In the group with moderate phytanic levels (no associated to syndromes), a progressive reduction of phytanic acid levels was observed which became normal within 12 months (FIG. 4). Parallel, a regression in the progress of the disease was observed with a visual function comparable to that obtained before the beginning of the treatment with DHA rich in phytanic acid.

The Toxicity of PhA is Linked with the Consumption of Sources Rich in DHA and EPA (ie. Tunna) Since it is Present in Oils at Very Low Percentages (Approximately 0.1%).

PhA is found in the human diet or in animal tissues where it can derive from chlorophyll from plant extracts; this is how it can accumulate in animal tissues. PhA is formed from phytol and is oxidised forming pristanic acid (PA). Given the important variations that exist in the fatty diet of the population (vegetarians, ovolactovegetarians, . . . ), variations in PhA blood levels have been found (up to 6.7 times) exclusively related with the consumption of PhA from the conventional diet, where vegetarian diets exhibit up to 10 times less PhA whilst at the same time are extremely deficient in DHA.

Whilst phytanic acid is a risk factor for prostate cancer, DHA is a protective factor for the same type of cancer. Evidence exceeds to the numerous molecular studies and is supported by epidemiological data and numerous pharmacologic studies, some of which are well advanced (Phase II), regarding the role of DHA in combination with other chemotherapeutical drugs (celecoxib, Plaquitaxel) in the prevention and first line treatment of prostate cancer as well as gastric cancer (Ballet et al., 2004; Jones et al., 2007). Also there is sufficient epidemiologic evidence of the role of phytanic acid in the induction of prostate cancer (Walsh, 2005; Xu et al., 2005; Thornburg et al., 2006; Mobley et al., 2003). In addition, there are three separate studies which associate the take up of fatty fish, red meat and dairy products (sources with the highest concentrations of phytanic acid) with prostate cancer.

In the patents field, it is known of documents to purify oils that contain EPA and DHA, such as document U.S. Pat. No. 4,874,629 (1989) which refers to a procedure to treat oils that contain omega 3 fatty acids, such as salmon, pilchards and other fish which contain EPA and DHA and that in essence consists of: a) subject the oil to a vacuum distillation at 30-150° C. during 2-5 hours and putting in contact the oil with an adsorbent selected amongst silica gel and silicic acid to reduce the high boiling temperature and the most volatile polar flavours and other non desired constituents such as polymers, cholesterol, pigments, pesticides ad heavy metals; and b) subsequently recover the oil from the mixture. Later on, the same authors in U.S. Pat. No. 5,023,100 apply the previous procedure in order to produce an edible oil with EPA and DHA, that can be combined with vegetal oil and/or rosemary oil to improve its oxidative stability.

Likewise, document US2008/0268117 A1 describes a method to purify oils that contain EPA and DHA which comprises: (a) add to the oil an aliphatic alcohol of C1-C4, preferably ethanol in an aqueous solution at 60-70%, at a temperature to which the oil and alcohol separate into two phases (round about 10° C.); (b) heating the mixture until the oil and the alcohol become miscible (50-80° C.): (c) cooling down the mixture at a temperature in which the oil and alcohol separate (approx. 10° C.); and (d) recovery of the oil phase. It is specified that such process is especially adequate to prepare oils to be used in foods and pharmaceutical products due to the fact that the aforementioned process, eliminates the organic contaminants such as cholesterol and heavy metals such as mercury. In facts, it mentions that oils prepared on such a way, are especially suitable to prepare an infant formula (U.S. Pat. No. 5,013,569) and compositions for the treatment of rheumatoid arthritis (U.S. Pat. No. 4,843,095).

There are also documents for obtaining EPA and DHA triglycerides, as for example, document ES 2035751 T3 which refers to a procedure to prepare a triglyceride which has at least one long fatty acid C8+ in the molecule, characterised by an interesterification, in the presence of a lipase, the free long chain fatty acid or one of its inferior alkyl esters C1-C4 with a triglyceride which has one or more short chain fatty acids C2-C6 in the molecule and separate by evaporation during the reaction, the short chain free fatty acid or its inferior alkyl ester, and composition in which the polyunsaturated acid is EPA or DHA or a mixture of both. Document GB 2350610 A describes the preparation of DHA from this oil as a triglyceride through a procedure that uses a combination of a transesterification of the triglycerides with an inferior alkylic alcohol, distillation and a selective enzymatic transesterification with an alcoxy alcohol catalysed by lipases that can be immobilised. Also, document US2008/0114181 A1 refers to a method for the esterification of fatty acids into triglycerides with aliphatic alcohols C1-C8. The method uses an acidic ion exchange resin as a catalyser, which comes into contact with the mixture of the reaction which contains a triglyceride that at least has 1% of free fatty acids and an aliphatic alcohol C1-C8, in adequate conditions for the esterification.

Likewise, it is known how to obtain EPA and DHA as ethyl esters, for example in document U.S. Pat. No. 5,679,809, which describes a procedure for obtaining a concentrate of ethyl esters from polyunsaturated fatty acids, preferably EPA and DHA, which consists of mixing the oil which contains the fatty acids with ethanol in the presence of a catalyser to form an ethylic ester of the fatty acid, whose phase is separated mixing it with urea and ethanol, which is then cooled down until a solid phase is created and then, the liquid phase is separated from which a fraction is obtained enriched with the desired polyunsaturated acids. Another document which also uses urea to separate saturated fatty acids and the majority of the mono-unsaturated ones from the rest of fatty acids present in marine animal oils is EP 0347509 A1, which obtains as a final product a mixture of EPA and DHA. Document U.S. Pat. No. 5,734,071 which achieves a product which contains EPA+DHA from a fish oil using a similar method with urea and the ES 2018384 which prepares a composition with EPA and DHA in relative amounts of 1:2 to 2:1, where these fatty acids constitute 75% in weight of the total fatty acids, also with a method that uses concentration by fractioning with urea and molecular distillation and/or extraction with fluid in super-critic conditions or chromatography.

Document ES 2056852 T3 also claims a procedure for the extraction of the ethylic ester of DHA from fish oil, which includes the transesterification of the fish oil with ethanol in presence of sulphuric acid, followed by the extraction of the mixture with hexane, silica gel chromatography, treatment of the residue in acetone cooled down to −40° C., filtration, evaporation of the acetone and molecular distillation in two steps at 0.133 Pa, the first step at 80-100° C. and the second at 105-125° C.

There are a large number of documents that mention the use of DHA for various states of need and diseases previously mentioned. As an example, we will mention document CN 1557453 (A) which describes a composition to increase memory and improve knowledge which comprises the serrate herb clubmoss, rhodiola root and a fish oil concentrate with 50 mg de DHA as an active substance. It specifies that it strengthens the transmission of the information between neuronal synaptic connections, improving the resistance to anoxia, stabilising the structure of the nervous cells and supplying such nerve cells with essential nutritive material.

In addition, DHA has been mentioned in different documents as having beneficial properties for health, for example, as a nutritive substance for the human brain and to revitalise the intelligence (CN 1130040 (A)). In JP 8098659 (A) it is mentioned that DHA, as an ester or phospholipid, has an improved effect against stress. CN 1105205 (A) gives a description of a capsule which contains 11-45% of pure DHA together with calcium, vitamins and starch, to tonify the brain and activate the intelligence. And document ES 2277557 A1 refers to the use of DHA for the manufacture of a pharmaceutical composition geared towards the treatment of the oxidative cellular damage.

In the state of the art, documents can be found to selectively separate and purify EPA and DHA. Thus, document EP 1065196 A1 refers to a process to selectively separate and purify EPA or DHA or their esters from a mixture of acids or esters which comprises: (a) passing an aqueous fluid with a silver salt through a column with diatom earth, so that the silver salt adheres to the diatom earth; (b) pass through the column with diatom earth and silver salt, a solution with solvents of a mixture containing the fatty acids highly unsaturated or its derivates; and (c) passing a solvent to separate the desired fatty acids.

Document U.S. Pat. No. 6,846,942 B2 refers to a method for the preparation of pure EPA and DHA which comprises: a) dissolving the mixture of DHA and EPA in acetone and adding magnesium ions, which produces EPA and DHA salts which have different solubility in acetone, b) cool down the solution obtained in (a) to precipitate the EPA salt, c) filter the precipitated EPA salt, and d) acidify the precipitate obtained to obtain pure EPA, and e) evaporate the solvent from the filtrate to obtain pure DHA. When the EPA and DHA mixture is obtained from a fish oil, this is firstly subjected to an alcoholysis or saponification in order to transform the triglycerides into free acids.

Therefore, there is still a need for a composition that should not only be beneficial for the diet and health due to the presence of DHA in effective amounts for health, that is, in high amounts of DHA, but at the same time it should contain the least possible amount of PhA in order to prevent its effects when taking in DHA.

OBJECT OF THE INVENTION

Thus, a first object of the present invention a process to obtain a composition rich in omega 3 fatty acids from an oil of marine origin, with PhA levels below 90 µg/g, wherein the mentioned procedure comprises the following steps:
  a) an oil of marine origin is saponified in order to obtain fatty acids salts.
  b) the fatty acid salts from step a) are acidified in order to obtain acidified oil.
  c) the acidified oil from step b) is subjected to ultracentrifugation in a glycerol gradient at a temperature of 10° C. under vacuum (27 Pa).
  d) the glycerol gradient from step c) is subjected to crystallisation to a temperature range between 0 and −57° C. obtaining a solid phase and a liquid phase, where the solid phase contains saturated fatty acids, monounsaturated fatty acids and PhA and the liquid phase contains polyunsaturated omega 3 fatty acids with a PhA content below 90 µg/g
  e) the liquid phase from step d) is separated from the solid phase for its recovery through decantation.

Additionally, the procedure comprises a further step in which the omega 3 fatty acids are esterified to obtain omega 3 triglycerides with a PhA content below 90 µg/g.

The saponification step a of the present object of the invention, is carried out in a preferred embodiment with KOH, water and ethanol, shaking the mixture at a temperature of 40° C. at 300 rpm during 1 hour in a inert atmosphere. In another preferred embodiment, the acidification step b) is carried out mixing the fatty acid salts obtained in step (a) with acetic acid at 70% in an inert atmosphere at 200 rpm.

If the ultracentrifugation of step c is isopicnic, this implies that the centrifugation conditions used should be 100000 g during 42 hours. If the ultracentrifugation is according to density gradient without equilibrium, then the centrifugation conditions should be 100000 g during 24 hours.

In another preferred embodiment, if the ultracentrifugation step is isopicnic, the cristallisation step is carried out at a temperature of 0° C.

In another preferred embodiment, if the ultracentrifugation step is isopicnic, the cristallisation step is carried out at a temperature of −30° C.

In another preferred embodiment, if the ultracentrifugation step is in density gradient without equilibrium, the cristallisation step is carried out at a temperature of −30° C.

A second object of invention comprises a composition, obtained following the procedure described in the first invention, of omega 3 fatty acids in a range of 65% to 99% in weight, with a PhA content below 90 µg/g, preferably with a content in omega 3 fatty acids in a range of 75% to 99% in weight, more preferably where the omega 3 fatty acids represent at least 90% of the weight.

In a preferred embodiment the composition, obtained according to the procedure described in the first invention, comprises omega 3 fatty acids in a range of 65% to 99% in weight, with a PhA content below 5 µg/g, preferably with a content in omega 3 fatty acids in a range of 75% to 99% in weight, more preferably where the omega 3 fatty acids account for at least 90% of the weight.

In another preferred embodiment the composition obtained according to the procedure described in the first invention, the omega 3 fatty acids comprise DHA at a range between 65% to 95% in weight, with a PhA content below 90 µg/g, preferably with a DHA content of 75% to 95% in weight, more preferably with a DHA content of at least 80% in weight.

In another preferred embodiment the composition obtained according to the procedure described in the first invention, the omega 3 fatty acids comprise DHA at a range of 65% to 95% in weight with a PhA content below 5 µg/g de PhA, preferably with a DHA content of 75% to 95% in weight, more preferably with a DHA content of at least 80% weight.

In another preferred embodiment the omega 3 fatty acids composition obtained, according to the procedure described in the first invention, additionally comprise EPA in a range of 5 to 35% in weight.

In another preferred embodiment the omega 3 fatty acids comprising DHA composition obtained, according to the procedure described in the first invention, additionally comprises EPA in a range of 5 to 35% in weight.

In a preferred embodiment, in the composition obtained according to the procedure described in the first invention, the percentage in weight of DHA is of 80.65% and the percentage in weight of EPA is of 13.38%, being the percentage in total weight of fatty acids in the mentioned composition of 91.75%.

In a preferred embodiment, the composition obtained according to the procedure described in the first invention additionally comprises cofactors, extracts and/or active substances for pharmaceutical or alimentary use.

In a preferred embodiment, the composition obtained according to the procedure described in the first invention additionally comprises excipients and/or adyuvants intended for pharmaceutical or alimentary use.

A third object of invention refers to a nutritional supplement which comprises the compositions described in the second object of the invention on a drinkable format, soft or hard gels, aqueous emulsion or powder.

A fourth object of invention refers to a food product which comprises the compositions described in the second object of invention on a drinkable format, soft or hard gels, aqueous emulsion or powder.

A fifth object of the invention relates to a pharmaceutical composition which comprises a compound rich in omega 3 fatty acids according to the second object of the invention or as obtainable by a method according to the first object of the invention or a pharmaceutically diluent or carrier.

Another object of the invention relates to the use of a compound according to the second object of the invention for manufacturing a pharmaceutical composition for the treatment or prevention of allergic condition, eye surface diseases and dry eye preferably selected from the group consisting of blepharitis, blepharoconjunctivitis, conjunctivitis, keratitis, dry keratoconjunctivitis, corneal diseases, treatment against corneal transplant rejection, increase of the average cellular corneal density through pachymetry in pre- and post-Lasik surgery.

Another object of the invention relates to the use of a compound according to the second object of the invention for manufacturing a pharmaceutical composition for the treatment or prevention of retina degenerative diseases non associated with genetic dystrophies, preferably selected from the group consisting of humid or dry macular degeneration associated to age degeneration, diabetic retinopathy, glaucoma, intraocular pressure alterations, retinopathy associated to myopia, retinal detachment, rhegmatogenous retinal detachment in myopic eyes after LASIK, secondary macular oedema of ischaemic origin, cystoid macular oedema or Irvine-Gass syndrome, Berlin Scotome, Choroidosis, Chorioretinitis, Syphilitic Neuroretinitis, Rubeola, Cytomegalovirus, Malign melanoma of coroids, mercury poisons (Minamata disease, Acrodynia, Hunter-Russell syndrome), Retinal vasculitis (Eales' disease), haemorrhagic traumatic retinoschisis.

Another object of the invention relates to the use of a compound according to the second object of the invention for manufacturing a pharmaceutical composition for the treatment or prevention of hereditary retina dystrophies non retinitis pigmentosa preferably selected from the group consisting of Stargardt disease, X-linked Choroideremia, Leber's congenital amaurosis, X-linked retinoschisis, Goldman-Favre viteoretinal dystrophy. Wagner's vitreoretinal dystrophy, and Stickler's syndrome, Familial Pars Planitis.

Another object of the invention relates to the use of a compound according to the second object of the invention for manufacturing a pharmaceutical composition for the treatment or prevention of Retinosis Pigmentosa.

A ninth object of the invention relates to the use of a compound according to the second object of the invention for manufacturing a pharmaceutical composition for the treatment or prevention of Retinosis Pigmentosa related syndromes.

In a preferred embodiment the treated retinal dystrophies are non syndromic RP with as a result of specific mutations and/or failure in the hepatic synthesis or transport of DHA or as consequence of metabolic stress and are preferably selected from the group consisting of all Mendelian types of typical non systemic RP such as sectorial, bilateral, unilateral, bilateral, inverse; autosomic dominant RP; autosomic recessive RP; linked to X RP; simple or sporadic RP; vitreoretinal RP; RP punctata albescens; RP without pigment; choroideal atrophy; choroidea girata and/or retinal athrophy; RP with dystrophy of cones and rods; Usher syndrome such as type I, II, III, IV; iatrogenic RP such as NP 207, Thioridazina, CloroKine, HydroxycloroKine, Clorpromacine.

In another preferred embodiment the treated retinal dystrophies are genetic syndromes with peroxisomal defects with RP and/or deficiencies in DHA and increases in PhA and PA that exhibit variable neurologic, cardiovascular, musculoskeletal and dermatologic alterations and are preferably selected from the group comprising: Zellweger syndrome, Infantile Refsum disease, neonatal adrenoleukodystrophy, peroxisomal biogenesis disorder, rhizomelic chondrodysplasia punctata (RCDP), acyl-CoA oxidase deficiencies, bifunctional enzyme deficiencies, Refsum disease, β-oxidation deficiency, Familial ichthyosiform keratoderma (Sjogren-Larsson sindrome). Diseases with mitochondriopathies (Complex IV): COX deficiency, Leigh syndrome.

In another preferred embodiment the treated retinal dystrophies are genetic syndromes with peroxisomal, mitochondrial defects and/or related with RP and related retinal alterations and are preferably selected from the group comprising S. Bassen-kornzweig, S. Batten or lipofuscinosis, hipoprebetalipoproteinemia, S. Usher, S. Hallervorden-Spatz, Aceruloplasminemia, S. Kearns-Sayre, Duchenne and Becker muscular distrophy, S. Lawrence-Moon-Bardet-Biedl, S. Lawrence-Moon, S Bardet-Biedl, S. Grafe, Leber's congenital amaurosis, S. Hallgreen, S. Cokayne, S. Alstrom, S Pelizaeus-Merzbacher, Cerebelous Ataxy, Friederich Atax, Lipofuscinosis (familiar maurotic idiopatic: Tay-Sachs or Haltia-Santavuori, Biel-Schowsky-Jansky, E. Vogt-Spielmeyer-Batten-Mayou, Enfermedad de Kufs), Osteo-neuro-endocrine Dysplasia, Mucopolisacaridosis (S Hurler, S Hunter, S Scheire, MPS I-H/S, Sanfilippo), S Bassen Kornzweig, balck retinal dysplasia, Skeletal Dysplasia, S. renal-ocular-skeletal, S Edwards, S. Oculocerebrorenal linked to X recessive or S. Lowe, Lignac-Fanconi syndrome (cystinosis), Ggan axonal neuropathy, Familiar Danish Dementia etc.

Another object of the invention relates to the use of a compound according to the second object of the invention for manufacturing a pharmaceutical composition for the treatment or prevention of uveitis and diseases related, preferably selected from the group consisting of iritis; Pars planitis; choroiditis; chorioretinitis; anterior and/or posterior uveitis; iridocyclochoroiditis; infectious uveitis such as Brucellosis, Herpes simplex, Herpes zoster, Leptospirosis, Lyme disease, presumed ocular hystoplasmosis syndrome, syphilis, Toxocariasis, Toxoplasmosis, Tuberculosis, Candidiasis; uveitis syndromes such as acute posterior multifocal placoid pigment epitheliopathy, Birdshot retinochoroidopathy, Fuchs heterochromic iridocyclitis, Multifocal Choroiditis and Panuveitis Syndrome, multiple evanescent white dot syndrome, punctuate inner choroidopathy, serpiginous chroiditis; systemic disorders associated with uveitis such as ankylosing spondylitis, Behcet's disease, chronic granulomatous disease, enthesitis, inflammatory bowel disease, juvenile rheumatoid disease, rheumatoid arthritis, multiple sclerosis, poliarteritis nodosa, psoriasic arthritis, Reiter's syndrome, sarcoidosis, systemic lupus erythematous, Vogt-Koyanagi-Harada syndrome, Whipple disease; masquerade syndromes in anterior and/or posterior segments such as retinoblastoma, retinal detachment, malignant melanoma, leukemia, juvenile xanthogranuloma, intraocular forein body, lymphoma, multiple sclerosis, reticulum cell sarcoma.

Another object of the invention relates to the use of a compound according to the second object of the invention for manufacturing a pharmaceutical composition for the treatment or prevention of retina degenerative disease and secundary ophthalmological conditions related with vascular diseases preferably selected from the group consisting of hypertensive retinopathy; Hypertensive optic ischaemi neuropathy; Hypertensive Choroidopaties such as choroideal sclerosis, branch or central vein thrombosis, Elschnig and Slegrist streaks; atherosclerosis; cerebral and neuro-ophtalmologic ischaemia; aortic arch syndrome; Takayasu disease; Takayasu arteritis; Panarteritis; iridocyclitis; scleritis; preretinal neovascularisation produced by ischaemia and that can result in vitreous haemorrhages; corneal oedema; Tyndall in aqueous humor; proliferative diabetic retinopahty or neovascular glaucoma; carotid insufficiency or chronic ocular ischaemia; obstruction of the ophtalmic artery; obstruction of the central retinal artery; coagulation disorders such as defficiency of proteins S and C, Panophtalmia retinitis, choroiditis, papilar stasis; retinal haemorrhages such as Roth stain, lesions due to immunocomplexes, Optic neuropathy; ischaemic retinopathy; ophthalmoplegia, orbitary pseudotumor; ocular ischaemic syndrome; occipital lobe infarction; dyplopia; palpebral oedema; palpebral ptosis; telangiectasies eye lids; conjunctiva; retinal; acute obstruction of the central retinal artery; ophthalmic or of its branches; obstruction of the posterior cilliary arteries such as Optic-ischaemic neuropathy of non arteritic origin, chronic ocular ischaemic syndrome produced by hyperfusion and blurred vision or Shy-Drager syndrome.

Another object of the invention relates to the use of a compound according to the second object of the invention for manufacturing a pharmaceutical composition for the treatment or prevention of loss of visual acuity non associated to retinal and other ophthalmologic uses preferably selected from the group consisting of cataract, vitritis, vitreous detachment, endophthalmitis, hipermetropy, myopia, and/or presbyopia.

Another object of the invention relates to the use of a compound according to the second object of the invention for manufacturing a pharmaceutical composition for the treatment or prevention of neurological and/or psychiatric disorders particularly neurodegenerative preferably selected from the group consisting of hereditary motor sensory neuropathies, ataxy, spasticity, neuritis, Alzheimer disease, dementia, primary attention deficit, depression, bipolar and schizotypic disorders, multiple sclerosis and/or lateral amyotrophic sclerosis.

Another object of the invention relates to the use of a compound according to the second object of the invention for manufacturing a pharmaceutical composition for the treatment or prevention of oncologic diseases preferably selected from the group consisting of metastasis and the most prevalent tumoral lines, colorectal cancer, prostate cancer, breast cancer, lung cancer, ovary cancer, gastric cancer, esofagic cancer, pancreas cancer, renal cancer, hepatocarcinoma, brain cancer, glioblastoma, melanoma, retinoblastoma, gall bladder, multiple myeloma, endocrine cancers and/or cancers related with a resistance to insulin.

Another object of the invention relates to the use of a compound according to the second object of the invention for manufacturing a pharmaceutical composition for the treatment or prevention of de nephropathies (nephritis and nephrosis) preferably selected from the group consisting of nephropathies by IgA, nephropathy associated to Systemic Lupus Eritematous, renal insufficiency, glomerulopathy, tubulopathy, interstitium and/or renal vascular disease.

Another object of the invention relates to the use of a compound according to the second object of the invention for manufacturing a pharmaceutical composition for the treatment or prevention of cardiovascular diseases, preferably selected from the group consisting of ischaemic alterations, artheriosclerosis, hypertriglyceridemia, hyperlipemias, ventricular arrhythmias, hypertension, diabetes and/or cardiovascular diseases wherein the Apoprotein a (apo (a)) levels are increased.

Another object of the invention relates to the use of a compound according to the second object of the invention for manufacturing a pharmaceutical composition for the treatment or prevention of iatrogenies preferably selected from the group consisting of rhabdomyolysis, hepatotoxicity, cardiotoxicity, neurotoxicity, oedema, lipodistrophy, and/or immunosuppression, associated to statins, corticoids, antiretrovirals and/or immunosuppressors.

Another object of the invention relates to the use of a compound according to the second object of the invention for manufacturing a pharmaceutical composition for manufacturing a pharmaceutical composition for the treatment or prevention of fibromyalgia and/or chronic fatigue syndrome.

Another object of the invention relates to the use of a compound according to the second object of the invention for manufacturing a pharmaceutical composition for the treatment or prevention of arthrosis and osteoporosis Another object of the invention relates to the use of a compound according to the second object of the invention for manufacturing a pharmaceutical composition for the treatment or prevention of autoimmune diseases, chronic inflammatory and skeleton muscular diseases preferably selected form the group consisting of rheumatoid arthritis, juvenile arthritis, Sjogren disease, ankylosing spondylitis, systemic lupus eritematous, arthrosis, osteoporosis.

Another object of the invention relates to the use of a compound according to the second object of the invention for manufacturing a pharmaceutical composition for the treatment or prevention of dermatologic diseases, preferably selected from the group consisting of androgenic alopecia, acne rosacea, acne vulgaris, eczemas and/or psoriasis Another object of the invention relates to the use of a compound according to the second object of the invention for manufacturing a pharmaceutical composition for the treatment or prevention of allergic conditions, asthma and/or chronic respiratory diseases.

Another object of the invention relates to the use of a compound according to the second object of the invention for manufacturing a pharmaceutical composition for the treatment or prevention of digestive system diseases and inflammatory bowel diseases preferably selected form the group consisting of autoimmune, viral and/or toxic, gastritis, esophagitis, Crohn's disease, ulcerative colitis, pseudomembranose colitis, colagenous colitis, alterations of the intestinal permeability, malabsorption syndromes, food intolerance and allergies and/or haemorroids Another object of the invention relates to the use of a compound according to the second object of the invention for manufacturing a pharmaceutical composition for the treatment or prevention of parasitic and infectious diseases.

Another object of the invention relates to the use of a compound according to the second object of the invention for manufacturing a pharmaceutical composition for the treatment or prevention of deficit of DHA. In a preferred embodiment such deficit is due to gastrointestinal malabsorption syndromes selected from the group comprising cystic fibrosis, intestinal malabsorption syndromes, pancreatitis, pancreatic insufficiency and/or cholelithiasis. In another preferred embodiment, the DHA deficit is due to alimentary disorders selected from the group comprising anorexy and/or bulimy. In a third preferred embodiment, the compound of this object of invention relates to compensate the common nutritional DHA deficiency observed in human societies, preferably in the group comprising pregnant women, nursing women and childhood preferably during the first year of life.

Another object of the invention relates to the use of a compound according to the second object of the invention as a cofactor or coadyuvant with other medicines to reduce its secondary effects and/or increase its therapeutic activity when associated with: statins, anti-inflammatory drugs, corticoids, immune supressors, antihypertensive drugs; treatment as hypolipemiant, anti-inflammatory, autoimmune diseases, allergies, treatment against the rejection of transplanted organs and/or antihypertensives.

Another object of the invention relates to the use of a compound according to the second object of the invention to improve physiological conditions increasing the visual acuity, memory and cognitive functions, increasing the sports performance and reducing lesions and/or reducing the normal neuromuscular fatigue.

PhA from tunna has been purified. The graph represents the MP from a sample which contained >96.5% of PhA separated from an oil rich in DHA (>700 mg/g) from tuna, following the procedure of this invention. A DSC has been carried out and two clearly differentiated peaks have been found. In order to do so, it has been crystallised at −50° C. and both phases separated which have been analysed by means GC-MS indicating that they were the two fractions of PhA. The DSC technique is repeated once more and on a pure way it is seen a single peak at −45° C. and −65° C. for each of the phases separated. Through crystallography it is verified and checked that the isomer PhA(3S) has a MP at −45° C. and PhA(3R) has a MP at −65° C.

On this way, by means of DSC an easy method has been developed to carry out a quantitative analysis of the two isomers of PhA. This makes it possible to verify that the isomer PhA (3S) can be evaluated for the selection of the most efficient separation of PhA in this invention. Without ruling out other procedures in the future for the separation of PhA from different samples of oil rich in DHA and omega-3.

As described in this invention, the two isomers show different physiopathological activities in human health. The determination of the isomers through this analysis would be an epidemiological, clinical and nutritional marker of great significance to determine the activity of other molecular markers such as AMACAR (associated to 3S and not to 3R) in cancer vs the toxicity from predominant (3R).

Figure 6:
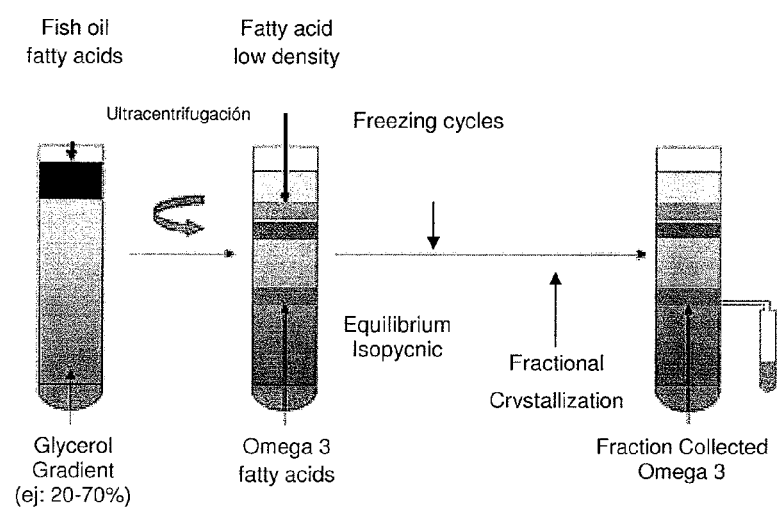

FIG. 6. Fractional Crystallization by Density (FCD): Fractioning in a density equilibrium gradient or isopicnic of a crude oil rich in omega-3. Fraction (a) green colour, fraction (b) blue colour and fraction (c) orange colour.

The diagram represents the formation of the fatty acid fractions produced when the oil is exposed to an isopicnic centrifugation. Omega 3 fatty acids (fraction c) which correspond to the largest density in the oil used in the starting point, become fractioned in the furthest part of the rotor axis, whilst fractions a and b with lower densities and closer to the rotor axis. The cristallysation of the gradient and of fractions a and b enable separating the liquid phase, where the omega 3 fatty acids remain in fraction c.

DETAILED DESCRIPTION OF THE INVENTION

The present invention relates to a method for obtaining rich omega-3 fatty acids containing phytanic acid in levels lower than 90 μg per gram of oil. Specifically, the subject invention provides a method for separating process of the omega-3 fatty acids present on marine animals, microorganisms and algae through a temperature gradient, cooling the extracts until forming a solid-phase which concentrates PhA and saturated and monounsaturated fatty acids, and a liquid-phase, which concentrates omega-3 fatty acids, preferably DHA, essentially PhA free. The described process can be used for obtaining and purifying any highly unsaturated fatty acids existing in nature.

It is convenient that the oil used for obtaining of omega-3 fatty acids, preferably DHA, substantially PhA free, be as fresh as possible so to avoid a probable fatty acids degradation or oxidation. Most fish (essentially oily fish), unicellular algae cultures and Krill are initially considered to be the main sources of omega-3. Nevertheless, omega-3 can also be obtained from other marine sources (i.e.: tuna, cod, salmon, sardine, red fish, whale, seal, shark, non-unicellular algae, etc.), bacterial sources and fungus. The most valuable sources are those of microbial origin (obtained from controlled cultures and fermenters), which contain higher levels of PhA and isoprenoids, along with marine sources. Some species not yet used (i.e: Diatomea algae) would raise great interest as PhA producers, as cod liver oil would do as a source of pristane. In the future, we could use oil from genetically modified animal, vegetal, microbial and/or fungal species as source substances fort increasing omega-3 production, especially DHA. PhA levels are high both in farmed and wild fish.

The procedure, subject matter of the invention, consists of several phases, although some of them are optional:

1. Preliminary Refine (Optional):

The aim of this phase is the elimination of unsaponifiable fats. It is exclusively applicable to raw primary materials, non-refined, such as raw fish oil.

2. Triglycerides and Esters Hydrolysis:

The aim of this phase is to allow the process for obtaining free fatty acids from oil.

Hydrolysis can be: a) saponification+Acidolysis or b) Hydrolysis by lipase

The saponification process will form fatty acid salts. Acidification will form a phase of non-polar free fatty acids (acidified oil), and a polar phase of salts that will be eliminated opening the base of the reactor.

3. Centrifugation (Isopycnic or Non-Isopycnic):

The acidified oil obtained in the previous phase is subjected to ultracentrifugation by glycerol gradient in this stage. Centrifugation may be isopycnic or by non-equilibrium density-gradient.

When centrifugation is isopycnic, a fractional crystallization by density-gradient using a glycerol gradient, is carried out, leading to equilibrium.

If after centrifugation temperature is dramatically reduced, in a glycerol gradient, at 0° C., three fractions are obtained: two solids—one with saturated fatty acids; the second, with unsaturated fatty acids and PhA, which are eliminated; and a third liquid fraction with polyunsaturated fatty acids, containing between 65-99% of omega-3 acids and 65-85% DHA levels, with less than 90 µg/g of PhA.

Temperature can be reduced to −30° C. for 24 h, using a glycerol gradient, obtaining two phases as a result: a solid phase, containing saturated and monounsaturated fatty acids, PhA and the glycerol gradient; and a liquid phase, containing polyunsaturated fatty acids with 65-99% omega-3 fatty acids levels, with 65-85% DHA levels containing less than 5 µg/g of PhA.

If centrifugation is non-isopycnic, temperature should be reduced dramatically to −30° C. the glycerol gradient, when two fractions are generated: a solid fraction, containing saturated and monounsaturated fatty acids and PhA, and a liquid fraction, containing polyunsaturated fatty acids with 65-99% omega-3 fatty acids levels, with 65-85% DHA levels containing less than 90 µg/g of PhA.

4. Esterification of Free Fatty Acids:

The aim is to stabilise free fatty acids as esters and ethylesters, or as triglycerides (which would be a first final product)

In oil purification processes, PhA is not separated—unless a specific phase is stablished for that aim-, since physicochemical properties of PhA (C20) are comparable to long-chain omega-3 fatty acids (C≥18): PF, melting point, saponification value, iodine index, solubility in water and other solvents, polarity to solvents, optical rotation, etc. As a comparison study, DHA and PhA share the same number of H (2) bonds acceptor and donors (1), free rotation bonds (14), polar surface area (26.3 $Å^2$), water solubility at 25° C. (0.001) and comparative molar volume (347.0 vs 354.8 cm3), molecular weight (328.49 vs 312.53), enthalpy of vaporization (77.28 vs 74.2 kj/mol), polarizability (41.97 $10^{-24}$ vs 38.09 $10^{-24}$), refractive index (1.52 vs 1.454). PhA, PA, EPA, DHA, SDA have the lowest PF among all fatty acids, which is between −40° C. y−80° C.

Elimination of products of saponification and elimination of stearin in saturated fats based on saponification and reduction of saturated fatty acids using urea complexes increases the concentration of PhA in the rich in omega-3 fraction. In refined fish oils, all analysed cases revealed an increase of concentration of PhA (>0.1%), and just in certain procedures obtaining a high purity of DHA (>700 mg/g), the aforesaid increase in the initial refining and purifying procedures is reduced (<0.1%) (FIG. 3) It implies that all refining and purifying procedures carried out with fish oil (i.e.: with a maximum DHA <200 mg/g), PhA is not eliminated and, on the contrary, the increase of concentration levels of omega-3 produces a proportional increase of PhA, given the fact that PhA has a physicochemical behaviour highly comparable to that found in omega-3, which is not the case when comparing it to the rest of saturated fatty acids.

Formation of urea complexes and the methodological variations on crystallization of these complexes are under patent (WO1995/011216) and optimised due to its great application in industry, and are widely used in fish oil purification processes. It has been proven that the ethanol-urea reaction in the formation of urea complexes in these procedures causes the formation of ethyl-carbamate or urethan (EC) and its presence in purified oils. Urethan, discovered more than 150 years ago, is a known carcinogen agent and is under investigation by the FDA (Food and Drug Administration), being part of an environmentally dangerous substances list since 1980 (CERCLA), as stated by FDA members Canas and Yurawecz in the editorial. Thus, this invention provides improved results of current deodorization and purification processes, avoiding the frequent but undesirable use of processes in the industry such as deodorization (high temperatures), and purification and refining processes with urea, which are obviously inadequate and not recommended for PhA elimination.

Cooling refining and purification processes under patent are normally used at temperatures over −5° C., and in some occasions it has been carried out at temperatures down to −20° C. Nevertheless, such an useful procedure for separating saturated fatty acids is not applicable to PhA, since it would concentrate in the omega-3 fraction, as EPA, DHA, PhA and PA have a PF at approx. −54° C., −43° C., −65° C. and −80° C., respectively.

PhA and PA are part of the triglycerides found in fish oil comparable to omega-3 fatty acids. Nowadays, enzymatic hydrolysis processes are frequently used; it is selective esterification that concentrates omega-3 fatty acids and particularly DHA. Long time ago it was demonstrated that in all the biology of PhA, it has tendency to position on the 2nd carbon of triglycerides and phospholipids, as found in DHA and other PUFAs; it is also know that PhA and DHA and other omega-3 share the same resistance to saponification and enzymatic hydrolysis. Pancreatic lipase hydrolyses short-chain fatty acids faster than long-chain ones, while PhA, PA, DHA EPA acts very slowly, being resistant to lipolysis (Brockerhoff, 1970; Ellingboe & Steinberg, 1972). Such resistance is comparable to that found on DHA and PhA (Nus et al, 2006), due to the comparable stearic effects of PhA, PA, DHA and EPA (Faber, 2004 y Bottino-N R et al., 1967). What is more, the use of enzymatic processes could, as other processes do, increase levels of PhA. Processes such as complete hydrolysis and nonspecific lipase are as efficient as saponification and catalysed hydrolysis with solids, without altering PhA levels.

For these reasons, there are no processes that separate PhA in oils with omega-3 and DHA without a altering oil composition or through refining processes, needing so a specific process for separating PhA.

Figure 3:
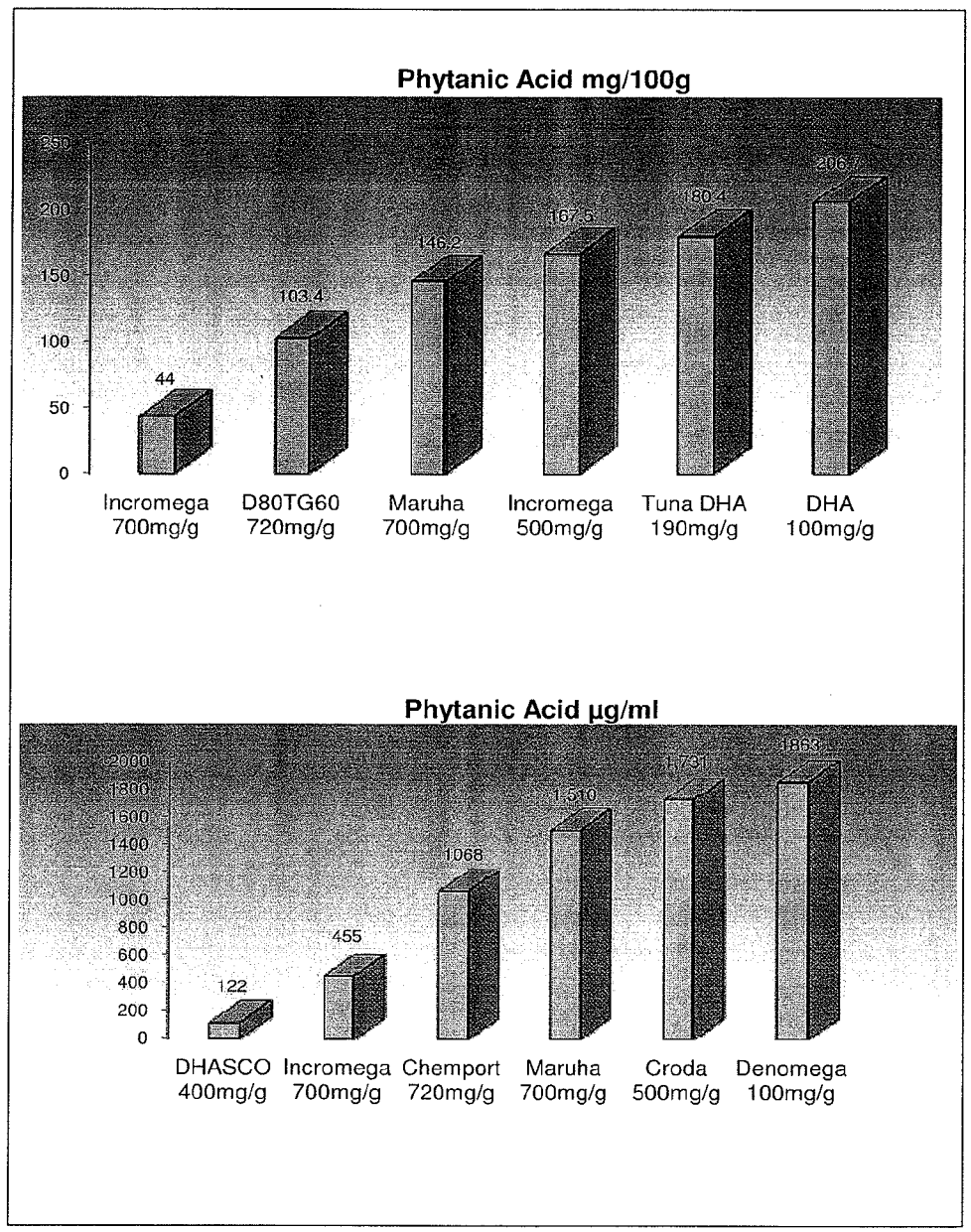
FIG. 3. This figure represents the main companies and products of the market, as well as those found with the lowest levels of PhA of the market when the study was carried out. Their quality and processes are guaranteed for the majority of manufacturers, fulfilling alimentary and pharmaceutical GMP's in accordance with the European Pharmacopoeia and the FDA, being expressly approved for alimentary use. They are the object of patents and are being systematically studied in human research. It can be seen, that the commercial oils at different purities of DHA, contain high levels of PhA and significantly different regardless of the purity of DHA.
Figure 4:
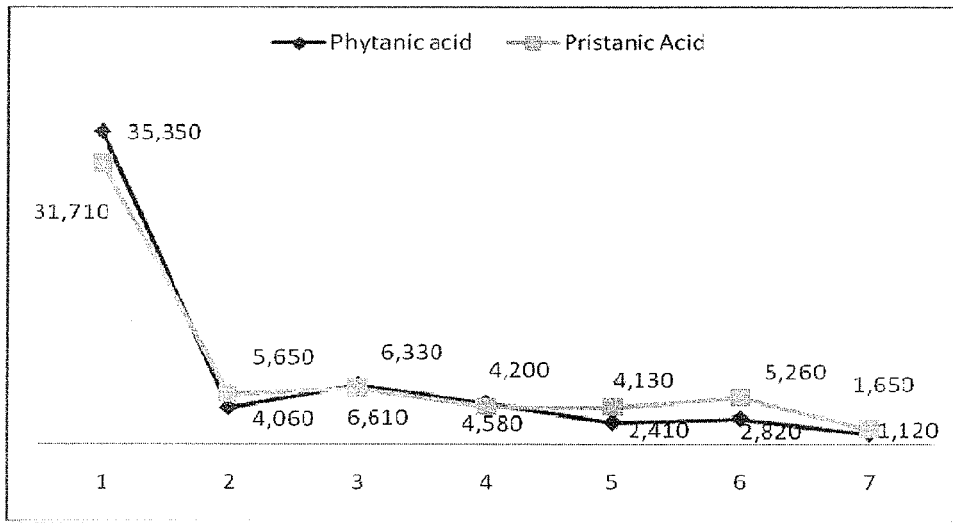
FIG. 4. Reduction of the levels of PhA in patients without syndromes with DHA <5 μg/ml. This figure shows the evolution of 11 patients with RP without associated syndromes with DHA containing PhA <5 μg/g previously treated with DHA containing PhA ≥5 μg/g. In this figure, it can be seen that patients with RP who had DHA with levels of PhA ≥5 μg/g increased their levels of PhA (T0), showing a significant reduction of the PhA levels when taking DHA with PhA <5 μg/g. This demonstrates that DHA with PhA <5 μg/g is safe as a treatment in patients with RP.

FIG. 3 shows that methods for obtaining substantially pure DHA (>700 mg/g) result in variations that are not efficient for the purpose of this invention. Chromatographic methods are probably the best option, and although it is not specific for separating PhA, it is indeed for obtaining substantially pure DHA. A priori, industrial separating methods by chromatography are not sensitive enough to separate PhA and PA at reasonable costs, finding levels out of the required range for this invention, as it occurs in molecular distillation, having the same time, higher risk of having increased levels of benzo(a) pyrene, due to the use of high temperatures. The most outstanding chromatographic methods (i.e.: SFC) are based on polarity and stearic effects. Strength absorption depends not only on polarity, washing time and molecular functional group characteristics, but also on stearic factors. As stated before, PhA and DHA have stearic functions, molecular weight, etc. more proximate to DHA than EPA and other fatty acids. Given the low concentration of PhA and taking into account that in all purity processes of DHA the EPA also increases in a considerable way, it is hardly surprising to find analysis that reveal that PhA is inadequately present too and where, in some cases, its presence reaches elevated levels in all tuna oils, containing 700 mg/g and frequently finding levels of 400 mg/g, while other processes under patent levels higher than 1500 µg/g (>0.1%) can be found, which denotes a higher PhA level than the one found in raw fish (tuna).

Given the low concentration of PhA (<0.1%) found in conventional studies of chromatography analytical grade, PhA and PA are not determined. For that aim it is necessary to adapt chromatography techniques (GC) at a much higher level of sensitivity for the specific detection of PhA.

Given the physicochemical characteristics of PhA and DHA, it would be necessary to adapt the technique to very high purity levels at a very expensive cost in order to reduce PhA. From this approach and without the cost and the industrial technology required, DHA has been purified from fish oils (specifically from tuna, since it presents the highest concentration levels of DHA) from laboratory chromatography techniques and from molecular distillation, until obtaining 830 mg/g, whereas an arithmetic mean of 57 µg/g of PhA levels of has been found, showing high variability (+31 µg/g). From that, the specific industrial DHA purification methods are not efficient to eliminate PhA present in fish oils.

There is an indirect relationship between consumption of oil with high-purity levels in DHA and lower PhA consumption, essentially because of the existing geometric fact in taking a higher amount of oil from lower purity oils to obtain the same DHA quantity. Apart from this, high-purity commercial products do not present any reduction on PhA levels. Differences between methods used for refining or purifying DHA and omega-3 fatty acids vary significantly (FIG. 3), although all of them present concentration levels higher than desired.

As far as this invention is concerned, a specific process for separating PhA has been developed, which should be carried out in the initial phases, or refining phase, in order to obtain oil containing all DHA purity levels and/or different omega-3 combinations, obtaining rich DHA and omega-3 oils with very low levels of PhA or even PhA-free (detection limit: 5 µg/ml). Thus, this process can be adapted to all industry processes and to products with different purity levels.

This invention also implies that it is no longer necessary to purify one or more fatty acids, or to alter the natural composition of oil, for obtaining low PhA oil or PhA-free oil. This is highly relevant when using natural mixtures of omega-3 fatty acids for food or health purposes. This is also a profitable method, since deodorization and purification processes on omega-3 fatty acids are no longer necessary, obtaining a less risky alimentary and pharmaceutical grade than methods being carried out at present.

The subject invention refers to a specific method for physically separating the PhA found in any oil containing >5 µgPhA/g and rich in esters of omega-3 fatty acids, for large-scale industrial production of DHA, EPA or other omega-3 fatty acid from sources rich in omega-3, such as fish, algae or other microorganisms with low or zero levels of PhA.

Such method uses crystallization to obtain a change in the physical state of the oil, keeping PhA and PA in liquid state, since these have MP significantly lower than DHA and omega-3 fatty acids, or any other fatty acid.

TABLE 1

References of experimental MP of the most significant fatty acids carried out at atmospheric pressure.

| Common Name | MP | Common Name | MP |
|---|---|---|---|
| Lauric acid (C12) | +44° C. | Methyl-Laurate | +6° C. |
| Myristic acid (C14) | +54° C. | Ethyl-Laurate | +2° C. |
| Palmitic acid (C16) | +62° C. | Methyl-Palmitate | +35° C. |
| Stearic acid (C18) | +69° C. | Ethyl-Palmitate | +25° C. |
| Oleic acid (C18:1) | +14° C. | Methyl-Oleate | −20° C. |
| Linoleic acid (C18:2, n6) | −8.5 | Ethyl-Oleate | −27° C. |
| Alpha-Linolenic acid (C18:2, n3) | −16.5 | Methyl-Linoleate | −35° C. |
| Docosahexaenoic acid (C22:6, n3) | −43° C. | Ethyl-Linoleate | −38° C. |
| Araquidonic acid (C20:4, n6) | −49.5° C. | Methyl-Linoleate | −40° C. |
| Eicosapentaenoic acid (C20:5, n6) | −54° C. | Ethyl-Linolenate | −46° C. |
| Stearidonic acid (C18:4, n3) | −57° C. | Ethyl-Docosahexaenoate | −65° C. |
| Phytanic acid (C20) | −65° C. | Ethyl-Arachidonoate | −73° C. |
| Pristanic acid (C19) | −80.5° C. | Ethyl-Eicosapentaenoate | −76° C. |

This is an interesting method in terms of the elimination of PhA from the start of the production chain of oils, specifically in fish, which is free of toxicity and reported to have a lower risk of forming trans fatty acids and is adequate for obtaining a pharmaceutical or an alimentary grade. This invention concerns a highly adaptable method to current technology, particularly to the pharmaceutical and alimentary technologies, since cold technology was already being used in both industries. The increase of pressure in oil rich in omega-3 to reduce the MP and its energetic cost are not an option, as PUFAs and DHA are sensitive to hydrogenation.

On the other hand, this method along with the contemporaneous industrial technology used for separating of PhA, allows an increase of the degree of purity in DHA, EPA and other fatty acids with a very low MP, without adding any other additional purification processes. It is also a DHA and omega-3 fatty acids purification process, mainly for fish.

The subject invention relates to both non-refined and refined oils containing any omega-3 proportion, and to oils subject to purification for obtaining a high level of purity in any of the omega-3 fatty acids, preferably DHA, or in the total omega-3 content. For that aim, we can be based on fats or oils containing any kind of ester, principally triglycerides, phospholipids and ethyl-esters.

The main purpose is to obtain omega-3 oils, preferably with DHA and high level of purity (>700 mg/g), low or zero levels of PhA (<5 µg/g) preferably associated with esters rich in triglycerides to obtain higher purity, stability and bioavailability, with no need to add non-nutritional ingredients with potential interaction grade, such as ethanol, which use as food is avoided, especially among pregnant women and children, whereas this is the population sector where it is more needed and used. Free fatty acids are highly unstable to oral use, although its use as an injectable can entail benefits (i.e.: intravitreal injection). Given that active principles of this invention are the omega-3 fatty acids, particularly DHA, and taking into account that the required dose is too high for a therapeutic use, we consider triglycerides to be the best option, as it is the ester in DHA which allows higher concentration of the active principle. The oral intake of ethyl-esters is damaged, while the natural fatty acids intake on diet comes from triglycerides. Daily diet entails a natural intake of more than 100 grams of triglycerides, which demonstrates that DHA is the most efficient intake among mammals from the physiological and pharmacokinetic point of view.

Ethyl-DHA is a chemical formula hardly used in humans and in nature, whilst that of triglyceride is far more bioavailable and without the drawbacks and secondary effects associated to the ethyl-ester type. DHA as ethyl-ester is less efficient, it is physiologically more sensitive to oxidation, it is not a food (it contents alcohol), it does not form part of any diet among living organisms, its use is restricted (not adequate as food), it interferes with other fatty acids and increases the production of other ethyl-esters, interferes with other drugs and foods (i.e. coffee), it causes intolerance in a significant part of the population, it has secondary effects since it is a type of alcohol intake and it is a non-oxidative metabolite of ethanol inducing hepathotoxicity and pancreatitis. This document refers to the triglyceride form of DHA as a safe, healthy and most efficient drug as source of omega-3, whilst the ethylester is an intermediate process to obtain DHA and EPA as triglycerides.

The main use of the product is the obtaining of a healthier and rich in DHA medicament, supplement or food, presenting a higher physiological activity, without interferences o interactions non-associated to DHA, less oxidative capacity in vivo, less toxic and zero-risk rate associated with PhA for public health. According to the innumerable and recent molecular evidences, preclinical and epidemiological studies, PhA is a non-nutritional substance although present on diet, which entails one of the major risks to health.

This method of separating PhA is a highly effective deodorization method. To carry it out, the treatment of fish oil with soil or activated carbon will suffice, with views to eliminate heavy metals, avoiding so any heating or deodorization process. The subject invention entails not only the elimination of PhA and PA but also the efficient elimination of the volatile particles which cause the characteristic odour, avoiding also processes that may harm the oil (high temperatures) and reducing costs as no specific processes are added.

The oil deodorization base carried out following this separating process of PhA is relative:

a) To degradation of proteins, which have a very high MP and are in solid state at room temperature. Proteins are separated in the solid fraction or stearin in raw fish oils.

b) Due to the fact that the volatile substances which cause the odour in fish have a very low MP. Substances such as heptadienal, octadien, octene, heptenal, decatrienal and particularly dimethylamine and trimetrhylamine, have a PF rated at −92° C. and −117° C., respectively.

During the cooling and solidification processes in oil, the aforementioned substances will be part of the liquid fraction that is to be separated, and which contains these volatile substances along with the PhA and other alkenes and alcohols with low levels of PhA. Deodorization is carried out by cooling process and not by heating, with no need of purification process whatsoever. The present invention allows obtaining non-purified refined oils without having to carry out any conventional process for deodorization—which increases the risk of altering polyunsaturated fatty acids (high temperatures).

PhA is present fundamentally on triglycerides (>80% approx.) and other esters, detected in free form in small amounts, appearing at the same position (C-2) in both triglycerides and phospholipids in oils, the same as PUFA fatty acids and due to their comparable physicochemical characteristics. PhA extraction, as in all processes of purification of DHA and omega-3, cannot be carried out directly from triglycerides, containing 3 fatty acids with different MP according to their mixture. Then, fatty acids must be previously obtained by hydrolysis of the triglycerides that are part of the oils or fats in order to form free fatty acids through transesterification (catalytic) to form esters from alcohols o through hydrolysis (catalytic) to obtain the free acids. Two situations may arise:

Transesterification and formation of esters of fatty acids (i.e.: ethanol):

Nevertheless, although it can be carried out from alcoholic esters obtained from catalytic transesterification (i.e.: ethanol), the MP in fatty acids is considerably reduced to approx. >20° C., depending on the type of alcohol (Table 1). This fact entails a higher energetic cost, as to solidify oil with DHA, temperature should be reduced 20° C. lower than in cases where fatty acids are free.

b) Catalytic Hydrolysis (i.e.: saponification+acidification) for obtaining free fatty acids:

Catalytic hydrolysis is a method vastly applied to fish oils taking as a base any conventional method widely developed and used in current industry. Any organic acid of alimentary or pharmaceutical grade would serve as catalysers, such as acetic acid, or solid catalysers such as resins of ionic exchange (styrene resin), or enzymatic catalysis by lipase (ej: Novozyme 435) whether immobilised or in solution.

Fish oils have non-saponifiable fats containing cholesterol, PCBs, A and D vitamins, etc., which must be eliminated from oils rich in DHA or in omega-3 with the aim of obtaining an alimentary or pharmaceutical grade. A widely used, cost-effective and efficient method to separate non-saponifiable fats (stearin) in refining processes is the complete hydrolysis by saponification of fish oil in moderate alkaline medium, at low temperatures and in an inert ambient to avoid alteration of polyunsaturated fatty acids. In this way, necessary hydrolysis in refining processes is useful to proceed with the separation of PhA in this invention.

Because of this, the subject invention was initiated from hydrolysis of triglycerides and esters found in fish oil in a moderate alkaline medium (i.e.: potassium hydroxide of sodium hydroxide) at low temperature, for obtaining a liquid oil and to favour hydrolysis (i.e.: 40° C.-90° C.), until the complete hydrolysis and saponification of fatty acids.

The resulting mixture contains salts (potassic or sodium) from fatty acids that are not suitable for the procedure described in this invention as it alters the MP in fatty acids, so acidification or catalysed hydrolysis is carried out by use of non-oxidative organic acids (i.e.: acetic acid) adding it to the vigorously stirred mixture for obtaining fatty acids in free form.

It is possible to proceed to vacuum distillation on oil to separate the free fatty acids (i.e.: 2 mmHg) and inert atmosphere to avoid any damage on the free PUFA fatty acids. Nontheless, this method facilitates the separation of the solid phase, containing stearin and non-saponifiable fats, by decantation and centrifugation, and the liquid phase, which contains the acidified oil, by washing it repeatedly, containing sodium or potassium acetate. This would guarantee the glycerol conservation.

Glycerol is safer than solvents of alimentary or pharmaceutical grade, and entails a much easier method given its necessary presence in both the start and the final phase of the product. But the most remarkable aspect is that glycerol allows density gradient separation, which favours crystallization much more efficiently than in fractionation methods currently used with other chemical substances (i.e.: urea), fractioning saturated and monounsaturated fatty acids, and particularly, for separating PhA and omega-3.

Glycerol in acidified oil is the safest cryoprotectant agent and a good humectant, which favours crystallization of saturated fatty acids in the PhA separation phase. Moreover, the present invention adds glycerol to the acidified oil to favour the density gradient fractionation, which also helps to develop not only the fraction by centrifugation gradient but also crystallization.

As for the density gradient centrifugation used in this invention, it is required a gradient that gathers certain characteristics: low molecular weight (it reduces centrifugation time), low viscosity, higher density than in solutes (fatty acids), transparent under UV light and good solvent properties. Glycerol, which has a high density (1.25 g/cm$^3$), acts as medium for the density gradient fractionation or molecules split up to 1.15 g/cm$^3$ as detected in the case of fatty acids found in rich in omega-3 oils. Glycerol can be mixed with water or any other solvent to reduce significantly its eutectic point (i.e: glycerol dissolution at 65% in water reduces the MP from +18° C. to −47° C.), which would make it be in liquid state during the crystallization process. Glycerol in a small fraction of solvent allows reducing viscosity (Table 2), behaving as an ideal gradient in isopycnic centrifugation. Viscosity can also be reduced by increasing temperature, especially during the cooling phase of this invention. It is an ideal gradient for the fraction by centrifugation of fatty acids by density gradient and crystallization.

Fatty acids composition, key in the content of these oils, does not reveal significant differences in molecular weight but in density (three fractions of fatty acids). Its MP behaves similarly, optimising considerably the crystallization of these fatty acids proximate to MP. Among both centrifugation techniques by density gradient (zonal or isopycnic), the most adequate one for this invention is the isopycnic one, as it causes fractions according to density because there are no significant differences in the molecular weight between PhA (312.53 g/mol) and DHA (328.5 g/mol) and the EPA (302.4 g/mol) required for the zonal technique. Nevertheless, it can be used for separating saturated and monounsaturated omega-3 fatty acids and at the limit of the technique (8%) for separating DHA and EPA (although in this invention they were separated in the same way as other molecules with molecular weight differences of <10% (Fuentes-Arderiu et al., 1998).

In this invention the density gradient fractionation is carried out before the crystallization in order to form 3 fractions according to the density corresponding to the main oil fractions: saturate and monounsaturated fatty acids and omega-3. This would cause fraction and modification of the eutectic point of the oil's fatty acids mixture, optimizing in a high proportion the solidification of fractions according to their MP. This procedure is also efficient when optimizing in the separation of PhA from omega-3, without using any solvent.

TABLE 2

| Viscosity-Temperature Correlation for. Glycerol-Water Solutions (mPa) (Dorsey, 1940) | | | | | | | | | | | |
|---|---|---|---|---|---|---|---|---|---|---|---|
| Glycerol | Temperature (° C.) | | | | | | | | | | |
| % w/w | 0 | 10 | 20 | 30 | 40 | 50 | 60 | 70 | 80 | 90 | 100 |
| 0 | 1.792 | 1.308 | 1.005 | 0.8007 | 0.6560 | 0.5494 | 0.4688 | 0.4061 | 0.3565 | 0.3165 | 0.2838 |
| 10 | 2.44 | 1.74 | 1.31 | 1.03 | 0.826 | 0.680 | 0.575 | 0.500 | — | — | — |
| 20 | 3.44 | 2.41 | 1.76 | 1.35 | 1.07 | 0.879 | 0.731 | 0.635 | — | — | — |
| 30 | 5.14 | 3.49 | 2.50 | 1.87 | 1.46 | 1.16 | 0.956 | 0.816 | 0.690 | — | — |
| 40 | 8.25 | 5.37 | 3.72 | 2.72 | 2.07 | 1.62 | 1.30 | 1.09 | 0.918 | 0.763 | 0.668 |
| 50 | 14.6 | 9.01 | 6.00 | 4.21 | 3.10 | 2.37 | 1.86 | 1.53 | 1.25 | 1.05 | 0.910 |
| 60 | 29.9 | 17.4 | 10.8 | 7.19 | 5.08 | 3.76 | 2.85 | 2.29 | 1.84 | 1.52 | 1.28 |
| 65 | 45.7 | 25.3 | 15.2 | 9.85 | 6.80 | 4.89 | 3.66 | 2.91 | 2.28 | 1.86 | 1.55 |
| 67 | 55.5 | 29.9 | 17.7 | 11.3 | 7.73 | 5.50 | 4.09 | 3.23 | 2.50 | 2.03 | 1.68 |
| 70 | 76 | 38.8 | 22.5 | 14.1 | 9.40 | 6.61 | 4.86 | 3.78 | 2.90 | 2.34 | 1.93 |
| 75 | 132 | 65.2 | 35.5 | 21.2 | 13.6 | 9.25 | 6.61 | 5.01 | 3.80 | 3.00 | 2.43 |
| 80 | 255 | 116 | 60.1 | 33.9 | 20.8 | 13.6 | 9.42 | 6.94 | 5.13 | 4.03 | 3.18 |
| 85 | 540 | 223 | 109 | 58 | 33.5 | 21.2 | 14.2 | 10.0 | 7.28 | 5.52 | 4.24 |
| 90 | 1310 | 498 | 219 | 109 | 60.0 | 35.5 | 22.5 | 15.5 | 11.0 | 7.93 | 6.00 |
| 91 | 1590 | 592 | 259 | 127 | 68.1 | 39.8 | 25.1 | 17.1 | 11.9 | 8.62 | 6.40 |
| 92 | 1950 | 729 | 310 | 147 | 78.3 | 44.8 | 28.0 | 19.0 | 13.1 | 9.46 | 6.82 |
| 93 | 2400 | 860 | 367 | 172 | 89 | 51.5 | 31.6 | 21.2 | 14.4 | 10.3 | 7.54 |
| 94 | 2930 | 1040 | 437 | 202 | 105 | 58.4 | 35.4 | 23.6 | 15.8 | 11.2 | 8.19 |
| 95 | 3690 | 1270 | 523 | 237 | 121 | 67.0 | 39.9 | 26.4 | 17.5 | 12.4 | 9.08 |
| 96 | 4600 | 1580 | 624 | 281 | 142 | 77.8 | 45.4 | 29.7 | 19.6 | 13.6 | 10.1 |
| 97 | 5770 | 1950 | 765 | 340 | 166 | 88.9 | 51.9 | 33.6 | 21.9 | 15.1 | 10.9 |
| 98 | 7370 | 2460 | 939 | 409 | 196 | 104 | 59.8 | 38.5 | 24.8 | 17.0 | 12.2 |
| 99 | 9420 | 3090 | 1150 | 500 | 235 | 122 | 69.1 | 43.6 | 27.8 | 19.0 | 13.3 |
| 100 | 12070 | 3900 | 1410 | 612 | 284 | 142 | 81.3 | 50.6 | 31.9 | 21.3 | 14.8 |

Separating PhA and purification of omega-3 fatty acids by: 1—fractional crystallization according to their different densities using a density gradient.

Separating methods of fatty acids found in oils are specially complicated to carry out, particularly in cases when the fatty acids share physicochemical properties which are essential in separating methods: distillation, crystallization, extraction with solvents or chromatography. Fractional crystallization is a process to separate different substances whose solubility is different in terms of temperature variations. Despite the fact that the base of fractional crystallization is referred to this physicochemical property, actually the fractional crystallization consists on the separation of two or more chemical compounds according to their different MP.

The proposed method in this invention has not been described before, as it suggests a method in which two or more components can be separated, fractioning them in terms of density and not solubility, according to temperature variations. Because of this, the invention is denominated Fractional Crystallization by Density (FCD).

The described method could be used for separating components: a) with similar properties (i.e.: homogenous solutions) in relation to complex interactions that result in variations of the eutectic composition diagram, or b) even in heterogeneous compositions with different solubility but where any of the components is highly sensitive to temperature variations or rises. The subject invention refers specifically to the separation of a certain oil homogenous composition in two or more compositions, varying their eutectic point and proceeding to temperature variations by applying a cooling process and separating by fractional crystallization. The main purpose is to separate a fraction composed of saturated and monounsaturated fatty acids and PhA, which contains a higher eutectic point than a fraction containing omega-3 fatty acids.

Crystallization and density turn out to be the most differential properties when separating omega-3 fatty acids, PhA and saturated fatty acids. This invention allows separating in fractions of fatty acids or micelles (according to the liposolubility of the gradient) containing a high proportion of fatty acids with lower density as saturated an monounsaturated fatty acids and PhA of omega-3 fatty acid, with higher density. These two compositions, which can be pure or not (mixture of different fatty acids), have different eutectic points in relation to the MP and to the concentration of the individual composition of fatty acids; two fractions of different compositions can be separated by fractional crystallization.

This process is also particularly efficient for separating even similar substances by fractional crystallization, according to their density. Such is the specific case of this invention, when one of the components PhA (3S) in low concentration levels has a similar MP than a (DHA) component/s. In this invention, ultracentrifugation by isopycnic or non-isopycnic density can be applied. The application of solvents usually used for obtaining DHA with high levels of purity is not required in the process of this invention.

Option 1: Fractional Crystallization by Isopycnic Density-Gradient Ultracentrifugation Centrifugation has been demonstrated to be 90% more cost-effective in chemical products, 70% in terms of human work load, 60% faster and more ecological because it does not use solvent for separating free fatty acids and fats (Feng et al., 2004). Centrifugation and refrigeration are widely used in the food industry. In this invention it is possible to favour the separation and crystallization of omega-3 fatty acids and PhA with or without solvents. There has been widespread use of ultracentrifugation at a large scale in the pharmaceutical industry. It should be noted that ultracentrifugation allows separating different fatty acid fractions before crystallization.

The use of centrifugation for the separation of macromolecules is well known, but it has not been used yet for separating very small molecules such as fatty acids with similar molecular weight and different density. It has been separated 99% of DDT, a liposoluble compound with a molecular weight comparable to that of fatty acids, by Ficoll density-gradient ultracentrifugation (Adamich et al., 1974). In this invention, fatty acids with similar molecular weight (with 300 Daltons) are fractionated by isopycnic density-gradient ultracentrifugation.

Acidified oil containing free fatty acids will be used in the specific phase of this invention: separation of PhA from rich in omega-3 oil. In this method, the physical state of the oil is changed by crystallization of the oil itself, containing omega-3 fatty acids (i.e.: DHA), keeping PhA and PA in a liquid state and separating specifically the PhA and PA from crystallization of fractions of DHA, EPA, PhA (3S). This technique allows the obtaining of DHA and EPA with high degrees of purity >95% and >99%, or a triglyceride of alimentary or pharmaceutical grade (>850 mg/g), without PhA (<5 µg/g). The costly loss of omega-3 fatty acids can also be avoided.

Fatty acids have auto-nucleation properties and they do not have the quality of overfusion. The melting point (MP) and the freezing point is the same. Because of this, for carrying out the purification of omega-3 fatty acids free of PhA, it would suffice to obtain two or more fractions with different eutectic points that allowed the aforementioned purification process.

Saturated fatty acids have a high MP (>18° C.), whilst in monounsaturated fatty acids the MP is >13° C. Besides, the composition in saturated and monounsaturated fatty acids in raw acidified oil is >50% (for those of algal origin) and frequently reaches levels of 70% (fish oils). Nevertheless, the numerous quantity and presence of omega-3 fatty acids species, significantly reduces the eutectic point, which results in an ineffective cooling crystallization process at very low temperatures, such as −20° C.

On the other hand, as it can be seen in Table 1, the MP in PhA is 20° C. higher and 10° C. lower than MPs in DHA and EPA, respectively. However, PhA isomers present in certain oils (i.e.: fish oils) decrease in approx. 2° C. the existing difference between PhA (3S) y el DHA.

Given the fact that oil does not meet the conditions for crystallizing its components or fatty acids with similar solubility for fractionation, a previous fatty acids fraction by fractional crystallization by density is carried out. So with this invention, deodorization method is optimised, as well as purification of oil containing omega-3 and fractional crystallization of DHA and omega-3.

For this purpose, it is initially carried out a fractional centrifugation by density-gradient or by isopycnic autoformed-gradient. This is a technique used for separating molecules of similar molecular weight but different densities not only in laboratory processes, but also in essentially pharmaceutical industry processes, for purifying and separating proteins and creating vaccines, among other applications.

In this technique, oil is dissolved in an isocratic solution and under a centrifugal force, fatty acids form a gradient according to their density and not to their molecular weight, due to the fact that they distribute in the reactor during centrifugation. The main premise is that the maximum gradient density (i.e.: glycerol) should always exceed the fatty acids density. Centrifugation by density-gradient allows fatty acids to move along the gradient until they reach a point where their density and that of the gradient are the same (isopycnic). In this very moment, crystallization separation will take place, as conventional separation is to be done very carefully and would cause an undesired contamination of the omega-3 oil.

A gradient containing a partially apolar solvent (i.e.: heptanol) can be used to create a homogenous oil gradient mixture and help the separation of individual fatty acids without forming micelles. In this way, there is a dispersion of the free fatty acids, obtaining a fraction more pure in omega-3 fatty acids, without PhA and losses. However, this presents two difficulties: the separation of the gradient on the final product and the fact that the molecular separation of free fatty acids requires a longer ultracentrifugation time. Because of the first reason, one of the normal conditions of the gradients is its water-solubility. When using a lipid-soluble gradient, it can be separated during the final process following this procedure and as long as it contains a MP differential with the fraction to be separated.

The gradient used for the present invention is glycerol, as it is produced during the process, it is inexpensive and safe for alimentary and pharmaceutical use, without discarding any other gradient for this purpose (i.e.: sucrose), being its high viscosity the biggest inconvenience in both cases. When using glycerol as a gradient, it should be refrigerated at 10° C.

or below the MP of glycerol (18° C.) during the ultracentrifugation. However, it behaves very well as a superfused liquid in dissolution with water and other solvents.

In this invention, several solvent mixtures with glycerol are used to reduce viscosity and lower the MP of the gradient. Particularly, is the use of solvents that favour crystallization, but most of all, to reduce the eutectic point and viscosity of the gradient. The use of solvents with a high alimentary and pharmaceutical grade, such as glycerol/water mixtures, isopropanol or other alcohols, is advisable but not exclusionary. Solvents such as glycerol/water mixtures and acetone have a great amphipathic and humectant behaviour as solvents which stimulates the crystallization of the fatty acids, especially at the temperatures required in this invention, as it has a very low MP (−95° C.).

The most suitable glycerol mixtures are those that allow glycerol to reduce viscosity, reduce moderately the MP and significantly viscosity. The reduction of viscosity of the gradient is essential for the resolution of fractions and the time for equilibrium in order to separate the PhA more efficiently. With glycerol/water mixtures, the ideal proportion is that which allows the formation of a supercooled or superfused liquid, decreasing its MP significantly: glycerol: 67% w/w with an MP of −47° C. At the same time, the density is reduced, shortening considerably the duration of the centrifugation by density gradient, an inexpensive and safe result.

The use of other glycerol mixtures is also possible, using low amounts of solvent, avoiding a drop of density below DHA (>0.95 g/cm3) so that it can be used as a gradient, acting alcohols as short-chain polar solvents (C1-C5) for the dispersion of micelles, and preferably solvents for obtaining a medium-chain partially polar gradient (C6-C8) that allow the dispersion of free fatty acids. The proportion of glycerol in these alcohols must have a higher density and a low MP. An amount of glycerol between 5% and 50% allows a reduction of the MP inversely proportional in the range of temperatures during ultracentrifugation, reducing considerably density and viscosity but always being >1 g/cm3, necessary for this invention. For this invention, a glycerol gradient at 25% w/w and an MP of approx. −7° C. allows an optimization of the fractionation procedure reducing the ultracentrifugation time. Glycerol at 50% w/w is enough for obtaining a MP of approx. −23° C. and for exceeding the maximum temperature reduction of an ultracentrifugation at a large scale.

The use of water-soluble gradients will stimulate the formation of nanomicelles which will reduce the equilibrium time. However, in order to reach the ideal equilibrium and fractionation, the composition of these micelles has to be highly homogenous according to their density. The diffusion of the fatty acids will take place following a pattern according to the density and not chosen at random, modified by ultracentrifugation by density gradient. As it occurred in the centrifugation gradient, the density gradient is formed according to the distance to the rotor axis; the process initially develops forming micelles containing fatty acids with the highest density, which will form the densest, furthest away fraction from the rotor axis.

The significant increase of the density of fatty acids, especially the PhA and saturated omega-3 fatty acids, make it an efficient technique. The main problem is that a relatively small molecular weight requires very high speeds and durations to obtain the separation. An excess of time will not affect the separation. However, as molecules have such low molecular weight, the required time is high (i.e.: 48 hours), and although not outstanding in separation procedures, this time can be optimized.

By means of an isopycnic ultracentrifugation applied on a raw oil rich in omega-3, 3 fractions are formed according to molecular weight and density: a) saturated fatty acids containing mainly myristic, palmitic and stearic acid with a molecular weight of (228-290 g/mol) and a density lower than oil (0.85-0.86 g/cm3) b) monounsaturated fatty acids with a similar molecular weight and a slightly higher density (0.88-0.89 g/cm3) c) omega-3 fatty acids with a molecular weight of (300-330 g/mol) and a higher density (0.93-0.95 g/cm3). The PhA is detected in fraction (b) through an isopycnic centrifugation with a density of (0.88 g/cm3).

This can be performed with linear or nonlinear, continuous or discontinuous gradients, having chosen for this invention the continuous linear method because of its industrial application. Reducing the time necessary to obtain the equilibrium is essential in this invention. This is why the most adequate method in this case is the use of vertical rotors, as they reduce the equilibrium time considerably.

The speed of the ultracentrifugation can start at 30,000 rpm or 100,000×g until equilibrium is reached. There is no excess time in this technique. As the ultracentrifugation starts, the fatty acids slowly start to diffuse with the help of the gradient. The saturated fatty acids crystallize slowly at 20° C. and the monounsaturated fatty acids at 10° C. The formation of the equilibrium will increase significantly the eutectic point of the oil at the beginning of the ultracentrifugation and with it the slow formation of crystals. Fatty acids do not vary significantly in density at a solid state.

Therefore, the ultracentrifugation at 10° C. contributes to the crystallization of the phases to discard (a) and (b), containing saturated and monounsaturated fatty acids. Therefore, when the equilibrium is reached, it is possible to separate the liquid fraction containing the omega-3 and the gradient without risk of contamination.

Fraction during the centrifugation is not always completely crystallized at 10° C., as the mixture of monounsaturated fatty acids and PhA reduces the eutectic point. For this reason it is advisable to cool at a temperature of between 0 to −5° C. or preferably at −30° C., or at a temperature below the eutectic point of the purified fraction with omega-3 fatty acids, which will vary according to the composition between approximately −44° C. and −57° C., essentially depending on the composition of the DHA and the EPA.

The cooling process can be carried out simply by cooling the beaker containing the gradient in equilibrium. However this cooling process can take place during ultracentrifugation, as the ultracentrifugates at a large scale allow a reduction of the temperature down to −20° C., improving the crystallization at these stages. However, in this invention the cooling process takes place during or close to the equilibrium point, therefore guaranteeing the solidification of the PhA.

Setting the temperature at 20° C. or below during the ultracentrifugation is not exclusionary in this invention. It is possible to reduce the equilibrium time and optimize the ultracentrifugation process by increasing the temperature (ie. 60° C.) (between 20° and 90° C.), as it reduces considerably the viscosity of saturated fatty acids, particularly that of saturated and monounsaturated ones as well as reducing the viscosity of the gradient (glycerol), optimizing the fractionation and reducing considerably the centrifugation time until the equilibrium is reached.

Changes can be made to the isopycnic centrifugation process so as to reduce its duration and optimize the separation of the PhA. In this regard, crystallization can be achieved without reaching equilibrium, in order to reduce the duration of the ultracentrifugation. Usually the time necessary to reach equilibrium is 48-72 hours, depending on the gradient, temperature, speed and rotor used. Given that the PhA constitutes a very small fraction and that we are not aiming for chemical pureness, it is possible to obtain the specifications of this invention without reaching equilibrium.

Within 24 hours, most of the fractionation of the omega-3 fatty acids and the rest of the fatty acids and PhA has occurred. In this way, most of the fatty acids, including most of the PhA is sensitive to crystallization at temperatures below those of omega-3 fatty acids. In this manner, we can proceed to crystallization before the equilibrium is reached, reducing the temperature (i.e.: ° C.) of the ultracentrifugation during whatever time is necessary (i.e.: 24 hours) in order to separate the liquid fraction containing omega-3 acids and the gradient. The ultracentrifugates at a large scale allow reaching temperatures to −20° C. By doing so, we can also separate the PhA effectively and purify the oil containing omega-3 fatty acids without losing any material.

Option 2: Fractional Crystallization by Non-Isopycnic Density-Gradient Ultracentrifugation Even though it is possible to extract omega-3 purified oils from the fraction, the risk of contamination is high. The duration of the ultracentrifugation can also be reduced significantly without reaching a complete equilibrium or quasi-equilibrium of the density gradient. By doing this one could eliminate a high concentration of saturated fatty acids and a part of the PhA, which according to its original concentration and isomer (3R), could be enough to obtain the specifications of this invention. Nevertheless, in most circumstances, better results are obtained when separating through crystallization.

In this invention different temperature cycles can be established or a zone fractionation can be used to purify the DHA and EPA.

Figure 5:
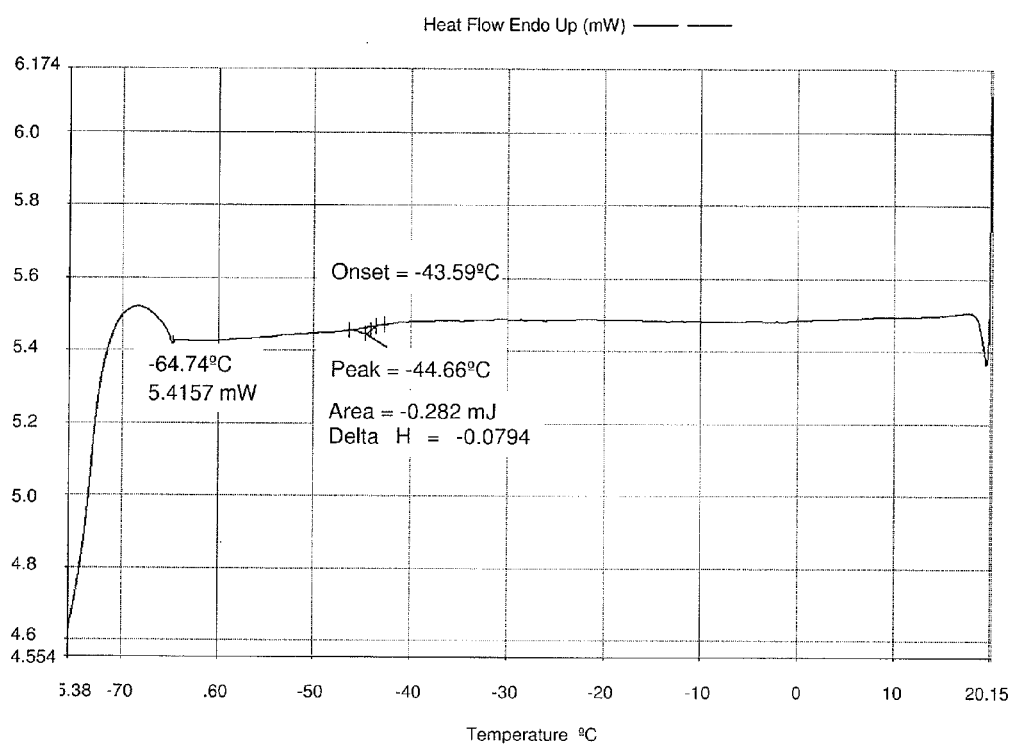
FIG. 5. Calculation of the melting point (FP) through DSC (Differential Scanning Calorimetry) of the two diastereoisomers of PhA The method DSC is a thermo-analytical technique which differentiates the heat needed to increase the temperature of a sample. The main functions of the technique are the study of the phase transitions or of the physical state such as the melting point (MP). This technique exhibits a great sensibility to estimate the MP. For this invention, two standards have been created for each isomer of PhA, since there is non available in the world market.

Isomer PhA (3S), which can be usually found in small proportions in fish oils and other marine origin oils, with the exception of mammals and microorganisms (i.e.: tuna rich in DHA), has the MP close to DHA (Table 1 and FIG. 5). This isomer constitutes a big obstacle for its separation by crystallization. Therefore, the separation of this isomer, particularly when using this invention, requires a previous isopycnic centrifugation of the oil, given the differences in the densities of PhA (0.882 g/cm3) and DHA (0.943 g/cm3), while MP temperature of the PhA is just 2° C. lower.

The eutectic point of oils rich in omega-3 is below 40° C. before they are fractioned. With this separation procedure it is possible to obtain behaviour of the crystallization of the different fractions differential enough from the different eutectic points of the fatty acid compositions of the fractions. The eutectic point of the mixture in fractions (a) a (b) rises significantly, compared to the original composition of the fatty acids, containing PhA (~0.1%). Also contained in this fraction are the volatile components responsible for the characteristic odour of oils. Said eutectic point, makes the solidification of the fraction at temperatures <−20° C. possible, but high enough to separate efficiently fraction c) of the omega-3 fatty acids with a eutectic point below −40° C. In this way PhA is a part of the solid fraction (b) or (b+a). Fraction (b) contains practically the totality of PhA (two isomers) in oils, which allows a highly effective separation of PhA (3S) which would be very complicated to separate by crystallization.

The necessary crystallization time can vary between 18 and 72 hours. The cooling speed should be slow enough to stimulate the crystallization of fatty acids, although DHA crystallization has occurred in 24 hours with a reduction on temperature/speed of −3.3° C. or lower cooling speed.

It is possible to obtain a growth of free DHA crystals, so that once separated they retain the smallest liquid phase amount possible. This is why it could be convenient that large crystals be formed during the process, slowly lowering the temperature. Crystallization can be done in large deposits, kept in a cold store or cryogenic freezers at a temperature starting at −44° C.

In non-purified or raw oils, or oils containing a high proportion of saturated and/or monounsaturated fatty acids, PhA is separated by using a temperature cycle of −30° C. (between −20° C. and −40° C.) below the MP of omega-3 fatty acids and the eutectic point of oil. This is how a solid fraction containing saturated fatty acids+monounsaturated fatty acids+PhA can be separated from the liquid fraction containing a high purity of DHA and EPS through filtration, if necessary.

At this temperature, the glycerol gradient crystallises, staying in liquid state just the fraction with the highest density and lowest MP with a high purity omega-3, also separating the gradient of the omega-3 fatty acids. However, if a glycerol/water mixture at 67% w/w is used, it will remain liquid which will allow another centrifugation process by density gradient (i.e.: separation of DHA/EPA or oil rich in DHA/PhA) or to regenerate the gradient for another PhA separation process in another batch of oil.

This procedure eliminates almost completely the totality of the two PhA isomers. In this way we obtain omega-3 oil with high purity in its two principal components DHA and EPA (>95% or >800 mg/g) and usually >99% deodorised and with a low or zero PhA. According to the DHA/EPA ratio in the original oil it can be obtained:

a) For an oil containing essentially DHA as sole omega-3 fatty acid (i.e.: *Schizochytrium* sp.) a DHA >95% (>850 mg/g) or >99% (>900 mg/g) is obtained.
b) For a ratio DHA/EPA >3 (i.e.: tuna) an oil rich in DHA >700 mg/g containing PhA (<5 μg/g) is obtained;
c) For a ratio DHA/EPA between 1 and 3 (i.e.: salmon) an oil with DHA <700 mg/g containing PhA <90 μg/g is obtained;
d) For a ratio DHA/EPA <1 (i.e.: red fish, anchovy, mackerel, sardine, cod) an oil with EPA >400 mg/g and DHA <400 mg/g containing PhA <5 μg/g.

With this invention we can also fractionate the DHA and EPA, obtaining a DHA and EPA of high purity and low content or zero PhA. The DHA and EPA present a 10% difference in molecular weight, enough differential for the zonal ultracentrifugation (Arderiu et al., 1988). For this, it is possible to perform a second cooling cycle, a previous and necessary process of zonal density-gradient ultracentrifugation at −50° C. or between −44° C. and −54° C., or at any other temperature between the MP of the DHA and EPA. Regardless of the original composition, a high purity of DHA and EPA and a low concentration or no PhA is obtained in all oils.

At this point some alimentary or pharmaceutical lipophylic antioxidant can be added (i.e.: tocopherols) in order to stabilize the oxidation of PUFAs. Acidified oil with a low PhA or zero PhA content requires an immediate esterification of the free fatty acids by alcoholysis or formation of novotriglycerides, our main objective, by any conventional mean carried out at the industry at present time, unspecific or selective enzymatic or another method with a liquid or solid catalyst (i.e.: Patent US 20080114181). In the case of oil containing ethyl-ester, reesterification will be also carried out to obtain triglycerides.

Diagram as examples for developing triglycerides of DHA >700 mg/g and <0.5 μg/g of PhA. However we can usually obtain DHA concentrations of >900 mg/g (the theoretical maximum of purity in DHA in oil is a 100% pure triglyceride that would contain approx. 960 mg/g). The procedure chosen is the same for all raw materials, although the DHA concentration will depend on the raw materials chosen at the beginning and the optional process to fractionate DHA to separate the EPA. In this regard, for all source oils containing DHA/EPA >3 the purification processes of the omega-3 will results in purities of DHA >700 mg/g Examples:

Raw material 1: Oil containing DHA only without a significant content of omega-3 fatty acids.

I.e.: Oils from the biomass or microorganisms (i.e.: Schizochytrium sp) containing triglycerides DHA >400 mg/g and PhA >120 μg/g.

Raw material 2: Oils rich in omega-3 with different DHA/EPA ratios as the only significant content in omega-3 fatty acids.

DHA/EPA <1. I.e.: red fish refined oil (30% omega-3) containing triglycerides DHA >100 mg/g; EPA >150 mg/g and PhA >1900 μg/g DHA/EPA <3. I.e.: Tuna fish refined oil (30% omega-3) containing triglycerides DHA >200 mg/g; EPA >60 mg/g and PhA >1300 μg/g DHA/EPA <3. I.e.: Purified tuna refined oil (70% omega-3) containing triglycerides DHA >500 mg/g, EPA <150 mg/g and PhA >1600 μg/g Raw material 3: DHA purified oils with a low EPA content >700 mg/g are produced and obtained regularly as ethyl-ether and purified formulations (i.e.: Molecular distillation). They do not require the purification of omega-3 fatty acids, only the PhA has to be extracted.

DHA/EPA >7. I.e.: Purified tuna refined oil (90% omega-3) containing triglycerides DHA >700 mg/g, EPA <150 mg/g and PhA >3 μg/g The procedure is simultaneously PhA and PA free, but as indicated, only the PhA presents quantities clinically significant which is the reason why we always refer to PhA and only mention PA in results and sporadically on the patent. PA separates at the same fractionation point by crystallization as the PhA. Example 1 shows how much PA existed before and how much is left at the final analysis of the final product (example 1).

In order to illustrate the invention, different extracts obtained from different oils, rich in DHA and with a low PhA content are shown. The following examples are not exclusive to this invention. The extracts obtained can later be used in different galenic formulations, preferably capsules, as health supplements or medicines to treat different diseases.

EXAMPLES

Example 1

Procedure to Obtain an Extract Containing Triglycerides with DHA >700 mg/g and PhA <5 μg/g, by Isopycnic Ultracentrifugation and Crystallization The raw material used is non-deodorised and non-purified raw tuna oil (Sanco) containing DHA (210 mg/g), EPA (67 mg/g) and total omega-3 (285 mg/g). After quantifying fatty acids in oil through gas chromatography and mass spectrometry, PhA presence was determined (1.3 mg/g). Two decreasing temperature cycles are established for their effectiveness and in order to quickly achieve the main purpose of this innovation of DHA without PhA.

1. Saponification

In a 5-liter reactor with a shaker we proceeded to saponificate 1000 gr of raw tuna oil with 250 g of KOH, 280 ml of water and 10 ml of ethanol to initiate the reaction at a temperature of 40° C. under an inert atmosphere (nitrogen) shaking the mixture at 300 rpm for 1 hour.

2. Acidification Formation of Free Fatty Acids from their Salts

To the potassium mixture obtained in the previous phase we add 3 liters of acetic acid (non oxidant acid) at 70% and we mix it vigorously for 60 minutes at 200 rpm under an inert atmosphere (nitrogen). The potassium acetate salts formed, precipitate and are eliminated through filtration. Once settled, two phases are formed: an apolar phase and polar phase with higher density containing the remaining acetic acid, which is eliminated through an opening at the base of the reactor. Then, washing is performed by adding 4 liters of purified water to the reactor and shaking for 30 minutes at 150 rpm, once it has settled and two phases are formed: an apolar one containing the oil and an apolar one, which contains water, at the base of the reactor. The apolar phase is eliminated through the opening at the base of the reactor. Then, it is cleaned another 4 times adding 4 liters of water until one obtains a tuna acidified oil.

3. Isopycnic Centrifugation

The tuna acidified oil obtained in the previous phase is centrifuged at 150 rpm for 20 minutes forming a solid phase or stearine and a liquid phase containing the free fatty acids which is vacuumed in order to be used in the next step. 2400 ml of gradient are prepared from a glycerol/water mixture at 25% w/w, adding 1800 of water and 535 ml of glycerol, into which we add the free fatty acids obtained previously and the glycerol at room temperature.

The mixture is homogenised at 3000 g for 1 h in a Hitachi-Koki CC40 ultracentrifuge and a C40CT4 Core (H) rotor. Then, vacuumed (27 Pa) and at an initial temperature of 10° C., the centrifugation speed is increased to 1000000 g for 42 h. After 24 hours of ultracentrifugation, the temperature is lowered abruptly at 0° C. maintaining it for 18 hours until equilibrium is reached. From this centrifugation process we obtain 2 disposable solid fractions at the axis of the rotor, one of them containing saturated fatty acids and the other monounsaturated fatty acids and PhA.

In order to analyse the liquid phase, a sample is obtained using a pipette. The sample is subject to a GC-MS analysis and subsequently PhA and DHA concentration are checked, which results in <90 μg/mg and 740 mg/g, respectively.

In this particular case the fractions are not separated, even though the could be obtaining a product with PhA concentration below 90 μg/mg and a DHA concentration of 740 mg/g, respectively.

4. Separation by Crystallization of the Omega-3 Fatty Acids.

Next, direct or sharp cooling at a temperature of −30° C. is carried out for 24 hours of the cylinder containing the 3 fractions obtained during the previous phase. At this temperature two phases are produced: one solid and one liquid. The solid fraction contains the saturated and monounsaturated fatty acids, PhA, pristanic acid and the glycerol gradient, while the liquid phase contains the mixture of polyunsaturated fatty acids rich in DHA. The liquid fraction, which is the furthest from the radius of the cylinder axis, separates from the solid fraction through the opening at the base of the cylinder.

This liquid fraction contains omega-3 fatty acids rich in DHA with a low or zero PhA content. The 281 gr. of fatty acids rich in DHA obtained are analysed by GC-MS. The analysis indicates that in the omega-3 before and after refrigeration at −30° C. is 96.7% and 97.2% respectively and PhA levels are below 90 μg/g before refrigeration and below 5 μg/g after refrigeration.

5. Esterification of Free Fatty Acids in the Oil in Triglycerides

For the esterification of the free fatty acids obtained during step 4 we use the method described in the patent US20080114181. Using a Soxhlet condenser, the styrene resin is mixed at 5% with the free fatty acids (200 g) and glycerol (50 g), introducing a mechanical thermo shaker on the mixture at 185 rpm, 40° C. and 20 minutes. Next, we add 80 ml of ethanol to the mixture and we rise the temperature to 60° C. and the shaking to 235 rpm. The reaction is maintained for 24 hours at atmospheric pressure, under an inert atmosphere (nitrogen). The mixture is then cooled to room temperature and the resin or catalyst is recovered by filtration of the oil. The ethanol is eliminated, obtaining a triglyceride mixture.

A sample of the final product is taken to be GC-MS analyzed as described and the results obtained are those shown under example 1 below (including free fatty acids).

In the example 3 the GC/MS analysis of the oil is determined in order to determine the composition of the triglycerides, partial glycerides and free fatty acids obtained.

From the procedure performed during the 5 phases we obtain a completely deodorised oil containing DHA triglyceride at a concentration >700 mg/g and PhA <5 µg/g and a total of 870 mg/g of omega-3 (>95%).

Example 2

Continuous Procedure in Order to Obtain DHA ≥700 mg/g and PhA <90 µg/g

For this example, refined red fish (*Sebastes* sp.) oil was used as a starting raw material. (LYSI) with an omega-3 content of 315 mg/g, of which 110 mg/g are DHA and 165 mg/g EPA, and 1.9 g/kg PhA.

1. Saponification and 2. Acidification

We proceeded to the saponification and acidification of 1000 gr of red fish following the same proportions and procedure used during the example 1.

From the acidified oil two things can be done. The purified oil is divided in two identical portions for PhA separation and purification of omega-3 fatty acids, using one portion for the following step:

a) Isopycnic Ultracentrifugation and Crystallization

1. Isopycnic Centrifugation

We centrifuge 500 g of acidified oil at 150 rpm for 20 minutes forming a solid phase or stearine (274 gr.), vacuuming the supernatant liquid containing the free fatty acids to be used next on a glycerol gradient as indicated in the Example 1. As in the previous example, once the equilibrium is reached we obtain two solid phases containing saturated, monounsaturated and PhA fatty acids and a third liquid phase containing polyunsaturated fatty acids rich in DHA.

2. Separation by Crystallization of the Omega-3 Fatty Acids.

We proceed to cool the cylinder containing the three phases described previously at a temperature of −30° C. for 24 hours in order to solidify the gradient and therefore obtain a solid fraction containing saturated, unsaturated fatty acids and PhA and a liquid one containing omega-3 fatty acids. The liquid fraction is separated through the opening at the base of the cylinder, obtaining 156 g of acidified oil.

According to the specifications of the starting Red fish raw oil, we can estimate that the discarded solid fraction contains saturated fatty acids (68%), monounsaturated fatty acids (31%) and PhA 2.2 g. With GC-MS we analyse the 156 gr of acidified oil rich in omega-3 obtained that have a purity in omega-3 of 98.3% and PhA levels <90 µg/g.

3. Esterification of Fatty Acids Free of Triglycerides (the Same as Example 1).

The esterification process used is that described in the phase 5 of the first example. Using a Soxhlet condenser, we mix the styrene resin at 5% and the free fatty acids (200 g) and glycerol (50 g) introducing a mechanical thermo shaker on the mixture at 185 rpm, 40° C. and 20 minutes. Next, we add 80 ml of ethanol to the mixture and we rise the temperature to 60° C. and the shaking to 235 rpm. The reaction is maintained for 24 hours at atmospheric pressure, under an inert atmosphere (nitrogen). The mixture is then cooled to room temperature and the resin or catalyst is recovered by filtration of the oil. The ethanol is eliminated, obtaining a triglyceride mixture. From the sample obtained for its analysis by GC-MS we determine that the oil obtained contains less than 0.4% of free fatty acids with a DHA concentration 470 mg/g and PhA <90 µg/g.

b) Non-Pycnic Centrifugation (in Density Gradient without Equilibrium).

2. Ultracentrifugation

From the remaining oil obtained during process (a) stages 1 and 2 of the example, 491 gr of acidified oil are centrifuged at 150 rpm for 20 minutes forming a solid phase or stearine (267 gr) and a liquid phase, containing the free fatty acids, is vacuumed. This liquid phase is added to a glycerol gradient, prepared as specified on stage 3 of example 1 and it is centrifuged at 100000 g× for 24 hours without reaching equilibrium.

3. Separation by Crystallization of the Omega-3 Fatty Acids.

We proceed to directly cool the oil contained in the cylinder of the centrifuge at −30° C. for 24 hours. As a result, a solid phase is generated, 85 g, which contains the saturated, monounsaturated fatty acids and the PhA and a liquid phase, 145 g that contains the omega-3 fatty acids. The liquid fraction is separated through the opening at the base of the cylinder.

As a result of this procedure and through a GC-MS analysis of the liquid phase, we determine that the product obtained contains a purity of omega-3 of 92.4% and PhA levels <90 µg/g.

4. Esterification of Fatty Acids Free of Triglycerides.

To esterify the free fatty acids obtained at the previous stage, just like in the Example 1, the method described in the patent US 20080114181 is used. Using a Soxhlet condenser, we mix the styrene resin at 5% and the free fatty acids (200 g) and glycerol (50 g) introducing a mechanical thermoshaker on the mixture at 185 rpm, 40° C. and 20 minutes. Next, we add 80 ml of ethanol to the mixture and rise the temperature to 60° C. and the shaking to 235 rpm. The reaction is maintained for 24 hours at atmospheric pressure. The procedure takes place under inert atmosphere (nitrogen). The mixture is then cooled to room temperature and the resin or catalyst is recovered by filtration of the oil. Ethanol is eliminated by heating the oil at 90° C.

From the sample obtained for its analysis by GC-MS, it is determined that the oil obtained contains less than 0.6% of free fatty acids with a DHA concentration 440 mg/g and PhA <90 µg/g.

In this Example 2, as the starting product contained a lower amount of DHA, the final product also contains a lower amount of DHA. Even so, we can conclude that from this procedure we have been able to obtain 4 times the DHA quantity (from 110 mg/g to 440 mg/g) and reduce PhA 200 times. After repeating the process using the obtained product as starting product, a composition with 740 mg/g of DHA and less than 90 μg/g PhA is obtained.

Example 3

Product Analysis

In order to determine the total amounts of fatty acids we have performed the following analysis:
i) Analysis of the Fatty Acids by Gas Chromatography-Mass Spectrophotometry (GS-MS):
Reagents: ethanol 96%, petroleum ether, hexane, methanol, 0.8 mol/L KOH (Sigma-aldrich).
Instrument: Agilent HP 6890 Series GC SYSTEM—5793 Mass selective detector; HP Analytical CD-ROM MS Chemstation Libraries Version A.00.00.
Procedure: 50 mg of fatty acids inside a 10 ml test tube were mixed and shaken in an ether and hexane mixture (2:1), 5 ml of methanol, and 1 ml 0.8 mol/L KOH. We added water and centrifuged at 3000 rpm for 10 minutes. The supernatant was dismissed and the analysis by GC/MS is carried out.
GC/MS: Chromatographic column HP-1.17 m×200 μm×0.11 μm. Injector temperature: 280° C.; interphase temperature: 290° C.; speed: 5° C./min from 100° C. to 260° C.; helium column with flow of 0.9 ml/min; sample from the injector: 1 μl; ionizing source temperature: 230° C.; electrode temperature 150° C.
ii) Analysis of the PhA by Gas Chromatography (GS):
EXTRACTION: In a screw tube add 1 ml of sample, 9.5 ml of chloroform/methanol (2:1) and 2 ml of KCl, shake in a vortex and centrifuge 20 minutes at 3000 rpm. Separate and discard the top layer (aqueous), filter with filter paper on sodium suphate. Recover the filtrate (organic phase) in a tube with a screw top and evaporate.
DERIVATISATION: Add to the dry extract 1 ml of boron trifluoride in methanol, heat at 100° C. during 30 minutes and cool down the tubes. Add 3 ml of water and 3 ml of n-hexane, shake and leave it to rest. Separate and keep the top layer, add to the aqueous layer 3 ml of n-hexane and shake. Gather the organic phases, filter with filter paper on sodium suphate, evaporate until dry and dilute the sample with n-hexane, inject 2 mcl.
INSTRUMENTS: Agilent Technologies gas chromatography 6890N with flame ionisation (FID). Column: TRB-WAX 30 m 0.25 mm 0.5 mcm. Standar: Phytanic acid ester methylic (Sigma). Reactive derivatizante: Boron Trifluoride 20% in methanol (Merck). Chromatography programme: Oven temperature: 205° C. Injector temperature: 250° C. Detector temperature: 260° C.
iii) Analysis of the Product Obtained a Result of the Procedure Described in the Example 1.

The product obtained in Example 1 was analysed by GC-MS for fatty acids and PhA.

The total % of omega-3 fatty acids obtained from the analysis is the sum of DHA+EPA+SDA+DPA. The composition comprises other omega-3 fatty acids in very low or non-detectable fractions due to the technique, which are not taken into account neither in the pharmacopoeiae nor the analysis (i.e.: C28:8,n3).

| | Specification | | |
|---|---|---|---|
| Test | Low limit | high limit | Result |
| Absorbance 233 nm | 0.00 | 0.73 | 0.21 |
| Colour | 0 | 5 | 2 Gardner |

-continued

| | Specification | | |
|---|---|---|---|
| Test | Low limit | high limit | Result |
| Anisidine Index | 0 | 20 | 12 |
| Acidity Index | 0 | 2 | 1.23 mg KOH/g |
| Totox Value (Total oxidation index) | 0 | 26 | 11 |
| Peroxide Value | 0 | 5 | 2 mEqO2/kg |
| Cholesterol | 0 | 1 | 0.1 mg/g). |
| DHA | 720 | 1000 | 740 mg/g). |
| EPA | 0 | 150 | 123 mg/g). |
| Other Omega-3 | 0 | 50 | 46 mg/g |
| Total Omega-3 | 87.5 | 100 | 909 mg/g). |
| Other polysaturated fatty acids | 0 | 1 | 0.6 mg/g |
| Saturated fatty acids | 0 | 1 | <1 mg/g |
| Monosaturated fatty acids | 0 | 1 | <1 mg/g |
| PhA | 0 | 5 | <5 μg/ml |
| Pristanic acid | 0 | 2 | <2 μg/ml |
| Excipient: Tocopherol based antioxidant | 2500 | 4000 | 3000 ppm |

Thus, the proportions of the obtained composition are:
Fatty acids: 91.75%
Of which 80.65% are DHA, 13.38% EPA, 5.07% other omega-3, 0.69% other polyunsaturated, 0.08% are other saturated and 0.08% monounsaturated. The % of PhA and PA impurities is <0.000005% and <0.000002% respectively.
Other non-saponifiable lipids 0.1%
Glycerol (sterified) 8.1%
Ethanol (sterified) 0.11%
Excipients: tocopherols (3.5 ppm-0.000003%)
Heavy impurities, dioxins . . . (<0.000001%)
iv) Benzoapyrene Toxic Analysis (GC-MS):
Thermo-Finnigan AS 2000 in a 5-mm ID Focusliner (Restek, USA) and software Xcalibur 1.2 (ThermoFinnigan Corp.). Chromatographic column 30 m×0.25 mm (ID)×0.25 mm, Rtx-5 ms (Restek, USA). Injector temperature: 280° C.; interphase temperature: 285° C.; speed: 25° C./min from 75° C. to 150° C.; at a speed of 4° C./min until 265° C.; and finally at a speed of 30° C./min until 285° C. Helium column with a flow of 40 cm/seg; injector sample: 1 μl; temperature of ionization source: 200° C. We operated in an ion selective mode (ISM) with an emission of 250 mA and a voltage at 70 eV and an ion monitorisation m/z ±0.5. For the quantification of oil samples we used 20, 50, 100, 500, 1000 ng/ml benzopyrene. For internal control we used perilene-d12 (200 ng/ml).
v) Toxic PCB Analysis and Furan Dioxines (PCDD/Fs).

An immunoassay is performed to determine the PCB and related substances as well as the Furan dioxines using a PCB1 and DF1 immunoassay kit from CAPE technologies. For this a simplified method (Harrison and Carlson, 2000) is applied.
vi) Toxic Analysis of Heavy Metals:

We take 6 samples of acidified oil and we weight 1 g in each one of them on a porcelain crucible of known weight. We mineralize the oil by calcination in a muffle furnace followed by an acid digestion by atmospheric pressure. The analytical method used was the differential anodic impulse voltametry (DPASV) with anionic redisolution with dropping mercury electrode, applying a differential power stripping between −1150 and 75 mV. We also used the hydride generation atomic absorption spectroscopy (HGAAS) for the arsenic and cold vapor for the mercury. The lichen Evernia prunatri L (IAEA-336) was the reference material, following at all times the methods and criteria under the norm in force (DOCE, 1990). We used the software for statistics SPSS 12-0 for Windows XP performing the test for independent simples and ANOVA of a factor.

vii) Toxic Analysis of the Product Obtained in Example 1

| Toxicology | low limit | high limit | Result |
|---|---|---|---|
| Arsenic | 0 | 0.1 | <0.1 ppm |
| Lead | 0 | 0.1 | <0.1 ppm |
| Mercury | 0 | 0.1 | <0.1 ppm |
| Cadmium | 0 | 0.1 | <0.1 ppm |
| PCBs | 0 | 0.09 | <0.09 ppm |
| Furan dioxins (Tec.-OMS) | 0 | 1 | 0 pg |
| Benzopirene (A) | 0 | 2 | 2 µg/kg |

Example 4

Final Product Encapsulation

For oral consumption we can make soft gelatine capsules (gelatine, glycerol, water) without dismissing other soft vegetal capsule technologies to encapsulate oils. Another possible composition for the capsules is to add (>95%) flavour enhancers to the oil (i.e.: 5-6.5% of lemon essential oils) to fill chewable soft capsules (i.e.: covered in 'swatches' gel 1.5%-2.5% lemon). With a final analysis of: Energy: 14.7 Kcal; Proteins: 0.283 g; Carbohydrates: 0.170 g; Fats: 1.4 g; DHA: 1 g Emulsions with water or another hydrosoluble substance can also be made mixing them with flavour enhancers to be consumed as a drinkable liquid and to prepare liposomes. The final product can also be obtained as a powder. Other uses different to oral consumption are possible, particularly as intravenous and intravitreal injections as isotonic emulsions. (saline solution).

The final product of this patent is the development of a supplement and medicament containing 100% liquid oil obtained in the Example 1 in a transparent gelatine soft capsule, size 24 oblong (composition: Gelatine, glycerol, water) containing 1389 mg of oil of which 1000 mg are DHA. It is also possible to use capsules with a gastroresistant coating.

This formula can contain cofactors essential for the treatment of Pigmentary retinosis, such as: Taurine, Beta-alanil-L-zinc histidinate, Lipoic acid, Ester-Ascorbate, Pigments: a) Zeaxantine dipamitate (ES Lycium barbarum), b) delfidinine (ES Vaccinium mirtillus with a low content in cianidine), Myricetine, Naringenine, Hesperitine and their glycosides, Asiaticoside, Ginkgoflavonglycosides A+B; and epigallocatechin gallate, vincamine derivatives.

i) Cofactors Used

| Aminoacids, minerals, vitamins, coenzyme | Min. Dosis per day | Max. Dosis per day |
|---|---|---|
| L-Taurine | 250 mg. | 1000 mg. |
| L-Carnosine (Beta-alanyl-histidine zinc) | 90 mg | 375 mg. |
| N-acetyl cisteine | 100 mg | 400 mg |
| Reduced glutathione | 12.5 mg | 50 mg |
| Acetyl-L-carnitine | 50 mg | 200 mg |
| Elemental slenium (Seleniomethionine) | 37.5 µg | 150 µg |
| Elemental zinc (Glycinate zinc) | 7.5 mg | 30 mg |
| Copper (gluconate) | 25 mcg | 100 mcg |
| Retynol palmitate (A) | 0.5 mg | 0.5 mg |
| Colecalciferol (D) | 5 mcg | 5 mcg |
| Ester-C calcium ascorbate (C) | 250 mg. | 1000 mg. |
| α tocopheril succinate (E) | 25 mg. | 100 mg |
| d-Biotine (H) | 1 mg | 1 mg |

-continued

| Aminoacids, minerals, vitamins, coenzyme | Min. Dosis per day | Max. Dosis per day |
|---|---|---|
| Pyridoxine HCL (B6)* | 62.5 mg | 250 mg. |
| Cianocobalamine (B12) | 25 µg | 100 µg |
| Nicotinamide (B5) | 62.5 mg | 250 mg. |
| Niacine (B3) | 12.5 mg | 50 mg |
| Tetrahydropholate (B9) | 100 mcg | 400 mcg |
| Thiamin chlorhydrate phyrophosphate | 25 mg. | 100 mg |
| Lipoic acid | 25 mg. | 100 mg |
| Dihydrolipoic acid | 100 mg | 400 mg |
| Coenzyme Q10** | 25 mg. | 100 mg | ii) Extracts Used

| Stardard plant extracts | Active substance | Max. Dosis per day |
|---|---|---|
| ES *Daucus carota* | β-carotene | 90 mg |
| C. Carotenoid: | Lutein | 22.5 mg |
| Neo-Life Dynamite (GNLD) | Zeaxantine | 22.5 mg |
| | Licopene | 37.5 mg. |
| ES *Vaccinium mirtillus* L (Wild: *V. angustifolim* Aiton) (1) Antho 50 ® (Antocianosides 50%) Preferably >80% | Antocianosides (15 difer.) Delfinidine glucosides (30%) Myricetine glucosides | 750 mg 450 mg As Std. |
| ES *Lycium barbarum* L Polysaccharides LBP HPLC (2) (20-90%) | Polysaccharides Zeaxantine dipamitate Betaine | 750 mg 40 mg As Std. |
| ES *Vinca minor* L (3) | Brovincamine fumarate Vinburnine Vincamine | 145 mg 15 mg 120 mg |
| ES *Ginkgo biloba* L (EGb 761 extract 50:1 24% Ginkgoflavonglucosides) | Ginkgoflavonglucosides A + B Myricetine glucosides | 180 mg As Std. |
| ES Asian centella (40%-90%) Asiaticoside HPLC) | Asiaticoside | 90 mg |
| ES *Eucommiae ulmoides* cortex 60% ligninoglycosides (4) | Aucubine | 60 mg |
| ES *Equisetum arbense* 60% esteroles | Campesterol | 30 mg |
| ES *Myrica rubra* (o carolinensis) (4) | Myricetine glucosides | As Std. |
| ES *Solanum melongena* var. Marunasu L (Nasunin) | Delfinidine glucosides | As Std. |
| ES *Camellia sinensis* 98% Polifenoles 80% EGCG cafeine <0.5% HPLC | Epigallocatequine gallate (EGCG) | As Std. |
| ES *Citrus paradisi* L (4) | Naringenine glucoside (3 hydroxi-grups) | As Std. |
| ES *Citrus aurantium* L (4) | Hesperitine glucoside (3 hydroxi-grubs) | As Std. | iii) Analysis of Relevant Active Substances

| Fitochemical substances | Min. Dosis per day | Max. Dosis per day |
|---|---|---|
| Asiaticoside | 22.5 mg | 90 mg |
| Delfinidine glucosides | 175 mg | 700 mg |
| Epigallocatequine gallate (EGCG) | 50 mg | 200 mg |
| Ginkgolide A | 18.75 mg | 75 mg |
| Ginkgolide B | 26.25 mg | 105 mg |
| Myricetine glucosides | 50 mg | 200 mg |
| Polysaccharides LBP-x (*Lycium* sp.) | 187.5 mg | 750 mg |
| Vincamine | 30 mg | 120 mg |
| Total zeaxantine (like dipalmitate 57%) | 17.5 mg | 70 mg | iv) Analysis of Other Active Substances in the Composition

| Fitochemical substances | Min. Dosis per day | Max. Dosis Per day |
|---|---|---|
| Total luteine | 30 mg | 30 mg |
| Beta Carotene | 100 mg | 100 mg |
| Brovincamine fumarate | 145 mg | 145 mg |
| Vinburnine | 15 mg | 15 mg |
| Betaine | — | — |
| Acubine | 60 mg | 60 mg |
| Campesterol | 30 mg | 30 mg |
| Total flavonoids | 3500 mg | 3500 mg |
| Total anthocianidines | 1200 mg | 1200 mg |
| Total flavonols | 600 mg | 600 mg |
| Quercetine glucosides | 150 mg | 150 mg |
| Total flavones | 300 mg | 300 mg |
| Routine | 100 mg | 100 mg |
| Total flavanols | 400 mg | 400 mg |
| Total flavanons (4) | 1500 mg | 1500 mg |
| Naringenine glucosides | 200 mg | 200 mg |
| Hesperitine glucosides | 200 mg | 200 mg |
| Narirutin (naringenin-7-rutinoside) | 300 mg | 300 mg |
| Hesperirutin (hesperitin-7-rutinoside) | 300 mg | 300 mg |

Through different mechanisms the different glucosides of this composition (i.e.: delphidine and myricetine) increase the DHA concentration in the retina and photoreceptors and inhibit apoptotic photoreceptors caused by light (Laabich et al., 2007).

Example 5

Experiments to Determine the Inhibitor Activity of DHA and its Mechanisms According to PhA, Whether In Vivo (Oral Administration) or In Vitro A) Experiment A: Paraquat-Induced Photoreceptor Apoptosis Tyramide signal amplification (TSA)-FISH PerkinElmer, Boston, Mass., USA.); secondary antibodies, monoclonal antibodies to-Bax (sc-7480), Bcl-2 (sc-7382), rodopsine RET-P1 (sc-57433) (Santa Cruz Biotechnology, Inc.—USA), PhA, Docosahexaenoic acid, Paraquat Dichloride, (Sigma-Alldrich). Solvents and reactors had HPLC and analytic grade.

Purified cultures of neurons from Wistar albino rats were prepared according to Politi et al., (1966) and treated in a poli-ornithine medium as in Adler-R (1982). On the first day of culture, equal concentrations of DHA (9 mM) were added to neuron cultures, with 7 different concentrations of PhA (/5/20/100/500/2500 and 12500 µgPhA/g oil), usually found in marine origin oils rich in DHA, and 2 controls without DHA, with or without Paraquat. On the third day of culture, Paraquat was added, incubating it for 24 h before fixing it for an hour with paraformaldehyde in a phosphate buffered saline (0.9% NaCl in 0.01 M NaH2PO4 [pH 7.4], following 15 minutes with Triton X-100 (0.1%). In the apoptosis, the expression of Bax and Bcl-2 was determined and quantified according to the method Rotstein-N P et al. (2003). For the cytochemical studies, 10 fields/samples were randomly quantified, where results represent the of 3 samples/plate mean for each concentration of DHA with PhA.

Figure 1:
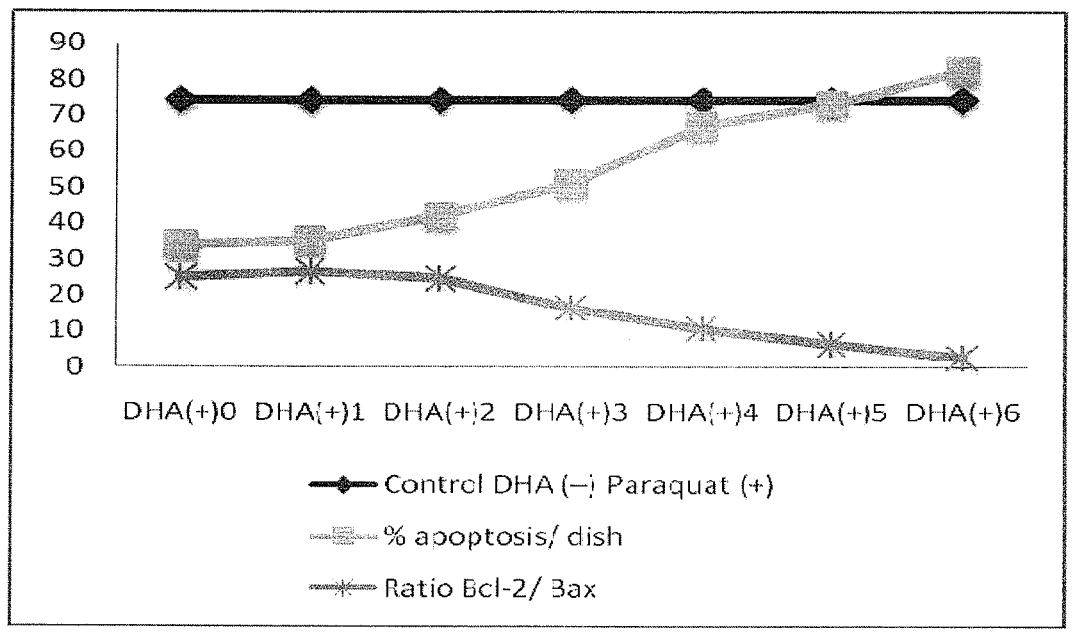
FIG. 1. Capacity of inhibition of photoreceptors apoptosis (%) by DHA induced by Paraquat in vitro at different concentrations of PhA (blue) and Bcl-2/Bax index (green). The red line shows the degree of apoptosis without treatment with DHA. In this experiment it can be clearly seen that DHA oils <5 µg/g of PhA have a greater inhibitory activity of apoptosis than those with larger concentrations and the oxidative stress produced is also less. This determines that DHA <5 µg/g in vitro, has a higher physiologic activity for the treatment of retinal dystrophies as an inhibitor of apoptosis.

Anti-apoptotic capacity in photoreceptors of DHA is inversely correlated to PhA concentration (PhA) (FIG. 1). The greater anti-apoptotic activity can be obtained by using DHA in concentrations of 0 and 4 µg/ml of PhA, were no significant differences are detected. Anti-apoptotic activity in oils with DHA with 0 and 4 µg/g of PhA is notably higher than in oils with DHA with concentrations of ≥20 µg/g and ≥100 µg/g of PhA, respectively, where the anti-apoptotic activity of DHA is significantly reduced. At PhA concentrations of 2500 mg/g the activity to inhibit apoptosis of photoreceptors is neutralised, and at higher concentrations apoptosis of photoreceptors is induced despite the DHA presence. Bcl-2/Bax index, besides being inversely correlated to apoptosis of photoreceptors and the oxidative stress, indicates that DHA in concentrations ≤20 µg/g have significantly less oxidative stress than concentrations ≥100 µg/g.

B) Experiment B: MNU-Induced Retinal Apoptosis

The same materials and immunohystochemical and quantification methods as in Experiment A were used. Instead of using Paraquat for inducing apoptosis, N-Nitroso-N-methylurea (MNU) (Sigma-Alldrich) was used. Instead of analysing cultures in vitro, as in Experiment A, retins from sacrificed Wistar albino rats were analysed. For that purpose, 8 rats S-D with 42 days of age were selected and fed for 4 weeks with a standard basal diet. Each animal was fed in a different way: one rat was on a standard on control diet, while for the other 7 rats this diet was modified with DHA at 15%, having different concentrations of PhA as in Experiment A: 0/4/20/100/500/2500/12500 µgPhA/g of oil. After these 4 weeks, they were injected a single intraperitoneal injection of MNU (75 mg/kg body weight). All rats were on the same diet for 6 days, being sacrificed at the $7^{th}$ day, after having fast for 24 hours, when the extraction of retinas was carried out, following the fixation and immunohystochemical processes as in Experiment A. For the cytochemical studies, 10 fields/samples were randomly quantified, where results represent the 10 eye/sample mean.

Figure 2:
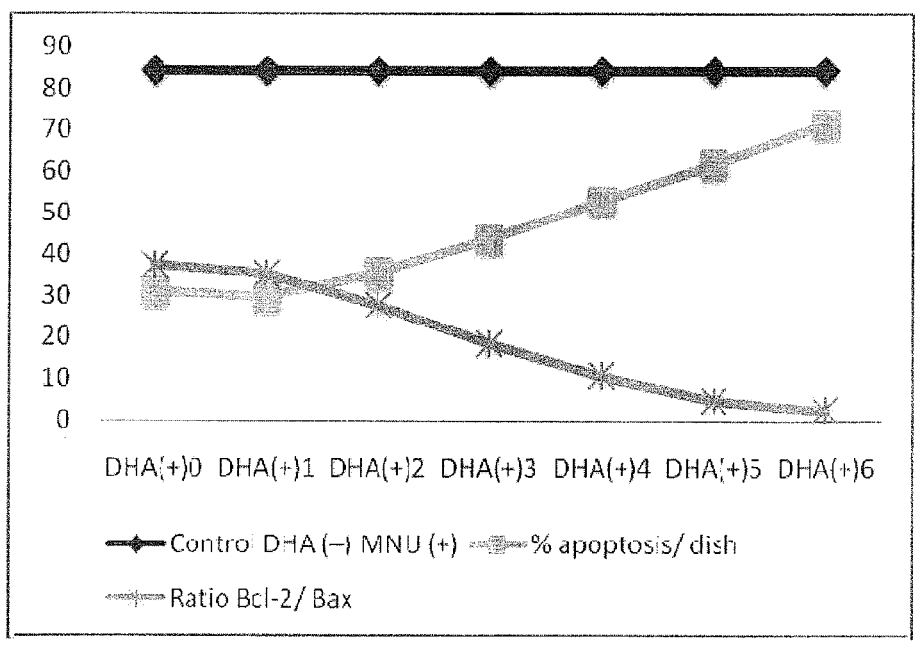
FIG. 2. Capacity of inhibition of photoreceptors apoptosis (%) by DHA induced by MNU in vivo at different PhA (blue) concentrations and Bcl-2/Bax index (green). The red line shows the degree of apoptosis without treatment with DHA. This experiment confirms the observations seen in vitro, concluding that the oral consumption of DHA <5 μg/g of PhA has a greater physiological activity for the oral of retinal dystrophies as an inhibitor of apoptosis.

As results in vitro revealed (FIG. 1), anti-apoptotic capacity of photoreceptors of DHA is inversely correlated to concentration of PhA. The behaviour of the concentration of PhA in oils with DHA in vitro is also comparable to that observed in vivo (FIG. 2). The greater anti-apoptotic activity is obtained in concentrations between 0 and 20 µg/g, where there are no significant differences but, as it was the case with in vitro levels of 20 µg/g of PhA, the ratio Bcl-2/Bax is significantly lower among rats fed with <5 µg/g. There is no neutralisation of the inhibitor effect of the apoptosis of DHA. Rats fed with DHA <5 µg/g do not reveal alterations in the anti-apoptotic activity and markers Bax and Bcl-2 with regards to DHA without PhA added.

These two examples confirm both in vivo and in vitro, that DHA free from PhA is more efficient and safe in the treatment of degenerative diseases such as RP, than many of the market DHA brands with high levels of PhA. These examples describe decisive mechanisms of action of DHA in diseases described throughout this patent and how PhA interferes in its effect. This is all in agreement with the numeorus epidemiologic evidences and molecular and pre-clinical studies on the deleterious effect of PhA and it's antagonist effect with DHA. The activity of DHA free from PhA in neurodegenerative diseases, urogenital, musculo-skeletal diseases, cardiovascular diseases and the applications described in this innovation, is greater than that of other commercial DHA's due to the antagonist effect of PhA as described in this innovation and particularly in the mitochondrial and anti-apoptosis activity observed in these examples.

Example 6

Use of a Composition with a High Content of DHA and Free from PhA for the Clinical Study of Retinosis Pigmentosa For the first time ever in this study, high frequencies of several alterations were found such as: sublinical auditive alterations, severe cardiovascular (arrhythmias), prostate, hypertension, diabetes and thyroiditis in RP patients without associated syndromes.

Over the last decades it has been found that docosahexaenoic acid (DHA) is reduced in RP patients, where PhA is increased in part of them. Different intervention studies with animals suggest benefits of DHA under controlled levels of PhA. DHA is essential for the survival of photoreceptors and for phototransduction.

In order to determine whether the intake of DHA with PhA <5 µg/g at a dose beyond the nutritional one, could treat RP and what kind of clinical advantages it could have, a clinical trial was carried out following an intervention randomised cross-over double-blind study. 40 patients with RP were randomly chosen, with an average age of 46 years (17-70). The following tests were undertaken: electroretinogram, visual evoked potentials (VEP), automated perimetry, visual acuity (VA), audiometer, standard and clinical ophthalmologic examination, blood test haemostasis and fatty acids. An intervention randomised cross-over double-blind study was carried out with two groups (A and B) that were treated with an oral dose of 740 mg/day (twice the nutritional dose) of drinkable DHA and with less (<0.20 mg of PhA) during 10 months, each with a control in the life style habits. Upon termination of this first phase of the study, both groups were crossed over and the same intervention was repeated again in a second phase.

Results: Before starting the study, 61% of patients had abnormally high EVP with macular atrophy. 81% of the eyes had a visual field <10° from which 35.5% had a VA ≥0.5 (20/40). Patients with legal blindness according to VA values represented 25.8%. A 6.4% had a VA <20/200. The average VA was 0.41±0.22. In RP patients 48% have a VA ≤20/40 increasing to 62.5% beyond 60 years with an average VA of 0.39±0.21. A yearly reduction on VA of 0.06 is produced. A sub-group of patients (n=8) showed high levels of PhA and had a VA ≤0.2. This sub-group represented the only patients with RP where treatment with DHA did not result in an improvement in VA. In the remaining patients (n=32), which had normal levels of PhA, treatment with DHA resulted in a significant increase of VA of 0.055 and 0.119 in groups A and B. All the hereditary forms of dominant autosomic RP, simple, autosomic recessive, and sporadic had an increased in VA: 0.104, 0.091, 0.068 y 0.025 respectively. Eyes with VA1≤0.2, VA2=02-0.5, VA3≥0.5 increased on a proportional manner their AV by 0.02, 0.08 and 0.13 respectively. In such patients with normal levels of PhA, changes in the visual field were also observed although there was not a significant increase of the foveal and parafoveal sensitivity (5.3%, 9.8% respectively) in group A; and (6.6%, 11.3% respectively) in group B. In both groups, levels of HDL1 cholesterol increased by 30%.

RP patients have a high incidence of cardiovascular diseases, diabetes and hyperthyroidism. No adverse effects were found. Visual function seems to be more related with the age of onset of the symptoms than with the age of the patient as well as with the concentration of PhA. The dominant type has a better prognosis than the recessive one. The sub-group with high levels of PhA has a worse prognosis and shows no improvement in the VA following treatment with 740 mg/day of DHA. In the sub-group with normal levels of PhA, 76.5% of patients improved their VA regardless of the hereditary pattern. The treatment did not produce improvements in the visual field. This pilot trial seems to show that DHA could be useful in the treatment of at least the function of the central vision and to determine at which dose the retinal dystrophy could be avoided in RP, bearing in mind that a subgroup of patients showed high levels of PhA.

Example 7

DHA Pharmacokinetic and the Effect in Peripheral and Central Visual Function in RP and Tolerability of DHA at 2 Doses: 4 g/Day (60 mg/Kg) and 8 g/Day (120 mg/Kg) Vs. Placebo as Unique Treatment of RP A Randomised, double-blind, placebo-controlled study with a parallel-group, at 24-months double-blind treatment.

Patients (n=18) average age of 42 years (24-68) from the RP Association (AARPE). Out of 21 patients admitted to the protocol, 18 were randomised to the double-blind; however, 3 were excluded from the intent-to-treat analysis because no double-blind assessment was done or their centres lacked patients in all the treatment groups. All 18 patients were evaluated for adverse events. From these, 18 patients completed the treatment. A control of habits and of the DHA and PhA of the diet was carried out. The following tests were undertaken: electroretinogram, visual evoked potentials (PEV), automated perimetry, toxicological and immunological analysis, haemostasis, and fatty acid and oxidation sub-products.

The primary outcome variable (central visual function) was the change in VA average which had increased in 24-months. In the 4 g (0.05) and 8 g (0.06) DHA groups, VA values were significantly greater than for the placebo group (−0.04) (P=0.03 and P<.0.05, respectively); in the second outcome variable (peripheral visual function), there was a change in visual field which had increased 2% and 5% in the 4 g and 8 g DHA-groups vs a decrease of 1.2% in the placebo group (P=0.15 and P=0.23, respectively), although no significant.

The DHA-groups showed an electrophysiologic improvement (reduction in amplitude as well as reduction on the EVP latency). No significant clinical differences were present in the DHA-group. All patients had normal levels of PhA following treatment, except for 1 patient in each DHA-group that had high levels of PhA. Non of the patients had tolerability problems and no adverse effects were observed in the placebo or DHA group. No variations of PhA were observed, except in the two patients with high levels who still had a reduction of 52% and 48% in the 4 g and 8 g DHA-group respectively. DHA did not produce significant alterations in the AA levels and other omega-6 fatty acids, increasing significantly the concentration of EPA in the DHA groups. The increase in DHA in target tissues is proportional to the therapeutic dose, where it was observed that DHA levels were 5.2, 7.3 times higher in phospholipids compared to basal levels. Maximum plasmatic concentrations were achieved between 3 h and 6 h after the oral administration with food of a normal fat content.

Therefore, we can conclude that the composition of the invention DHA is efficient for improving the visual central function in retinal dystrophy, although due to the size of the sample and duration of the trial, it cannot be ruled out benefits in the peripheral visual function of RP patients. It can also be concluded that, DHA is well tolerated as a therapy for RP; the response is clearly dose-dependent.

Example 8

Determine the Efficacy and Safety of the Composition of the Invention in Different Pathologies Associated to Retinal Hereditary Dystrophies In the state of the art, retinal dystrophies include a wide group of diseases amongst which the following can be found: Dominant Autosomic Retinosis Pigmentosa (AD), Dominant Recessive Retinosis Pigmentosa (AR), Simple Retinosis Pigmentosa (SP), Retinosis Pigmentosa Linked to Sex (XL), Stargardt Disease (ST), Choroidemia, Leber etc.

In order to carry out the following study 171 patients were selected, 76 men and 85 women, with an average age of 45 years (8-72) from the file of RP Patients (AARPE). Individuals were separated into to groups. The first group of 97 individuals, 41 males and 56 females (14 AD, 26 AR, 44 SP, 1 XL, 7 ST, 1 Refsum, 1 Kearns, 3 Usher), were treated with 4 g/day of the composition of the invention. The second group of 74 individuals, 35 males and 39 females (9 AD, 24 AR, 34 SP, 4 ST, 1 Leber, 1 Usher, 1 XL), did not receive any treatment. The parameters considered to determine the efficacy of the composition of the present invention in the evaluation of the disease, were the visual acuity (VA) and the visual field (VF). Such parameters were measured throughout the 8 years of duration of the study, once a year.

Significant differences were obtained in the VA and VF for patients treated under group 1, whilst the parameters of the group of individuals not treated remained unchanged or worsened, as corresponds with the normal progression of the disease. In the treated group, there was a difference in the visual acuity after two years, whilst the visual field showed no significant differences until 6 years. The uptake of 4 g/day of DHA improves the visual parameters in RP patients and Stargard disease.

Example 8.1

Linked-X Choroideremia 3 brothers of 9, 13 and 16 years of age with X-linked Choroideremia; showed alterations in the ERG, night blindness, without changes in the VA and the older one exhibited changes in the visual field but with a VF >60° C. They started the treatment with 2 g/day of DHA free from PhA. After 6 months of treatment, they had not normalised the DHA levels in the erythrocytes phospholipids, neither were there variations in the ERG. The dose was then increased to 4 g/day during 6 months, noticing an increase in the DHA levels of phospholipids and photopic changes in the ERG and an improvement of the VF in the 16 year old patient.

Example 8.2

Stargardt Disease 6 patients with Stargardt disease with ages between 21 and 42 years took part of a cross-sectional study (study 3 of RP) previously described. During 8 years, 4 of them took no treatment with the product of this invention (DHA), one of them took it during 8 years and another one took DHA with the cofactor described in the formulation irregularly for 3 years. All the patients who did not received the treatment, had a progressive loss of the VA following the natural progression of the disease, maintaining a VA ≤20/200 in both eyes (AO). Patients who took DHA during 8 years preserved the VA 2/10 AO during such period without any variations. The patient who took the treatment with DHA and the formulation during 6 months, improved the VA from 1/10 AO to 3/10 AO. However, upon interruption of the treatment, the VA worsened, with a VA of 1/10 two years after receiving the treatment. The patient, took up again the treatment until the present days (2.5 years) increasing the VA to 2/10.

Example 8.3

Hereditary Retinoschisis

Two brothers of 11 and 13 years were diagnosed of retinoschisis showing at the time of diagnosis a VA of 4/10 AO and 6/10 AO respectively. They started taking voluntarily 3 g/DHA from this invention during 31 moths, preserving a VA of AV of 5/10 and 8/10 by the end of the treatment.

Example 9

Use of the Composition of the Invention for Treatment of Retinal Dystrophies Non Associated to Genetic Disorders DHA increases the neuronal resistance under ischaemic conditions, reducing the optic atrophy in neuropathies and retinal dystrophy in vasculopathies. Besides the antiapoptosic effects of DHA, it has an inhibitory effect over the F2 prostaglandins. Drugs for glaucoma and to control the intraocular pressure (IOP) are analogue to DHA, acting as vasoconstrictor prostanoid receptors antagonists (PGF2). Therefore, the treatment has been proved in patients with proliferative ischaemic retinopathy, neoprostane, optic ischaemic uropathy and demyelinising, diabetic microangiopathy, age related macular degeneration both humid and dry, glaucoma and myopia magna. The description of each case is long. Some need to be typified, but in all cases there was an improvement of the visual function (measured according to VA and VF) and the maculopathy in fundus oculi examinations, optical coherence tomography (OCT) and angiography. Particularly, in this group of patients, the combination of DHA with the formula previously described, becomes more necessary due to the severe rheologic alterations of the retina and the reduced bioavailability of the DHA in it. Besides, the vascular pathology is the main cause.

Example 9.1

Macular Oedema Secondary to Retinal Dystrophies (Ie. RP) or of Ischaemic Origin: Cystoid Macular Oedema (Irvine-Gass Syndrome). Berlin Scotome 6 patients with ages ranging between 33 and 75 years were diagnosed at least 12 months before of cystoid macular oedema and Irvine-Gass syndrome (CMO) and were treated throughout 12 months with systemic corticoids, Triamcinolone and inhibitors of the carbonic anhydrase (ie. acetazolamide). Neither of them suffered from a known retinal dystrophy. These patients, at least 24 months previous to the Cystoid macular oedema had a AV >8/10. Before receiving treatment with 4 g/day of DHA from this invention, associated with the formulation described in the invention, the VA was of 1/10 and 3/10. The duration of the treatment was of 3 and 12 months.

After 3 months of treatment, all the patients increased their VA. By the end of the treatment, all patients normalised their VA, achieving a VA between 9/10 and 10/10, that in one case was higher to the VA previous to the onset of the cystoid macular oedema which occurred after the cataract surgery.

3 patients diagnosed of RP suffered from CMO. They were treated with the same treatment programme as previously described. The VA before treatment was 1/10, 1/10 and 1.5/10. After 6 months the three cases increased the VA to 3/10, 6/10 y 7/10. The VA before suffering from CMO was 3/10, 5/10, 7/10.

Example 9.2

Haemorrhagic Pars Planitis

An 8 year old girl with 32 kg of weight was diagnosed of haemorrhagic pars planitis. Three months after the diagnosis with no positive changes in the clinical progression, it is decided to have a surgical intervention. 10 days before the intervention she receives treatment with 3 g/day of DHA of this invention until 24 hours before surgery (9 days). In the study previous to the surgery, the clinical improvement observed by the specialist, resulted in a delay of the surgery by 30 days. She then took a treatment with 3 g/day of DHA with PhA levels below 5 ug/g during 30 days, observing a complete remission and normalisation of the visual function.

Example 10

Supra-Physiologic Effect of the Composition of the Invention in the Visual Function of Healthy Patients In healthy people, DHA increases the phototransduction and the regeneration of the rhodopsin. 32 healthy individuals without retinal dystrophy between 18 and 45 years of age, without emetropic or hypermetropic alterations, received treatment with 4 g/day of DHA free of PhA during 6 weeks and the VA were studied before and after treatment.

All the individuals showed a VA at the beginning of the treatment of 10/10. After 6 months they all had a VA beyond one (20/16). In two cases there was an astigmatism 0.0 in both eyes. In 9 people the VA exceeded 20/12. All of them increased their night adaptation (adaptometry).

It has also been detected an increased in VA in healthy individuals with myopia without altering the optic graduation. In young individuals with a developing myopia and in individuals with myopia magna, there is a stoppage of the myopia after a 10 year follow up.

Example 11

Use of the Composition on the Invention for the Treatment of the Allergic Condition, Eye Surface and Dry Eye Disorders The effect of DHA in the eye surface gives a mechanical protective and nutritional effect, chemical protection and an antiseptic effect. DHA exerts a neurologic, hormonal, immunologic and anti-inflammatory control prostaglandins). DHA plays an active role in the organisation of the lachrymal lipid film, reducing the evaporation of the muco-aqueous phase, reducing the surface tension of the inter-phase and as antibacterial. It inhibits apoptosis and controls the secretion of the Goblet cells. It normalises the lipid secretion and viscosity of the Meibomio glands. DHA acts in all types of dry eye diseases: allergies, hormonal (androgenic), infections and metabolic-dietetic in the composition of fatty acids. DHA inhibits the formation of dihydroxitestosterone in the lachrymal glands, increasing at the same time the androgen levels. This prevents the apoptosis of the lachrymal glands, necrosis and inflammation. DHA exerts an efficient control in the chronic inflammation, allergy and corneal oedema, since it inhibits the synthesis of leukotrienes (76%), reduces the platelet PAF, prostaglandin E2 (40%), reduction of prostaglandin F2 (81%), and controls the TNF, interleukins IL-6 and IL-1b.

50 patients between 20 and 43 years old without retinal dystrophy and myopia <9 diopters, were given a dose of 4/g day of DHA as a pre-Lasik treatment one month before undergoing myopia surgery. A pachymetry was carried out and before surgery it is observed an average increase of 12.4%. In some cases, the pachymetry before the treatment and after surgery was similar or slightly higher.

Example 12

Treatment with the Invention Composition as a Coadjuvant in Neurology and Psychiatry Besides the genetic pathology with neurological disorders previously described, DHA is deficient in diseases with alimentary disorders, having a determinant role both in its clinical evolution as well as in the remission such as with anorexy and bulimy, as well as in mental schizotypic disorders, personality disorders, primary attention disorders. Through numerous observational and intervention studies, it has been seen that DHA reduces depression, agressivness, primary attention deficit, increases memory, improves learning abilities and reduces the risk of suffering from Alzheimer. DHA accumulates in the brain and in the neural tissue, and the cerebral cortex is the area of the organism where it is more preserved. Its role in increasing the synapsis, in the inhibition of apoptosis in ischaemic conditions has been extensively studied.

A total of 30 individual cases have been studied for the treatment of the spasticity with 4 g/day, 8 g/day 15 g/day of DHA without PhA in multiple sclerosis and spinal cord disorders: spinal ischaemia, spinal tumor, transverse myelitis, cervical spondylosis, brain paralysis or degenerative mielopathy.

In all the cases studied, a significant reduction was obtained with remissions of the spasticity, muscular rigidity, improvement of motility and reduction on pain due to spasticity. All patients had a long history, clinical follow up and were being treated pharmacologically (ie. baclophen, interferon, etc.) during a period of not less than 2 years, exhibiting at the beginning of the treatment a bad clinical situation in the spasticity and mobility. Results show that the treatment is dose dependent, that is, those patients who received higher doses (15 g/day) had a faster clinical response (before 7 days), increased mobility and remission of the spasticity on a faster or efficient way than patients treated with lower doses (4 g/day). The three doses studied resulted in improvements of the spasticity.

Example 13

Treatment with the Composition of the Invention as a Coadjuvant in Oncologic Therapy The support offered by DHA free from phytanic acid as a coadjuvant in oncology is very significant, considering that PhA is a tumoral risk factor in tumors with the highest prevalence. PhA increases the tumoral activity, exhibits pharmacological interactions, and possibly a greater cardiovascular mortalily. Currently, DHA is already included as an antitumoral treatment (ie. Prostate cancer with placlitaxel) due to the numerous benefits that offers, such as the inhibition of angiogenesis, induction of apoptosis in numerous tumor lines, reduction of relapses in tumoral lines etc. DHA without PhA is a cofactor in oncology since:

a) It inhibits angiogenesis on a very efficient manner through different mechanisms: control of the prostaglandins metabolism in tumours and potent inhibitor of the VEGF, reduction of the intensity of pains, improvement of the antiinflammatory effect of antiinflammatories and analgesics, allowing lower doses and reducing its secondary effects.

b) Induces apoptosis in numerous tumoral cells, increasing the cytotoxicity of other cytostatic and antitumoral treatments at lower doses. Reducing the cytotoxicity of the antitumoral treatment, increasing its efficacy and allowing longer treatment cycles.

c) Whilst it induces apoptosis in the tumor lines in adenocarcinoma of lung, prostate, colorectal etc. it also improves the function of healthy tissues in lungs, heart, prostate etc., significantly improving the quality of life of patients.

d) DHA free from PhA directly reduces the cardiotoxicity, neurotoxicity and hepatotoxicity. It has also been related to a lower hematopoietic or medular toxicity.

e) DHA reduces relapses of the most prevalent tumoral lines (colorectal cancer, prostate, breast, lung, ovary, gastric, esofagic etc.)

DHA without PhA used with retinoids, are coadjuvants in treatment of lung adenocarcinoma, particularly because the absence of PhA would not induce added toxicity to retinoids. Retinoids and DHA have a synergic activity in certain lung cancers, mieloproliferative and colorectal cancers amongst others. DHA has been established as a chemopreventive in lung (Serini et al., 2008), colon cancer etc. Particularly, statins are also a chemopreventive agent and also this invention uses its association. Particularly because PhA induces interactions with statins. DHA and statins have a potential effect as chemopreventive treatment in numerous and main tumors with a great epidemiological value. Their epidemiological value, still to be assessed, leads to think that currently they are important agents in the reduction of the number of cases, severity and prognosis, reduction of metastases, an increase of the therapeutic posibilities, delay in the evolution and in the prevention of relapses. Particularly DHA, since it does not induce secondary effects or an added risk to the population, has other important preventive effects of great epidemiological value with age (diseases that result in blindness and dementia) and particularly since it is the only nutrient which is deficient in the general population.

As an illustrative example, although not limiting, a description is given of a case of a patient with lung adenocarcinoma with more than 20 metastases in lung of less than 1 cm, as well as in bones and liver. The 2 years of history of antitumoral treatment prior to taking a DHA treatment free from PhA, showed a worsening with an increase in the number of metastases. Following failure of the 3 first rescue chemotherapy cycles, 12 g/day of DHA without PhA were introduced in the 4° cycle of rescue chemotherapy. In the following control, at 6 weeks, through an abdominal-pelvic TAC, it is informed that there is a remission of the lesions. The 7 cycles of the rescue protocol are finished using as a coadjuvant the compound of the present invention. In controls of the last 3 years, the tumoral activity of the patient remains in remission.

The use of DHA free from PhA as a coadjuvant to the oncologic therapy, improves the clinical conditions of the patients during a longer period and increases the statistics of the life expectancy.

Example 14

Use of the Composition of the Invention in Nephrology and Urology

Treatment with DHA of the nephropathy associated to IgA and the nephropathy associated to Systemic Lupus Eritematous has been described more than a decade ago. DHA inhibits apoptosis of the nephrone, reduces ischaemic renal lesions and is a powerful renal anti-inflammatory substance in inflammatory renal diseases (nephritis, glomerulonephritis). DHA is an ideal coadjuvant for the multi-drug immune suppressive treatment in renal transplant. Dendritic cells, in case of tolerance or rejection, are in charge of presenting the antigens and "the ones that decide whether there is rejection or tolerance". The modulation of dendritic cells by DHA is well known in preventing rejections, Alzheimer, autoimmune diseases, etc.

DHA without PhA particularly reduces the risk of urine infections. As a result of its controlling function over prostaglandins, inhibitory effect over the synthesis of DHT and particularly, because is free from PhA, which is the higher risk factor for prostate cancer, benign prostate hypertrophy and alterations of the prostatic function, it is particularly efficient in the treatment and prevention of benign prostate hypertrophy and in the prevention of the erectile dysfunction. Following is a description of 5 cases in which the efficacy of DHA free from PhA against different nephropathies is demonstrated.

Example 14.1

Nephrotic Syndrome

A 12 year old boy, diagnosed of nephrotic syndrome at 5, controlled with corticoids (15 mg/every two days). In several attempts to cease the treatment, the nephrotic syndrome showed up with serious levels of proteins in urine before 3 weeks. The treatment was suspended and 4 g/day of DHA free from PhA were introduced and a clinical follow up was carried out. After 3 months of treatment, there were no signs of proteins in urine. After suspending the treatment for 3 weeks, symptoms of nephritic syndrome appeared and it was therefore decided to implement the composition of the present invention during 2 additional years at a dose of 4 g/day, remaining during that period with no signs of nephrotic activity.

Example 14.2

Renal Insufficiency Associated to Malign Hypertension

Male patient of 38 years of age, regular consumer of cocaine suffers from an episode of malign hypertension. The blood pressure is controlled and the use of narcotic drugs is eliminated. The patient suffers from an optic atrophy in the left eye and optic neuritis in the right eye, with a visual acuity of 4/10 and renal insufficiency with a creatinine value of 6.9 mg/dl. After 6 months of follow up, where there is an increase in the creatinine from 4.5 mg/dl to 6.9 mg/dl, it is decided to start with dyalisis. Before starting the dyalisis, treatment with 8 g/day of DHA free from PhA is introduced. Two weeks after starting the treatment, the creatinine value was reduced to 4.8 mg/dl and it is decided to postpone the dyalisis. After 6 months with the same regime of DHA free from PhA, the creatinine levels were of 1.8 mg/dl and the visual acuity of the right eye of 10/10.

Example 14.3

Chronic Renal Insufficiency Associated to Lupus Nephritis

Female of 24 years with a history of lupus nephritis since she was 9 and with permanent corticoid treatment and 6 complete treatments of approximately 6 months with myophenolate and cyclophosfamide throughout 18 years. Treatment with 8 g/day of DHA free from PhA is initiated when the creatinine value was 4.6 mg/dl. After 30 days, the creatinine value was reduced down to 3.1 mg/dl. In the one year follow-up, the levels of creatinine were reduced to 1.3 mg/dl. The treatment is then taken for the following two years and the creatinine values remain stable. The treatment is suspended and 90 days after a creatinine of 3.4 mg/dl is observed, so it is decided to restore the treatment with 8 mg/day of DHA free from PhA permanently associated to 1 mg of prednisolone.

Example 14.4

Renal Transplant in Patient with Lupus Nephritis

Female patient of 33 years of age who had a kidney transplant 6 years before, under a stable treatment with a creatinine value of 1.8 mg/dl following a maintenance treatment with Mycophenolate (1 g/day) and Prograf (7 mg/day), suffers a rejection diagnosed through a renal biopsy and with an increase in creatinine to 2.9 mg/dl. Treatment with Prograf is increased and corticotherapy treatment is introduced for six months, without results in the biopsy and with an average creatinine value of 2.4 mg/dl. Treatment with 12 g/day of DHA free from PhA is introduced, verifying after 7 days a reduction of the creatinine to 1.7 mg/dl and reducing the creatinine levels to a minimum of 0.9 mg/dl and an average of 1.1 mg/dl during one year. A renal biopsy is carried out which is negative for rejection and a maintenance treatment is introduced with Prograf (7 mg/day), Mycophenolate (500 mg/dia) and 4 g/day of DHA free from PhA. In the follow up of the next 4 years, creatinine levies remain at an average value of 1.17 mg/dl with no evidence of alterations of the renal function.

Example 14.5

Renal Transplant Non Associated to a Systemic Disease 70 year old female patient, who underwent a renal transplant at 62. Two years after the transplant she suffers two rejection episodes with creatinine values between 2.1 and 2.5 mg/dl. She is treated with corticotherapy. During the 4 subsequent years, the creatinine value stabilises at 1.3 mg/dl. At the 6° year since the transplant, she starts taking DHA free from PhA at a dose of 4 g/day, showing during that period creatinine values between 1.1 y 1.2 mg/dl. After two years of taking this treatment regularly, it was observed in the 6 subsequent months, a reduction in the creatinine levels between 0.97 and 1 mg/dl. The medical team determines that the patient shows symptoms of no rejection to the transplanted organ.

Example 15

Use of the Composition of DHA Free from PhA in Autoimmune Diseases, Inflammatory Chronic Diseases and Skeletal Bone Diseases The role of DHA in chronic inflammations is widely known and has been briefly described throughout the different sections of the applications. But the most outstanding paper in these problems is the regulation of the dendritic cells. In this sense, the product of this invention is a coadjuvant that reduces the dose and time of use of immunesuppressors on a significant manner, particularly studied in this invention for LES, rheumatoid arthritis, juvenile arthritis, psoriasic and gout arthritis; and muscular dystrophy. It is also quite well-known the role of the product of this invention in the prevention and treatment of arthrosis and osteoporosis.

In a 26 year old female diagnosed from SLE and with a history of SLE and systemic sclerodermia with 8 years of follow up and treatment with 4 g/day of DHA from this invention, the clinical signs disappeared including the presence of antinuclear antibodies (ANA).

Example 16

Use of the DHA Composition Free from PhA in Dermatology: Androgenic Alopecia, Acne Rosacea and Acne Vulgaris, Atopic Dermatitis, Ichthyosis, Erythrodermia, Esclerodema, Discoid Lupus, Dermatomyositis, Psoriasis In the androgenic alopecia (masculine and femenine) the activity of the enzyme 5-alpha reductase, responsible for the production of Dihydrotestosterone (DHT) from testosterone, is increased. An increase in DHT result in hair fall out. DHA is an inhibitor of the enzyme "5-alpha Reductase" type 1 and 2, preserving the androgenic activity (testosterone). In order to inhibit this enzyme, a minimum dose of 2 g/day of DHA without PhA is needed, with the optimum dose being 4 g/day; changes in the hair loss and inflammation of the scalp can be seen within 4 weeks of the treatment. In order to avoid the alopecia, the suppression of the expression should be continuous, being possible to use lower maintenance doses (1-4 g/day). This treatment has the advantage against other inhibitors (ie. finasteride), that it does not reduce the levels of testosterone needed for general health and the function of the eye surface, prostate, muscular and neural tissue; being also useful for the treatment of the benign prostate hypertrophy.

36 males between 18 and 44 years and 4 females with androgenic alopecia took a treatment of 4 g/day of DHA without PhA during 5 years. The hair fall was stabilised within 4 weeks by 92.4% and by 95% at 6 weeks. In males, the capillary density increased by 52.8% and by 75% in females. A follow up was carried out for 2 years, during which there were no signs of alopecia.

In cases of atopic dermatitis, psoriasis and alopecia areata, the important anti-inflammatory effect of DHA, due to its control of the cellular cycle and over the immune system (cytokines, dendritic cells etc.) is behind its preventive effect and use as coadjuvant in these conditions.

One of the elements that contributes to the acne problems is an increased production of DHT from testosterone via the enzyme 5-alpha Reductase. Therefore, the uptake of DHA, based on the same mechanism previously explained for alopecia, contributes to improve acne. Treatment with DHA free from PhA, both in its oral and topical use over the skin, is very efficient treating acne due to its antibacterial and antiinflammatory properties as well as to its capacity to normalise the fluid secretion of the skin sebaceous glands which is controlled by androgens, the main agents involved in acne. Therefore, the topical use over the skin 200 mg/cm$^2$ during 20 minutes 2-5 times a week is particularly efficient against cystic acne.

A case of a 23 year old female with a history of a complicated and permanent cystic acne for 7 years, resistant to antibiotic and cis-retinoic acid treatments. She was treated with 4 g/day of DHA free from PhA and 2 weekly sessions where the same oil, deodorised and with lemon flavour, was applied directly over the skin for 20 minutes after which it was removed. Signs of remission were detected within the first week and after 8 weeks, there was only a residual acne. The oral treatment was maintained for 9 months until the total remission of the acne and no new activity of the acne could be detected during at least one year of follow up.

Knowledge on the role of DHA as a treatment for immune system alterations is growing with time. Particularly, in atopic dermatitis clinical trials have been performed where fatty acids such as DHA, reduce the immunological response through cytokines (IL-5, IL-13, IL-10, and IFN-gamma) in response to all allergens, reducing the activity of the atopic dermatitis. Particularly, atopic dermatitis and air allergies are associated to IL-10, where DHA is particularly efficient in reducing IL-10 and the allergic reaction (Dunstan et al. 2003 and 2005).

DHA from the present invention exhibits a lower allergic activity since it is possible to obtain a DHA free from PhA, from sources different to fish (cases of allergy) and of high purity, deodorised and highly reduced in peptides and derivates.

Particularly, the composition of the invention is indicated for Icthyosis (ie. harlequin icthyosis, vulgaris, congenital eritrodermia icthyosiform), since the product is free from PhA, an inductor of Icthyosis, and DNA's antiinfectious, immunomodulating and antiapoptosis effect, where some types of icthyosis also exhibit ocular manifestations in the eye surface and cornea.

Example 17

Use of the DHA Composition Free in PhA in Neumology and Asthma

In target tissues where DHA is specially concentrated or in tissues where there is a high mitochondrial activity, DHA increases the functional activity of such tissues. (ie. photoreceptors, neurones, lung alveoli, Purkinje cells, nephrones, dendritic cells, smoth and estriated myocites, hepatocytes, spermatozoids, ovules). Whilst DHA improves the function of such cellular types, PhA reduces their activity and normal function through the reduction of their mitochondrial activity.

In this sense, DHA is known to reduce the hypersensibility immunological response to aero-allergens which are responsible, not only for the atopic dermatitis but for lower respiratory tract diseases and asthma. Besides, DHA has a particular effect in the prevention of infectious diseases through the activity on dendritic cells, reducing infections and bronchial asthma. As well as improving the function of dendritic cells (antiviral activity, bactericidal, preventing rejections, antitumoral), DHA also improves the respiratory function, being particularly efficient in asthma and chronic respiratory diseases (EPOC). Treatment with DHA improves the ventilatory capacity in chronic respiratory diseases and asthma (Kompauer et al., 2008).

Therefore, the use of the composition of the invention for the treatment of cystic fibrosis is highly recommended, since this pathology has a defficiency in DHA as well as frequent chronic infections. Since the composition of the invention is free of PhA, this results in a stronger antiinfectious effect. DHA has specific functions in the different cellular types described in this invention. However, modulation of the dendritic cells by DHA is the most relevant common mechanism of action for treatments with DHA as a coadjuvant and preventive measure in human pathologies, particularly when free of PhA, since the latter alters the function of dendritic cells and increases the sensibility to infections.

Example 18

Use of the Composition of DHA Free from PhA in the Digestive System and Inflammatory Bowel Disease (IBD)

The therapeutic effects of DHA in the regulation of prostaglandins, cytokines and homeostasis as fibrinolytic and platelet antiaggregant in inflammatory bowel diseases (IBD), have probably been the first known applications in the medical literature. DHA offers the advantage, over other PUFA, that it increases the activity of prostaglandins from the 3 series from the EPA synthesis, particularly at high doses of DHA (>4 g/day); it also inhibits prostaglandins from the 2 series and has its own activity from its own derivates, the docosanoids. DHA also controls the secretory activity of the intestinal Globet cells and enterocytes. In these diseases, a preventive treatment is needed during long periods of time. In this sense, treatment with DHA is very adequate, since it does not reduce the synthesis of other essential fatty acids such as gamma-linolenic acid (omega 6) necessary for the synthesis of the most anti-immflamatory prostaglandins of series 1, where its synthesis is inhibited by other omega 3 fatty acids such as EPA.

DHA without PhA exhibits an increased antiinfectious activity: against bacteria, virus, fungus and parasites, which can be appreciated particularly at doses beyond 4 g/day. Many intestinal immflamatory diseases are associated to chronic infections (ej: *H. pylori, Clostrodium* sp., etc.). In this invention, studies have been carried out with ulcerative colitis in adults and children, pseudomembranous colitis, Crohn's disease, collagenous colitis, irritable bowel syndrome, gastritis and esofagitis.

In order to carry on this study, oral doses of DHA where used viz. 4 g/day DHA free from PhA and higher doses up to 8 g/day for the treatment of acute cases. Its rectal use (particularly in Proctitis) combined with low doses of corticoids (ie. 5-10 mg/day) results in an efficient treatment against IBD.

32 year old female with ulcerative colitis, with a history of 6 years of disease without remission, who was treated for 6 years with systemic corticotherapy and proposed for surgery. She was treated with 12 g/day of DHA free from PhA during 8 weeks together with corticoids, starting with 10 mg of Dacortin and a reduction to 2.5 mg/15 days. Within the first 48 hours of the treatment, there was a significant reduction of the bleeding and of the abdominal pain and at 20 days there was a complete remission of the bleeding. After 8 weeks, a biopsy was carried out where a significant reduction of the immflamatory activity was observed. Already without a corticotherapy treatment, the initial dose of 12 g/day, was reduced by 1 g of DHA a week during the 8 subsequent weeks, until reaching a maintenance dose of 4 g/day which was maintained for 2 years during which the ulcerative colitis remained inactive.

The use of DHA as a coadjuvant in the treatment of IBD with corticoids and statins enables reducing the dose of the latter and its secondary effects such as lipodystrophy. DHA free from PhA does not interact with statins, moreover, it particularly reduces the risk of rhabdomyolisis and the hepatopathy associated to simvastatins, therefore reducing the need to use statins, which are contraindicated in lipodystrophy associated to retroviral treatments. DHA reduces the hypertriglyceridemia and improves the lipoproteic profile without reducing the LDL cholesterol fraction, except at very high doses (>8 g/day) or when combined with sport (Yates-A et al., 2009). An alternative to the use of high doses of DHA (beyond 8 g/day) could be the use of 1-4 g/day or more together with a low dose of statins (ie. 5 mg of simvastatine), being an efficient dose for the treatment of lipodystrophy (ie. treatments with anti-retrovirals and corticoids).

Treatment of 7 patients with a dose of 4 g/day of DHA free from PhA and corticoids during more than 3 months, reduced the formation of the usual lipodystrophy.

Example 19

Use of the DHA Composition Free from PhA in Sports Medicine

There is an increasing interest on the role of DHA in sports medicine, since it improves the lipoproteic profile, reduces cholesterol, plays its role in controlling the Purkinje cells when controlling the cardiac frequency and improves the ventilatory function and the aerobic metabolism in myocites. Studies carried out with DHA on professional sports people, show that it is the fatty acid with more hypolipemiant activity and that it improves the aerobic capacity, in accordance with the research on the role of DHA on physiology and physiopathology. The DHA taken chronically in low dosages (0.5 g/day) and in the form of a structured lipid can be an important complement in replacing homeostatis during moderate and even intensive physical effort (Lopez-Roman et al., 2008).

The base of these studies is connected with mechanisms of action where PhA is a particular antagonist described in this invention. So, from a theoretical viewpoint, it is expected for the DHA from this invention to have a higher activity in sports physiology. As described in the invention, PhA has a powerful toxicity and causes irreversible damages in the mitochondrial electron transport chain, producing a severe reduction of the oxidative phosphorylation, being a critical point in sports performance and the aerobic, muscular and cardiovascular metabolism in sports medicine. PhA is associated with conduction delay and sudden cardiac death (Mönning et al., 2004).

Example 20

Use of the Composition of DHA Free from PhA in Thyroid Pathologies

Currently, there is a significant increase of cases with thyroiditis, which induce hyperthyroidism and hypothyroidism with presence of anti-thyroid antibodies in an euthyroid population with and without symptoms. In this invention, a relationship has been described in RP patients between the presence of antibodies anti-TPO (antithyroid peroxidase antibodies) and a DHA deficit. This relationship was also determined in RP patients with thyroid pathology and abnormal levels of anti-thyroid antibodies. DHA improves obesity problems in cases of hypothyroidism, it is cardioprotective and improves the lipoproteic profile in patients with thyroid disease.

Treatment with 4 g/day of DHA without PhA was established in 11 asymptomatic patients under a hyperthyroid and hypothyroid treatment (depending on the case ie. Tyrodril and Tyroxine) between 17 and 49 years, with and without defficiency of DHA and abnormal levels of antithyroid antibodies. After 6 months of treatment, all patients showed a significant reduction on the antithyroid antibodies and a significant reduction on the cardiac rhythm symptoms, both in hyperthyroid as well as hypothyroid patients (induced by radioactive iodine) due to treatment with thyroxine.

Example 21

Use of the DHA Composition Free from PhA in Cardiovascular Diseases

Whilst DHA has an effect as cofactor in the prevention of cardiovascular risk factors, diabetes etc. it has not proved to have a significant clinical effect in the treatment of these signs. However, it has reduced the mortality and morbidity in patients with cardiovascular diseases. DHA reduces the atherosclerotic effect associated to such risk factors. Particularly in diabetes, due to its antiangiogenic effect and neurotrophic factor in retina (diabetic retinopathy) and neuroprotector (diabetic neuropathy).

The composition of the present invention has a powerful antiarrhythmic effect, particularly because is PhA free, since PhA induces conduction delay and sudden cardiac death, being more efficient than commercial DHA in several types of arrhythmia. The compound of the invention, DHA free from PhA is useful in the prevention of arrhythmias and thrombosis, as well as on the treatment of some vascular pathologies such as Raynaud syndrome and for the treatment of hypertriglyceremia. In addition, DHA reduces the number of deaths due to cardiac failure associated to atherosclerotic pathologies, hyperglycemia, artherosclerosis associated to hypertension, diabetes and other metabolic and infectious factors related with arteriosclerosis such as high homocysteine levels and apopprotein (a). It particularly reduced apo (a) levels in 2 patients with high levels (>30 mg/dl) who had cerebrovascular arteriosclerosis and neurological alterations of ischaemic origin. Treatment with 4 g/day reduced by 50% the apo (a) levels and normalised the cognitive function associated to the recurrent cerebral infarcts that they suffered.

Example 22

Use of the DHA Composition Free of PhA in Parasitic and Infectious Diseases

The main mechanism of action of DHA as antiparasitic and antiinfectious agent (parasites, bacteria, virus and fungus) is related to its powerful antiiflammatory effect (Tiesset et al., 2009) mediated by cytokines, leukocyte fagocytosis, as previously described in this innovation. PhA reduces the activity of GTPases from subfamily Rho in epitelial cells and mucose membranes, favouring bacterial, fungus and parasites infections, a mechanism which is used by numerous bacterial toxins as their main infectious mechanism (*Pseudomonas, Clostridium*, etc,) (Engel & Balachandran, 2009; Genth—et al., 2006). PhA also interacts with antimitotics. Therefore, PhA activity is antagonic to that of DHA, very specific in infections, and thus, DHA free from PhA in more efficient to fight infections.

On an opposite way to PhA, DHA reduces bacterial infections such as that by *Pseudomonas aeruginosa* in lung infections mediated by the inflammatory response (Tiesset et al., 2009) and fungus infections (Bajpai et al., 2009) mediated by DHA specific docosanoids (Haas-Stapleton, et al. 2007). In bacterious infections by *Helicobacter pylori*, DHA has proved to be, through in vitro studies using the Kirby Bauer method, an active bactericidal substance (Drago et al., 1999). Studies in vitro and in vivo determine the antiinfectious (virus, fungus and bacteria) and antiparasitary capacity of DHA. DHA is severely reduced in infections by *Plasmodium falciparum* (Hsiao et al., 1991), and it is known that further reductions (25%) are associated to retinal degeneration, dementia and an increase in atherosclerosis associated to other risk factors. Viral infections (Rubeola) have also been associated to high levels of phytanic acid (Pike et al., 1990).

DHA free from PhA can be used as a preventive compound and potenciator of the effects of antibiotics, reducing the cases of infections and reinfections particularity in viral and fungal infections. In this way, the use of antibiotics is reduced, improving its epidemiologic activity and avoiding viral and fungal infections secondary to the use of antibiotics. The antinfectious effect of the product of this invention, reduces the complications and evolution of infections of great extra-infectious and epidemiological relevance, such as the digestive pathology associated to *H. pylori* and decay.

BIBLIOGRAPHY

Adamich-M, Towle-A, Lunan-K D. Ficoll density gradient separation of extracellular DDT from *Chlorella*. Bulletin of Environmental Contamination and Toxicology. 1974; 12(5):562-6.

Adler-R. Regulation of neurite growth in purified retina cultures: effects of PNPF, a substratum-bound neurite-promoting factor. J Neurosci Res. 1982; 8:165-177.

Allen-N E, Grace-P B, Ginn-A, Travis-R C, Roaddam-A W, Appleby-P N, Key-T. Phytanic acid: measurement of plasma concentrations by gas-liquid chromatography-mass spectrometry analysis and associations with diet and other plasma fatty acids. Br J Nutr. 2008 March; 99(3):653-9.

Anderson-R E, Maude-M B, McClellan-M, Matthes-M T, Yasumura-D, LaVail-M M. Low docosahexaenoic acid levels in rod outer segments of rats with P23H and S334ter rhodopsin mutations. Mol Vis. 2002 September; 8:351-8.

Andreola-F, Giandomenico-V, Spero-R, De Luca-L M Expression of a smaller lecithin:retinol acyl transferase transcript and reduced retinol esterification in MCF-7 cells. Biochem Biophys Res Commun. 2000 December; 279(3):920-4.

Arnhold-T, Elmazar-M, Nau-H. Prevention of Vitamin A Teratogenesis by Phytol or Phytanic Acid Results from Reduced Metabolism of Retinol to the Teratogenic Metabolite, All-trans-retinoic Acid. Toxicol Sciences. 2002; 66: 274-282.

Ayranci-E, Akgul-G. Apparent molar volumes and viscosities of lauric, palmitic, and stearic acids in 2-butanol at (20, 30, 40, and 60)° C. Journal of chemical and engineering data. 2003; 48(1): 56-60.

Bajpai-V K, Kim-H R, Hou-C T, Kang-S C. Microbial conversion and in vitro and in vivo antifungal assessment of bioconverted docosahexaenoic acid (bDHA) used against agricultural plant pathogenic fungi. J Ind Microbiol Biotechnol. 2009 March Barragan-I, Marcos-I, Borrego-S, Antinolo-G. Molecular analysis of RIM1 in autosomal recessive Retinitis pigmentosa. Ophthalmic Res. 2005 March-April; 37(2):89-93.

Bazan-N G; Scott-B L; Reddy-T S; Pelias-M Z. Decreased Content of Docosahexaenoate and Arachidonate in Plasma Phospholipids in Usher's Syndrome. Biochem-Biophys-Res-Commun. 1986; 141(2): 600-4.

Bellet-R, Carducci-M, Petrylak-D, Kasimis-B, Irwin-D, Modiano-M, Mansour-R, Axelrod-R, Doukas-M. Phase II study of DHA-paclitaxel (TXP) as first line chemotherapy in patients with hormone refractory prostate cancer (HRPC). Journal of Clinical Oncology, 2004 ASCO Annual Meeting Proceedings (Post-Meeting Edition). Vol 22, No 14S (July 15 Supplement), 4657

Boorjian-S, Tickoo-S K, Mongan-N P, Yu-H, Bok-D, Rando-R R, Nanus-D M, Scherr-D S, Gudas-L J Reduced lecithin: retinol acyltransferase expression correlates with increased pathologic tumor stage in bladder cancer. Clin Cancer Res. 2004 May; 15(10):3429-37.

Bottino-N R, Vanderburg-G A, Reiser-R. Resistance of certain long-chain polyunsaturated fatty acids of marine oils to pancreatic lipase hydrolysis, Lipids. 1967; 2(6): 489-93.

Britton-T C; Gibberd-F B; Clemens-M E; Billimoria-J D; Sidey-M C. The Significance of Plasma Phytanic Acid Levels in Adults. J-Neurol-Neurosurg-Psychiatry. 1989; 52(7): 891-4.

Brown-P J, Mei-G, Gibberd-F B, Burston-D, Mayne-P D, McClinchy-J E, Margaret-S. Diet and Refsum's disease. The determination of phytanic acid and phytol in certain foods and the application of this knowledge to the choice of suitable convenience foods for patients with Refsum's disease. Journal of Human Nutrition and Diabetics. 1993; 6 (4): 295-305.

Canas-B J, Yurawecz-M P. Ethyl carbamate formation during urea complexation for fractionation of fatty acids. Journal of the American Oil Chemists' Society. 1999; 76(4): 537.

Carr-S A; Biemann-K; Shoji-S; Parmelee-D C; Titani-K. N-Tetradecanoyl is the NH2-Terminal Blocking Group of the Catalytic Subunit of Cyclic AMP-Dependent Protein Kinase from Bovine Cardiac Muscle. Proc-Natl-Acad-Sci-USA. 1982; 79(20): 6128-31.

Chau-K Y, Sivaprasad-S, Patel-N, Donaldson-T A, Luthert-P J, Chong-N V. Plasma levels of matrix metalloproteinase-2 and -9 (MMP-2 and MMP-9) in age-related macular degeneration. Eye. 2008 June; 22(6):855-9.

Chucair-A J, Rotstein-N P, Sangiovanni-J P, During-A, Chew-E Y, Politi-L E. Lutein and zeaxanthin protect photoreceptors from apoptosis induced by oxidative stress: relation with docosahexaenoic acid. Invest Ophthalmol V is Sci. 2007 November; 48(11):5168-77.

Connor-W E; Weleber-R G; DeFrancesco-C; Lin-D S; Wolf-D P. Sperm Abnormalities in Retinitis Pigmentosa. Invest-Ophthalmol-Vis-Sci. 1997; 38(12): 2619-28.

Dizhoor-A M; Chen-C K; Olshevskaya-E; Sinelnikova-V V; Phillipov-P; Hurley-J B. Role of the Acylated Amino Terminus of Recoverin in Ca(2+)-Dependent Membrane Interaction. Science. 1993; 259(5096): 829-32.

Dizhoor-A M; Ericsson-L H; Johnson-R S; Kumar-S; Olshevskaya-E; Zozulya-S; Neubert-T A; Stryer-L; Hurley-J B; Walsh-K A. The NH2 Terminus of Retinal Recoverin is Acylated by a Small Family of Fatty Acids. J-Biol-Chem. 1992; 267(23): 16033-6.

DOCE. Decisión de la Comisión, de 26 de septiembre de 1990, por la que se establecen los métodos de referencia para la investigación de residuos de metales pesados y de arsénico (DOUE de 18 Oct. 1990).

Dorsey-N E. Viscosity of water taken from "Properties of Ordinary Water-Substance. Hafner Publishing Co. New York. 1940. p 184.

Drago-L, Mombelli-B, Clardo-G, De-Vecchi-E, Gismondo-M R. Effects of three different fish oil formulations on *Helicobacter pylori* growth and viability: in vitro study. J Chemother. 1999 June; 11(3):207-10.

Dunstan-J A, Hale-J, Breckler-L, Lehmann-H, Weston-S, Richmond-P, Prescott-S L. Atopic dermatitis in young children is associated with impaired interleukin-10 and interferon-gamma responses to allergens, vaccines and colonizing skin and gut bacteria. Clin Exp Allergy. 2005 October; 35(10):1309-17.

Dunstan J A, Mori T A, Barden A, Beilin L J, Taylor A L, Holt P G, Prescott S L. Fish oil supplementation in pregnancy modifies neonatal allergen-specific immune responses and clinical outcomes in infants at high risk of atopy: a randomized, controlled trial. J Allergy Clin Immunol. 2003 December; 112(6):1178-84.

Elmazar-M M, Nau-H. Potentiation of the teratogenic effects induced by coadministration of retinoic acid or phytanic acid/phytol with synthetic retinoid receptor ligands. Arch Toxicol. 2004 November; 78(11): 660-8.

Elmazar-M M, Nau-H. Synergistic teratogenic effects induced by retinoids in mice by coadministration of a RARalpha- or RARgamma-selective agonist with a RXR-selective agonist. Toxicol Appl Pharmacol. 2001 January; 170(1): 2-9.

Engel-J, Balachandran-P. Role of *Pseudomonas aeruginosa* type III effectors in disease. Curr Opin Microbiol. 2009 February; 12(1):61-6.

Eter-N, Alex-A F, Spitznas-M, Tittel-A P, Holz-F G, Kurts-C. Inhibitory effect of epigallocatechin gallate (EGCG), resveratrol and curcumin on the proliferation of human retinal pigment epithelial cells in vitro. Symposium der International Society of Ocular Trauma. Würzburg, Düsseldorf 2008. German Medical Science GMS Publishing House.

Faber-K. Biotransformations in Organic Chemistry, Springer, Berlin (2004).

Feng-S, Lock-A L, Garnsworthy-P C. Technical Note: A Rapid Lipid Separation Method for Determining Fatty Acid Composition of Milk. J Dairy Sci. 2004; 87:3785-8.

Ferdinandusse-S, Denis-S, Clayton-P T, Graham-A, Rees-J E, Allen-J T, McLean-B N, Brown-A Y, Vreken-P, Waterham-H R, Wanders-R J. Mutations in the gene encoding peroxisomal alpha-methylacyl-CoA racemase cause adult-onset sensory motor neuropathy. Nat Genet 2000; 24:188-91

Ferdinandusse-S, Zomer-A W, Komen-J C, van-der-Brink-C E, Thanos-M, Hamers-F P, Wanders-R J, van der Saag-P T, Poll-The-BT, Brites-P. Ataxia with loss of Purkinje cells in a mouse model for Refsum disease. Proc Natl Acad Sci USA. 2008 Nov. 18; 105(46):17712-7

Finderhut-R, Schmitz-W, Garavaglia-B, Reichmann-H, Conzelmann-E. Impaired degradation of phytanic acid in cells from patients with mitochondriopathies: evidence for the involvement of ETF and the respiratory chain in phytanic acid alpha-oxidation. J Inherit Metab Dis. 1994; 17(5): 527-32.

Fleury-C, Mignotte-B, Vayssière-J L. Mitochondrial reactive oxygen species in cell death signaling. Biochimie. 2002 February-March; 84(2-3):131-41

Fuentes-Arderiu-X, Castiñeiras-Lacambra-M J, Queraltó Compañó-J M. Bioquímica Clínica y Patología Molecular. 1998 (ed. II); Reverté. 148-9.

Genth-H, Johannes-H, Hartmanna-B, Hofmanna-F, Justa-I, Gerharda-R. Cellular stability of Rho-GTPases glucosylated by *Clostridium difficile* toxin B. FEBS letters. 2006 June; 580 (14): 3565-9.

Guenzi-E, Töpolt-K, Lubeseder-Martellato-C, Jörg-A, Naschberger-E, Benelli-R, Albini-A, Stürzl-M. The guanylate binding protein-1 GTPase controls the invasive and angiogenic capability of endothelial cells through inhibition of MMP-1 expression. EMBO J. 2003 August; 22(15): 3772-82

Guo-X, Knudsen-B S, Peehl-D M, Ruiz-A, Bok-D, Rando-D, Rando-R R, Rhim-J S, Nanus-D M, Gudas-L J. Retinol metabolism and lecithin:retinol acyltransferase levels are reduced in cultured human prostate cancer cells and tissue specimens. Cancer Res. 2002 March; 62(6):1654-61.

Guo-X, Nanus-D M, Ruiz-A, Rando-R R, Bok-D, Gudas-L J. Reduced levels of retinyl esters and vitamin A in human renal cancers. Cancer Res. 2001 March; 61(6): 2774-81.

Guo-X, Ruiz-A, Rando-R R, Bok-D, Gudas-L J. Esterification of all-trans-retinol in normal human epithelial cell strains and carcinoma lines from oral cavity, skin and breast: reduced expression of lecithin:retinol acyltransferase in carcinoma lines. Carcinogenesis. 2000 November; 21(11):1925-33.

Gutierrez-Torre-S M. Retinosis Pigmentaria; Estudio Comparativo de la Metódica y Resultados del Tratamiento en España y la Unión Soviética. "Tesis Doctoral". Universidad-Oviedo. 1994.

Gutknecht-J. Proton/hydroxide conductance through phospholipid bilayer membranes: effects of phytanic acid. Biochim Biophys Acta. 1987 April; 898(2): 97-108.

Haas-Stapleton-E J, Lu-Y, Hong-S, Arita-M, Favoreto-S, Nigam-S, Serhan-C N, Agabian-N. *Candida albicans* modulates host defense by biosynthesizing the pro-resolving mediator resolvin E1. PLoS ONE. 2007 December; 2(12):13-16.

Haim-M. Prevalence of Retinitis Pigmentosa and Allied Disorders in Denmark. II. Systemic Involvement and Age at Onset. Acta-Ophthalmol-Copenh. 1992; 70(4): 417-26.

Hansen-R P. 3,7,11,15-tetramethylhexadecanoic acid: its occurrence in the tissues of humans afflicted with Refsum's syndrome. Biochim Biophys Acta. 1965 October; 106(2):304-10.

Harrison-R O, Carlson-R E. Simplified sample preparation methods for rapid immunoassay analysis of pcdd/fs in foods. 2000; 20th International Symposium on Halogenated Environmental Organic Pollutants and POPs. Aug. 13-17, 2000 Monterey, Calif.

Hashimoto-T, Shimizu-N, Kimura-T, Takahashi-Y, Ide-T. Polyunsaturated Fats Attenuate the Dietary Phytol-Induced Increase in Hepatic Fatty Acid Oxidation in Mice. J. Nutr. 2006 April; 136:882-6.

Hoffman-D R; Birch-D G. Docosahexaenoic Acid in Red Blood Cells of Patients with X-Linked Retinitis Pigmentosa. Invest-Ophthalmol-Vis-Sci. 1995; 36(6): 1009-18.

Horii-N, Arato-S, Narayan-B, Hosokawa-M, Sashima-T, Miyashita-K. Occurrence of conjugated cyclopropanoid acid in purified fish oil. J Am Oil Chem Soc. 2007; 84 (8): 749-54.

Hsiao-L L, Howard-R J, Aikawa-M, Taraschi-T F. Modification of host cell membrane lipid composition by the intraerythrocytic human malaria parasite *Plasmodium falciparum*. Biochem J. 1991 Feb. 15; 274 (Pt 1):121-32.

Hsing-A W, Comstock-G W, Abbey-H, Polk-B F. Serologic Precursors of Cancer. Retinol, Carotenoids, and Tocopherol and Risk of Prostate Cancer. J Natl Cancer Inst. 1990; 82:941-6.

Idel-S, Ellinghaus-P, Wolfrum-C, Nofer-J R, Gloerich-J, Assmann-G, Spener-F, Seedorf-U. Branch Chain Fatty Acids Induce Nitric Oxide-dependent Apoptosis in Vascular Smooth Muscle Cells. J Biol Chem. 2002 December; 277 (51): 49319-25.

Jones-R J, Hawkins-R E, Eatock-M M, Ferry-D R, Eskens-F A, Wilke-H, Evans-T R. A phase II open-label study of DHA-paclitaxel (Taxoprexin) by 2-h intravenous infusion in previously untreated patients with locally advanced or metastatic gastric or oesophageal adenocarcinoma. Cancer Chemother Pharmacol. 2008 March; 61(3):435-41.

Jurukovski-V, Simon-M. Reduced lecithin:retinol acyl transferase activity in cultured squamous cell carcinoma lines results in increased substrate-driven retinoic acid synthesis. Biochim Biophys Acta. 1999 January; 1436(3):479-90.

Kahler-S, Schönfeld-P, Reiser-G. The Refsum disease marker phytanic acid, a branch chain fatty acid, affects Ca2+ homeostasis and mitochondria, and reduces cell viability in rat hippocampal astrocytes. Neurobiol Dis. 2005 February; 18(1):110-8.

Ko-C H, Shen-S C, Hsu-C S, Chen-Y C. Mitochondrial-dependent, reactive oxygen species-independent apoptosis by myricetin: roles of protein kinase C, cytochrome c, and caspase cascade. Biochem Pharmacol. 2005 March; 69(6): 913-27.

Ko-C H, Shen-S C, Lee-T J F, Chen-Y C. Myricetin inhibits matrix metalloproteinase 2 protein expression and enzyme activity in colorectal carcinoma cells. Mol Cancer Ther. 2005; 4:281-90

Kokame-K; Fukada-Y; Yoshizawa-T; Takao-T; Shimonishi-Y. Lipid Modification at the N Terminus of Photoreceptor G-protein α-Subunit [Comentarios]. Nature. 1992; 359(6397): 749-52.

Komen-J C, Distelmaier-F, Koopman-W J, Wanders-R J, Smeitink-J, Willems-P H. Phytanic acid impars mitochondrial respiration through protonphoric action. Cell Mol Life Sci. 2007 December; 64(24):3271-81.

Kompauer-I, Demmelmair-H, Koletzko-B, Bolte-G, Linseisen-J, Heinrich-J. Association of fatty acids in serum phospholipids with lung function and bronchial hyperresponsiveness in adults. Eur J Epidemiol. 2008; 23(3):175-90.

Kroemer-G, Galluzzi-L, Brenner C. Mitochondrial Membrane Permeablization in Cell Death. Physiol. 2007; 87: 99-163.

Laabich-A, Manmoto-C C, Kuksa-V, Leung-D W, Vissvesvaran-G P, Karliga-I, Kamat-M, Scott-I L, Fawzi-A, Kubota-R. Protective effects of myricetin and related flavonols against A2E and light mediated-cell death in bovine retinal primary cell culture. Exp Eye Res. 2007 July; 85(1): 154-65.

Lide-D R, Milne-G W A. Handbook of Data on Organic Compounds. Edition: 3, illustrated, revised Published by CRC Press, 1994; 6560 pages. ISBN 0849304458.

Liu-L, Gudas-L J. Disruption of the lecithin:retinol acyltransferase gene makes mice more susceptible to vitamin A deficiency. J Biol Chem. 2005 December; 280(48): 40226-34.

Lloyd-M D, Darley-D J, Wierzbiki-A S, Threadgill-M D. Alpha-methylacyl-CoA racemase—an 'obscure' metabolic enzyme takes centre stage. FEBS J. 2008 March; 275(6):1089-102.

López-Román-J, Luque-A, Martínez-A, Villegas-J A. Modifications in oxidative damage in sportsmen after docosahexaenoic acid (DHA) ingestion. J Int Sports Nut. 2008 June Martínez-M. Severe Changes in Polyunsaturated Fatty Acids in the Brain, Liver, Kidney, and Retina in Patients with Peroxisomal Disorders. Adv-Exp-Med-Biol. 1992; 318: 347-59.

Matsuura-T, Hasumura-S, Nagamori-S, Murakami-K. Retinol esterification activity contributes to retinol transport in stellate cells. Cell Struct Funct. 1999 June; 24(3):111-6.

McColl-A J; Converse-C A. Lipid Studies in Retinitis Pigmentosa. Prog-Lipid-Res. 1995; 34(1): 1-16.

Mobley-J A, Leav-I, Zielie-P, Wotkowitz-C, Evans-J, Lam-Y W, L'Esperance-B S, Jiang-Z, Ho-S M. Branch Fatty Acids in Dairy and Beef Products Markedly Enhance α-Methylacyl-CoA Racemase Expression in Prostate Cancer Cells in Vitro. Cancer Epidemiology Biomarkers & Prevention. 2004 August; 12: 775-83.

Mönning-G, Wiekowski-J, Kirchhof-P, Stypmann-J, Plenz-G, Fabritz-L, Bruns-H J, Eckardt-L, Assmann-G, Haverkamp-W, Breithard-G, Seedorf-U. Phytanic acid accumulation is associated with conduction delay and sudden cardiac death in sterol carrier protein-2/sterol carrier protein-x deficient mice. J Cardiovasc Electrophysiol. 2004 November; 15(11):1310-6.

Moriguchi-K; Yoshizawa-K; Shikata-N; Yuri-T; Takada-H; Hada-T; Tsubura-A. Suppression of N-methyl-N-nitrosourea-induced photoreceptor apoptosis in rats by docosahexaenoic acid. Ophthalmic Res. 2004 March-April; 36(2):98-105.

Moriguchi-K; Yuri-T; Yoshizawa-K; Kiuchi-K; Takada-H; Inoue-Y; Hada-T; Matsumura-M; Tsubura-A. Dietary docosahexaenoic acid protects against N-methyl-N-nitrosourea-induced retinal degeneration in rats. Exp Eye Res. 2003 August; 77(2):167-73.

Neubert-T A; Johnson-R S; Hurley-J B; Walsh-K A. The Rod Transducin Alfa Subunit Amino Terminus is Heterogeneously Fatty Acylated. J-Biol-Chem. 1992 September; 267(26): 18274-7.

Nourooz-Zadeh-J, Pereira-P. Age-related accumulation of free polyunsaturated fatty acids in human retina. Ophthalmic Res. 1999; 31(4):273-9.

Nus-M, Sánchez-Muniz-F J, Sánchez-Montero-J M. Methodological Aspects and Relevance of the Study of Vegetable Oil, Fat and Lipoprotein Oxidation Using Pancreatic Lipase and Arylesterase Food Technol. Biotechnol. 2006; 44 (1): 1-15.

O'Brien-P J; St Jules-R S; Reedy-T S; Bazan-N G; Zatz-M. Acylation of Disc Membrane Rhodopsin may be Normzymatic. J-Biol-Chem. 1987; 262: 5210-5.

O'Brien-P J; Zatz-M; Acylation of Bovine Rhodopsin by [H3] Palmitic Acid. J-Biol-Chem. 1984; 259: 5054-7.

Pahan-K, Khan-M, Smith-B T, Singh-I. Ketoconazole and other imidazole derivatives are potent inhibitors of peroxisomal phytanic acid alpha-oxidation. FEBS Lett. 1995 December; 377(2):213-6.

Pasquali-D, C Thaller-C, Eichele-G. Abnormal level of retinoic acid in prostate cancer tissues. J Clin Endocrinology & Metabolism. 1996; 81: 2186-91.

Pike-M G, Applegarth-D A, Dunn-H G, Bamforth-S J, Tingle-A J, Wood-B J, Dimmick-J E, Harris-H, Chantler-J K, Hall-J G. Congenital rubella syndrome associated with calcific epiphyseal stippling and peroxisomal dysfunction. J Pediatr. 1990 January; 116(1):88-94. Erratum in: J Pediatr 1990 February; 116(2):320.

Politi-L E, Bouzat-C, De los Santos-E B, Barrantes-F J. Heterologous retinal cultured neurons and cell adhesion molecules induce clustering of acetylcholine receptors and polynucleation in mouse muscle BC3H-1 clonal cell line. J Neurosci Res. 1996; 43:639-651.

Powers-J M et al. Cerebellar atrophy in chronic rhizomelic chondrodysplasia punctata: a potential role for phytanic acid and calcium in the death of its Purkinje cells. Acta Neuropathol (Berl). 1999 August; 98(2):129-34.

Pullarkat-R K; Reha-H; Patel-V K; Goedel-H H. "Ceroid-Lipofuscinosis: Batten's Disease". (Armstrong-D, Koppang-N; Rider-J A. Eds.). Amsterdam. Elsevier-Biomedical-Press. 1982; 335-43.

Ratnayake-W M N, Olsson-B, Ackman-R G. Novel branched-chain fatty acids in certain fish oils. Lipids. 1989; 24(7): 630-7.

Reiser-G, Schönfeld-P, Kahlert-S. Mechanism of toxicity of the branch-chain fatty acid phytanic acid, a marker of Refsum disease, in astrocytes involves mitochondrial impairment. Int J Dev Neurosci. 2006 April-May; 24(2-3):113-22.

Rotstein-N P, Politi-L E, German-O L, Girotti-R. Protective effect of docosahexaenoic acid on oxidative stress-induced apoptosis of retina photoreceptors. Invest Ophthalmol V is Sci. 2003 May; 44(5):2252-9.

Rotstein-N P; Aveldaño-M I; Barrantes-F J; Roccamo-A M; Politi-L E. Apoptosis to Retinal Photoreceptors During Development In Vitro: Protective Effect of Docosahexaenoic Acid. J Neurochem. 1997; 69(2): 504-13.

Schaefer-E J; Robins-S J; Patton-G M; Sandberg-M A; Weigel-DiFranco-C A; Rosner-B; Berson-E L. Red Blood Cell Membrane Phosphatidylethanolamine Fatty Acid Content in Various Forms of Retinitis Pigmentosa. J-Lipid-Res. 1995; 36(7): 1427-33.

Schönfeld P, Kahlert S, Reiser G. A study of the cytotoxicity of branched-chain phytanic acid with mitochondria and rat brain astrocytes. Exp Gerontol. 2006 July; 41(7):688-96.

Schönfeld P, Reiser G. Rotenon-like action of the branched-chain phytanic acid induces oxidative stress in mitochondria. J Biol Chem. 2006 Mar. 17; 281(11):7136-42.

Schönfeld-P, Kahlert-S, Reiser-G. In brain mitochondria the branch-chain fatty acid phytanic acid impairs energy transduction and sensitizes for permeability transition. Biochem J. 2004; 383(Pt 1):121-8.

Schönfeld-P, Woitczak-L. Fatty acids decrease mitochondrial generation of reactive oxygen species at the reverse. Biochim Biophys Acta. 2007 August; 1767(8):1032-40.

Serini S, Trombino S, Oliva F, Piccioni E, Monego G, Resci F, Boninsegna A, Picci N, Ranelletti F O, Calviello G. Docosahexaenoic acid induces apoptosis in lung cancer cells by increasing MKP-1 and down-regulating p-ERK1/2 and p-p38 expression. Apoptosis. 2008 September; 13(9): 1172-83.

Serkov I V, Grigor'ev V V, Ivanova T A, Gretskaya N M, Bezuglov V V, Bachurin S O. Effect of derivatives of docosahexaenoic acid on AMPA receptors in Purkinje neurons. Dokl Biol Sci. 2006 November-December; 411:434-5.

Sheren-Manoff-M, Shin-S J, Su-D, Bok-D, Rando-R R, Gudas-L J. Reduced lecithin:retinol acyltransferase expression in human breast cancer. Int J Oncol. 2006 November; 29(5):1193-9.

Shucheng-L, Chaohua-Z, Pengzhi-H, Hongwu-J. Concentration of docosahexaenoic acid (DHA) and eicosapentaenoic acid (EPA) of tuna oil by urea complexation: optimization of process parameters. J Food Engineering. 2006; 73(3) 203-9.

Simmons-D P. Andreola-F, De Luca-L M. Human melanomas of fibroblast and epithelial morphology differ widely in their ability to synthesize retinyl esters. Carcinogenesis. 2002 November; 23(11):1821-30.

Steinberg-D. Refsum disease. The Metabolic and Molecular Bases of Inherited Disease. Vol. 2. (Scriver-C R, Beaudet-A L, Sly-W S, Valle-D. Eds.) New York. McGraw-Hill. 1995; 2351-69.

Thornburg-T, Turner-A R, Chen-Y Q, Vitolins-M, Chang-B, Xu-J. Phytanic acid, AMACR and prostate cancer risk. Future Oncol. 2006 April; 2(2):213-23.

Tucker-B, Klassen-H, Yang-L, Chen-D F, Young-M J. Elevated MMP Expression in the MRL Mouse Retina Creates a Permissive Environment for Retinal Regeneration. Invest Ophthalmol Vis Sci. 2008 April; 49(4):1686-95.

Voss-A; Reinhart-M; Sprecher-H. Differences in the Interconversion between 20- and 22-Carbon (n-3) and (n-6) Polyunsaturated Fatty Acids in Rat Liver. Biochim-Biophys-Acta, 1992; 1127(1): 33-40.

Wallström-P, Bjartell-A, Gullberg-B, Olsson-H, Wirfält-E. A prospective study on dietary fat and incidence of prostate cancer (Malmö, Sweden). Cancer Causes Control. 2007 December; 18(10):1107-21.

Walsh-P C. Serum levels of phytanic acid are associated with prostate cancer risk. J Urol. 2005 November; 174 (5):1824.

Weleber-R G; Tongue-A C; Kennaway-N G; Budden-S S; Baist-N R M; Ophthalmic Manifestations of Infantile Phytanic Acid Storage Disease. Arch-Ophthalmol. 1984; 102: 1317-21.

Wieloch-T, Mattiasson-G, Hansson-M J, Elmer-E. Handbook of Neurochemistry and Molecular Neurobiology. Brain Energetics. Int Mol Cel Processes. Springer US. 2007; 667-702.

Wong-F. Investigating Retinitis Pigmentosa: A Laboratory Scientists Perspective. Prog-Retinal-Eye-Res. 1997; 16 (3): 353-73.

Xu-J, Thornburg-T, Turner-A R, Vitolins-M, Case-D, Shadle-J, Hinson-L, Sun-J, Liu-W, Chang-B, Adams-T S, Zheng-S L, Torti-F M. Serum levels of phytanic acid are associated with prostate cancer risk. Prostate. 2005 May; (15) 63: 209-214.

Yates-A. Study Shows Fish Oils Dramatically Improve Cholesterol Levels in Professional Football Players. 2009. Sport Health.

Yoshizawa-K, Tsubura-A. [Characteristics of N-methyl-N-nitrosourea-induced retinal degeneration in animals and application for the therapy of human retinitis pigmentosa]. Nippon Ganka Gakkai Zasshi. 2005 June; 109(6):327-37.

Yue-J, Thewalt-J L, Cushley-R J. Deuterium nuclear magnetic resonance study of the interaction of branched chain compounds (phytanic acid, phytol) with a phospholipid model membrane. Chem Phys Lipids. 1988 December; 49(3):205-13.

Zhan-H C, Gudas-L J, Bok-D, Rando-R, Nanus-D M, Tickoo-S K. Differential expression of the enzyme that esterifies retinol, lecithin:retinol acyltransferase, in subtypes of human renal cancer and normal kidney. Clin Cancer Res. 2003 October; 9(13):4897-905.

The invention claimed is:

1. A composition comprising omega 3 fatty acids in a range of 65% to 99% by weight and a content in (phytanic acid) PhA below 90 μg/g.

2. The composition according to claim 1, wherein the PhA content is below 5 μg/g.

3. The composition according to claim 1, wherein the range of omega 3 fatty acids is of 75% to 99% by weight.

4. The composition according to claim 3, wherein the range of omega 3 fatty acids is of 90-99% by weight.

5. The composition according to claim 1, wherein the omega 3 fatty acids comprise DHA in a range between 65% and 95% by weight.

6. The composition according to claim 5, wherein the range of DHA is of 75% to 95% by weight.

7. The composition according to claim 6, wherein the range of DHA is of 80-95% by weight.

8. The composition according to claim 1, wherein the omega 3 fatty acids additionally include EPA in a range of 5 to 35% by weight.

9. The composition according to claim 2, wherein the content of DHA is of 80, 65% by weight, the content of EPA is of 13, 38% by weight and the total weight of fatty acids in the mentioned composition is 91, 75% by weight.

10. The composition according to claim 1, additionally comprising excipients and/or adjuvants intended for pharmaceutical and alimentary use.

11. A nutritional supplement which comprises the composition according to claim 1 and a carrier in the form of a drink, soft or hard gels, aqueous emulsion or powder.

12. A food product which comprises the composition according to claim 1 and a food in the form of a drink, soft or hard gels, aqueous emulsion or powder.

13. A pharmaceutical composition which comprises a composition according to claim 1, and a pharmaceutical diluent or carrier.

14. A method for the treatment of allergic conditions in the eye, eye surface and/or dry eye, comprising administering to a patient in need thereof an effective amount of a composition according to claim 1, wherein the condition treated are selected from the group consisting of blepharitis, blepharoconjunctivitis, conjunctivitis, keratitis, dry keratoconjunctivitis.

15. A method for the treatment of glaucoma and macular degeneration diseases non associated with genetic dystrophies comprising administering to a patient in need thereof an effective amount of a composition according to claim 1, wherein the macular degeneration diseases are associated to age.

16. A method for the treatment of hereditary retina dystrophies non retinitis pigmentosa, comprising administering to a patient in need thereof an effective amount of a composition according to claim 1, wherein the hereditary retina dystrophy non retinitis pigmentos treated is selected from the group consisting of Stargardt disease, Leber's congenital amaurosis, Xlinked, Choroideremia, X-linked retinoschisis, Goldman-Favre viteoretinal dystrophy, Wagner's vitreoretinal dystrophy, Stickler's syndrome, Familial Pars Planitis, cystoid macular oedema and Irving-Gass syndrome.

17. A method for the treatment of Retinitis Pigmentosa, comprising administering to a patient in need thereof an effective amount of a composition according to claim 1.

18. A method for the treatment of multiple sclerosis comprising administering to a patient in need thereof an effective amount of a composition according to claim 1.

19. A method for the treatment of nephropaties and patients having undergone renal transplants, comprising administering to a patient in need thereof an effective amount of a composition according to claim 1, wherein the nephropaty treated is selected from the group consisting of nephropathy by IgA, and renal insufficiency associated with malign hypertension and Lupus nephritis.

20. A method for reducing Apoprotein levels, comprising administering to a patient in need thereof an effective amount of a composition according to claim 1.

21. A method for the treatment of androgenic alopecia, comprising administering to a patient in need thereof an effective amount of a composition according to claim 1.

22. A method for the treatment of ulcerative colitis, comprising administering to a patient in need thereof an effective amount of a composition according to claim 1.

23. A method for the treatment of infections caused by *Pseudomonas aeruginosa* or *plasmodiun falciparum*, comprising administering to a patient in need thereof an effective amount of a composition according to claim 1.

24. A method for the treatment of a deficit or DHA or common nutritional DHA deficiency, comprising administering to a patient in need thereof an effective amount of a composition according to claim 1.

25. A method to improve physiological conditions increasing the visual acuity, comprising administering to a patient in need thereof an effective amount of a composition according to claim 1.

* * * * *